(12) United States Patent
Maji et al.

(10) Patent No.: US 12,618,856 B2
(45) Date of Patent: May 5, 2026

(54) ALPHA-SYNUCLEIN MUTANTS AND USES THEREOF

(71) Applicant: Indian Institute of Technology Bombay, Maharashtra (IN)

(72) Inventors: Samir K. Maji, Maharashtra (IN); Gadhe Laxmikant Ganeshrao, Maharashtra (IN); Rakesh Kumar, Maharashtra (IN); Soumik Ray, Maharashtra (IN)

(73) Assignee: INDIAN INSTITUTE OF TECHNOLOGY BOMBAY, Maharashtra (IN)

( * ) Notice: Subject to any disclaimer, the term of this patent is extended or adjusted under 35 U.S.C. 154(b) by 1046 days.

(21) Appl. No.: 17/724,168

(22) Filed: Apr. 19, 2022

(65) Prior Publication Data

US 2022/0341949 A1 Oct. 27, 2022

(30) Foreign Application Priority Data

Apr. 19, 2021 (IN) .............................. 202121018108

(51) Int. Cl.
*G01N 33/68* (2006.01)

(52) U.S. Cl.
CPC . *G01N 33/6896* (2013.01); *G01N 2333/4703* (2013.01); *G01N 2800/2835* (2013.01)

(58) Field of Classification Search
CPC ....... G01N 33/6896; G01N 2333/4703; G01N 2800/2835; C07K 14/47
See application file for complete search history.

(56) References Cited

PUBLICATIONS

Feigin VL et al. The global burden of neurological disorders: translating evidence into policy. Lancet Neurol. Mar. 2020; 19(3):255-265. doi: 10.1016/S1474-4422(19)30411-9. Epub Dec. 5, 2019. PMID: 31813850.
Davie, C. A. (2008) A review of Parkinson's disease. Br. Med. Bull.86, 109-127).
Tysnes, O. B., and Storstein, A. (2017) Epidemiology of Parkinson's disease. J. Neural Transm. 124, 901-905.
Fearnley JM, and Lees AJ (1991) Ageing and Parkinson's disease: substantia nigra regional selectivity. Brain. 114, 2283-2301.
Osterhaus, A., Groen, J., Bildt, M. Van De, Martina, B., Vos, J., and Egmond, H. Van (1997) Î—Synuclein in Lewy bodies Endogenous proviruses as "mementos"?
Stephen J. Wood et al. α-Synuclein Fibrillogenesis Is Nucleation-dependent: implications for the pathogenesis of parkinson's disease*, Journal of Biological Chemistry, vol. 274, Issue 28, 1999, pp. 19509-19512, ISSN 0021-9258, https://doi.org/10.1074/jbc.274.28.19509.
Abeliovich A, Schmitz Y, Farinas I, Choi-Lundberg D, Ho WH, Castillo PE, Shinsky N, Verdugo JM, Armanini M, Ryan A, Hynes M, Phillips H, Sulzer D, Rosenthal A. Mice lacking alpha-synuclein display functional deficits in the higrostriatal dopamine system. Neuron. Jan. 2000;25(1):239-52. doi: 10.1016/s0896-6273(00)80886-7. PMID: 10707987.
El-Agnaf, et al. (2003) Soluble oligomers for the diagnosis of neurodegenerative diseases. Lancet Neurol.2, 461-462.
Ayaka Umemoto et al; The Journal of Biological Chemistry, vol. 289(38): 27290-27299, 2014; and Keita Kakuda et al; Scientific Reports, vol; 9: 6001, 2019.
Anthony B. Mauger et al; Naturally Occurring Proline Analogues; J. Nat. Prod; 10.1021/np9603479; and Anthony B. Mauger et al Analogs and homologs of proline and hydroxyproline; Chem. Rev. 1966, 66, 1, 47-86; doi.org/10.1021/cr60239a003.
Claudio Soto, et al., Cyclic amplification of protein misfolding: application to prion-related disorders and beyond; Trends in Neurosciences vol. 25,390-394,2002.
Ryuichiro Atarashi1et al; Ultrasensitive human prion detection in cerebrospinal fluid by real-time quaking induced conversion; Nature medicine, vol. 17 (2): 175-178, 2011.
Ayaka Umemoto, et al; High-throughput analysis of ultrasonication-forced amyloid fibrillation reveals the mechanism underlying the large fluctuation in the lag time; The Journal of Biological Chemistry, vol. 289(38): 27290-27299, 2014.

*Primary Examiner* — Olga N Chernyshev
(74) *Attorney, Agent, or Firm* — Hauptman Ham, LLP

(57) ABSTRACT

Alpha-Synuclein mutants and uses thereof are disclosed herein. The mutants of the present invention are non-self-aggregating forms of Alpha-Synuclein which make them a suitable candidate for use as substrates in aggregation assay for evaluating the presence of misfolded α-Syn protein. Also disclosed are kits and method for detection of synucleinopathies in individuals, using the mutants of the present invention.

8 Claims, 46 Drawing Sheets

Specification includes a Sequence Listing.

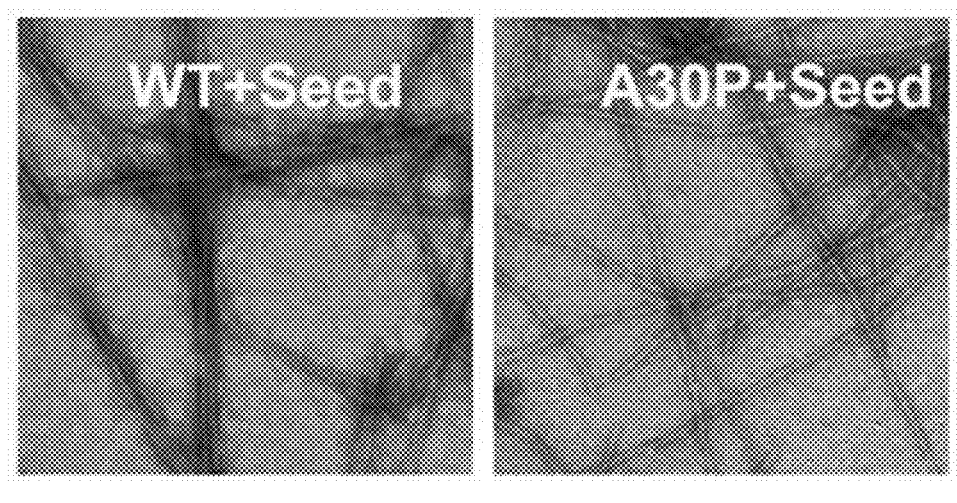
FIG. 4(a)  FIG. 4(b)
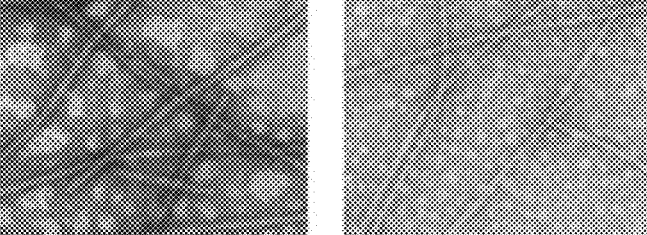
FIG. 4(c)  FIG. 4(d)

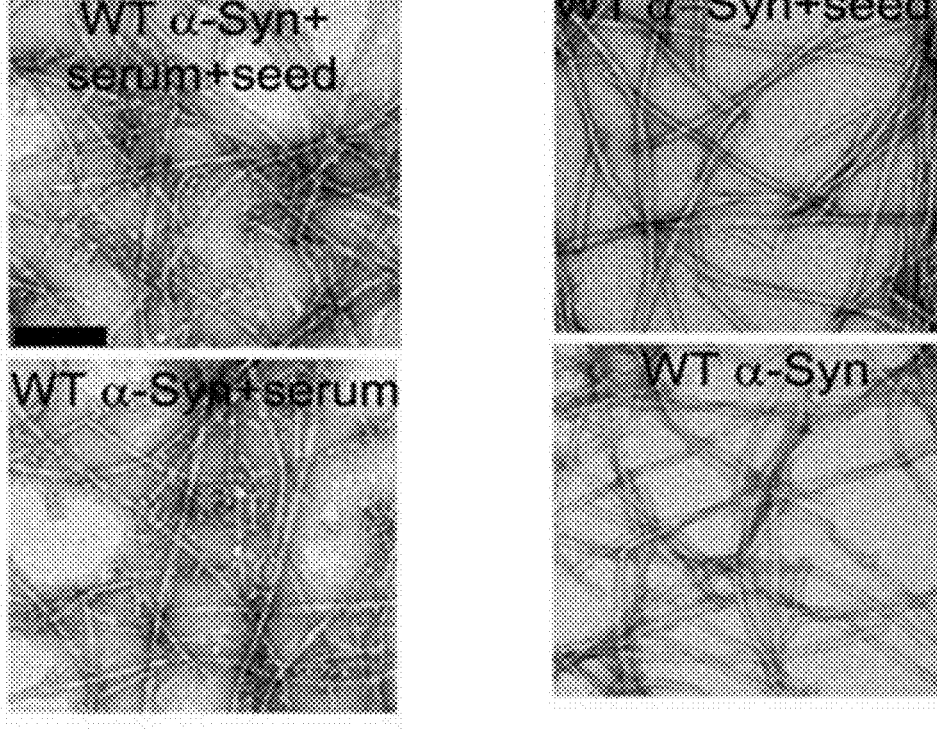
FIG. 14(c)                    FIG. 14(d)

```
                        SEQUENCE LISTING

<160> NUMBER OF SEQ ID NOS: 8

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
        130                 135                 140

<210> SEQ ID NO 2
<211> LENGTH: 140
<212> TYPE: PRT
<213> ORGANISM: Artificial Sequence
<220> FEATURE:
<223> OTHER INFORMATION: Synthesized

<400> SEQUENCE: 2

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Pro Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
```

```
            130                 135                 140

<210> SEQ ID NO 3
<211> LENGTH: 140
<212> TYPE: PRT
<213> ORGANISM: Artificial Sequence
<220> FEATURE:
<223> OTHER INFORMATION: Synthesized

<400> SEQUENCE: 3

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Pro Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 4
<211> LENGTH: 140
<212> TYPE: PRT
<213> ORGANISM: Artificial Sequence
<220> FEATURE:
<223> OTHER INFORMATION: Synthesized

<400> SEQUENCE: 4

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Pro Gly Val
        35                  40                  45

Val His Gly Val Pro Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 5
<211> LENGTH: 423
```

```
<212> TYPE: DNA
<213> ORGANISM: Homo sapiens

<400> SEQUENCE: 5
atggatgtat tcatgaaagg actttcaaag gccaaggagg gagttgtggc tgctgctgag       60
aaaaccaaac agggtgtggc agaagcagca ggaaagacaa aagagggtgt tctctatgta      120
ggctccaaaa ccaaggaggg agtggtgcat ggtgtggcaa cagtggctga gaagaccaaa      180
gagcaagtga caaatgttgg aggagcagtg gtgacgggtg tgacagcagt agcccagaag      240
acagtggagg gagcagggag cattgcagca gccactggct ttgtcaaaaa ggaccagttg      300
ggcaagaatg aagaaggagc cccacaggaa ggaattctgg aagatatgcc tgtggatcct      360
gacaatgagg cttatgaaat gccttctgag gaagggtatc aagactacga acctgaagcc      420
taa                                                                    423

<210> SEQ ID NO 6
<211> LENGTH: 423
<212> TYPE: DNA
<213> ORGANISM: Artificial Sequence
<220> FEATURE:
<223> OTHER INFORMATION: Synthesized

<400> SEQUENCE: 6
atggatgtat tcatgaaagg actttcaaag gccaaggagg gagttgtggc tgctgctgag       60
aaaaccaaac agggtgtggc agaagcagca ggaaagacaa aagagggtgt tctctatgta      120
ggctccaaaa ccaagccggg agtggtgcat ggtgtggcaa cagtggctga gaagaccaaa      180
gagcaagtga caaatgttgg aggagcagtg gtgacgggtg tgacagcagt agcccagaag      240
acagtggagg gagcagggag cattgcagca gccactggct ttgtcaaaaa ggaccagttg      300
ggcaagaatg aagaaggagc cccacaggaa ggaattctgg aagatatgcc tgtggatcct      360
gacaatgagg cttatgaaat gccttctgag gaagggtatc aagactacga acctgaagcc      420
taa                                                                    423

<210> SEQ ID NO 7
<211> LENGTH: 423
<212> TYPE: DNA
<213> ORGANISM: Artificial Sequence
<220> FEATURE:
<223> OTHER INFORMATION: Synthesized

<400> SEQUENCE: 7
atggatgtat tcatgaaagg actttcaaag gccaaggagg gagttgtggc tgctgctgag       60
aaaaccaaac agggtgtggc agaagcagca ggaaagacaa aagagggtgt tctctatgta      120
ggctccaaaa ccaaggaggg agtggtgcat ggtgtgccga cagtggctga gaagaccaaa      180
gagcaagtga caaatgttgg aggagcagtg gtgacgggtg tgacagcagt agcccagaag      240
acagtggagg gagcagggag cattgcagca gccactggct ttgtcaaaaa ggaccagttg      300
ggcaagaatg aagaaggagc cccacaggaa ggaattctgg aagatatgcc tgtggatcct      360
gacaatgagg cttatgaaat gccttctgag gaagggtatc aagactacga acctgaagcc      420
taa                                                                    423

<210> SEQ ID NO 8
<211> LENGTH: 423
<212> TYPE: DNA
<213> ORGANISM: Artificial Sequence
<220> FEATURE:
```

-continued

```
<223> OTHER INFORMATION: Synthesized

<400> SEQUENCE: 8
atggatgtat  tcatgaaagg  actttcaaag  gccaaggagg  gagttgtggc  tgctgctgag        60
aaaaccaaac  agggtgtggc  agaagcagca  ggaaagacaa  aagagggtgt  tctctatgta       120
ggctccaaaa  ccaagccggg  agtggtgcat  ggtgtgccga  cagtggctga  gaagaccaaa       180
gagcaagtga  caaatgttgg  aggagcagtg  gtgacgggtg  tgacagcagt  agcccagaag       240
acagtggagg  gagcagggag  cattgcagca  gccactggct  ttgtcaaaaa  ggaccagttg       300
ggcaagaatg  aagaaggagc  cccacaggaa  ggaattctgg  aagatatgcc  tgtggatcct       360
gacaatgagg  cttatgaaat  gccttctgag  gaagggtatc  aagactacga  acctgaagcc       420
taa                                                                          423
```

ALPHA-SYNUCLEIN MUTANTS AND USES THEREOF

CROSS REFERENCE TO RELATED APPLICATION

This application is based on and derives the benefit of Indian Provisional Application 202121018108 filed on the 19 Apr. 2021, the contents of which are incorporated herein by reference.

TECHNICAL FIELD

The present invention relates to alpha-Synuclein mutants and more particularly to alpha-Synuclein mutants having modified aggregation properties. Further, it relates to a kit and method for detection of Synucleinopathies such as Parkinson's disease (PD) using alpha-Synuclein mutants.

INCORPORATION BY REFERENCE

The sequence listing provided in the file entitled SequenceListingv2GPB.txt, which is an ASCII text file that was created on Apr. 19, 2022, and which comprises 8,290 bytes, is hereby incorporated by reference in its entirety.

BACKGROUND

Neurological disorders have risen substantially in the past 30 years, and it is a leading source of disability globally (Feigin V L et al. *The global burden of neurological disorders: translating evidence into policy. Lancet Neurol.* 2020 March; 19(3):255-265. doi: 10.1016/S1474-4422(19)30411-9. Epub 2019 December 5. PMID: 31813850). Parkinson's disease (PD) is the second most common progressive neurological disorder after Alzheimer's disease (AD).

The prevalence of PD is 160/100000 in Western Europe (Davie, C. A. (2008) *A review of Parkinson's disease. Br. Med. Bull.* 86, 109-127) and it affects 1-2 per 1000 of population at any time. The prevalence of PD increases up to ~1% of the population for age groups more than 60 years (Tysnes, O. B., and Storstein, A. (2017) *Epidemiology of Parkinson's disease. J. Neural Transm.* 124, 901-905). According to the global burden of disease study 2016, the overall number of people affected by PD is 6.1 million globally and Parkinson's disease is the fastest growing neurological disorder. Parkinson's disease is characterized by shaking, rigidity, bradykinesia, and difficulties with walking. Julian M et al reported Parkinson's disease is primarily characterized by neuronal deaths mainly in Striatum and Substantia nigra (SN) regions of the brain (Fearnley J M, and Lees A J (1991) *Ageing and Parkinson's disease: substantia nigra regional selectivity. Brain.* 114, 2283-2301). These neurons mainly play a role in the synthesis of dopamine neurotransmitters. Degeneration of dopaminergic neurons of substantia nigra results in impairment in motor functions as well as non-motor functions. Secondary symptoms may include neuropsychiatric dysfunction, sleep disorders, autonomic dysfunction, sensory symptoms, and pain, etc. The primary pathological hallmarks of PD are degeneration of dopaminergic neurons in the substantia nigra pars compacta region of the midbrain and the deposition of a protein in the form of Lewy bodies. α-Syn protein (140 amino acid long) is a major component of Lewy bodies in PD patient brain tissue (Osterhaus, A., Groen, J., Bildt, M. Van De, Martina, B., Vos, J., and Egmond, H. Van (1997) *Î-Synuclein in Lewy bodies Endogenous proviruses as*

*"mementos"?*). Isolated amyloid from Lewy body showed similar fibril-like morphology to that of in vitro fibrils of α-Syn. The α-Syn aggregation is shown to be nucleation dependent process and it can be seeded by misfolded nuclei or fibril of α-Syn (Stephen J. Wood. Et al. α-*Synuclein Fibrillogenesis Is Nucleation-dependent: implications for the pathogenesis of parkinson's disease *, Journal of Biological Chemistry,* Volume 274, Issue 28, 1999, Pages 19509-19512, ISSN 0021-9258, https://doi.org/10.1074/jbc.274.28.19509).

The physiological function of α-Syn is unclear, but it is considered to be involved in vesicular trafficking, synaptic function, and neurotransmitter release (Abeliovich A, Schmitz Y, Fariñas I, Choi-Lundberg D, Ho W H, Castillo P E, Shinsky Verdugo J M, Armanini M, Ryan A, Hynes M, Phillips H, Sulzer D, Rosenthal A. *Mice lacking alpha-synuclein display functional deficits in the nigrostriatal dopamine system. Neuron.* 2000 January; 25(1):239-52, doi: 10.1016/s0896-6273(00)80886-7. PMID: 10707987). The multiplication and disease-linked point mutation in the SNCA gene lead to the acceleration of α-Syn oligomerization and fibrillation that cause the early onset of PD. α-Syn is also associated with filamentous inclusion of multiple system atrophy (MSA) and dementia with Lewy body (DLB) that have the filamentous pathology in nerve cells and glial cells. Synucleinopathy, a term used for diseases that show the common involvement of accumulated aggregates of α-Syn in nerve cells, glial cells, or nerve fibers. Mutations in the SNCA gene (such as duplications, triplications, or point mutation), which encodes α-Syn are associated with the autosomal dominant form of PD.

Parkinson's disease is characterized by a variety of motor and non-motor symptoms that affect the lifestyle of the individual to a variable degree. As there is no definitive diagnostic test available, Parkinson's disease diagnosis is mainly based on clinical criteria but the pathological process that leads to PD begins decades before the onset of motor symptoms. It is estimated that almost 50-70% of neurons have been already lost by the time when first motor symptoms emerge. So, it is very important to identify the markers of preclinical Parkinson's disease because neuroprotective treatments should be used before the clinical onset of PD. The development of a novel robust marker of Parkinson's disease would assist in disease progression and targeted therapeutics. Monomeric α-Syn protein aggregates into soluble oligomeric intermediates. The oligomers are a central and early-stage event in the pathogenesis of PD. It is found that accumulation of α-Syn oligomers results in neuronal degeneration. Hence the detection of oligomers can be used as a biomarker for the precise and early detection of synucleinopathies (El-Agnaf, et al. (2003) *Soluble oligomers for the diagnosis of neurodegenerative diseases. Lancet Neurol.* 2, 461-462). Various research groups have shown elevated level of oligomeric α-Syn in cerebrospinal fluid (CSF), blood, saliva, etc. of patients with PD compared with control. Although, oligomeric form of α-Syn, in red blood cells, plasma and serum, has been identified as a PD biomarker, diagnostic accuracy is inconsistent and unsatisfactory. Thus, it is highly crucial to develop a robust, sensitive, and specific assay for detection of misfolded α-Syn in the patient sample.

Several artificial α-Syn mutants demonstrating accelerated aggregation, increased toxicity, etc. have been developed. Further, quantitative (protein misfolding cyclic amplification) PMCA method to estimate the prion concentration in fluids and tissues have also been developed. Detection methods also include incubation of soluble misfolded α-Syn protein present in sample with monomeric substrate to achieve amplification of protein aggregation. α-Syn real time-quaking induced conversion (RT-QuIC) assay using recombinant α-Syn protein as substrate to detect misfolded α-Syn in a sample has earlier been developed. A new technique, HANdai Amyloid Burst Inducer (HANABI) technique has been proposed as an alternative to PMCA and RT-QuIC methods for automatic and rapid analysis of fibrillation of proteins. It mainly involves sonication and incubation cycles with real-time monitoring of a fluorescent signal (Ayaka Umemoto et al; *The Journal of Biological Chemistry*, Vol: 289(38): 27290-27299, 2014; and Keita Kakuda et al; Scientific Reports, vol; 9: 6001, 2019. ). Sonication-based HANABI assays are rapid technique to detect α-Syn aggregates. Prion related disorders are associated with the conversion of the natively folded α-helix rich prion protein (PrP) into a misfolded β-structure rich insoluble conformer (PrP$^{Sc}$). The afore-mentioned techniques have become highly specific and sensitive for natively folded protein such as prion protein. But the specificity of these techniques is drastically reduced when natively unstructured protein with spontaneous aggregation ability is used, which leads to false-positive results.

The amplified product using above mentioned techniques can be further detected using classical methods such as western blot assay, ThT fluorescence assay, and imaging techniques. However, these techniques are highly cumbersome and time consuming. Therefore, there is a need for developing a substrate that lacks spontaneous aggregation ability but can aggregate in presence of seed, and an assay to detect the amplified product with high precision and considerable ease.

Objects

The principal object of the embodiments disclosed herein is to provide artificial α-Syn mutants.

A second object of the embodiments disclosed herein is to provide α-Syn mutants having reduced self-aggregating ability, which are capable of aggregation in the presence of seed.

Another object of the embodiments disclosed herein is to provide a substrate for detection of Synucleinopathies.

Another object of the embodiments disclosed herein is to provide a substrate for detection of Parkinson's disease.

An object of the embodiments disclosed herein is to provide a substrate for detection of α-Syn protein, or oligomers, aggregates or seeds thereof.

An object of the embodiments disclosed herein is to provide a substrate for protein misfolding cyclic amplification (PMCA) method.

Further, an object of the embodiments disclosed herein is to provide a method for detection of Synucleinopathies, such as Parkinson's disease.

Another object of the embodiments disclosed herein is to provide a method for detection of α-Syn protein, or oligomers, or aggregates, or seeds thereof.

An object of the embodiments disclosed herein is to provide an assay method for detection of α-Syn protein, or oligomers, or aggregates thereof, in biological fluid, particularly blood, plasma or serum.

Another object of the embodiments herein is to provide a high throughput screening method for detection of Synucleinopathies, such as Parkinson's disease, using Congo red dot test.

Yet another object of the embodiments disclosed herein is to provide a non-invasive, highly specific, and sensitive assay method using α-Syn mutants.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings. The embodiments herein will be better understood from the following description with reference to the drawings, in which:

FIGS. 1(*b*) to 1(*e*) are TEM images; wherein 1(*b*) and 1(*c*) are WT and A30P showing fibrillar morphology, whereas 1(*d*) and 1(*e*) are E46P and A53P showing globular and granular morphology, respectively;

FIGS. 4(*a*) to 4(*d*) are TEM images showing morphology of aggregates at end of seeding; wherein 4(*a*) depicts WT with WT seeds, 4(*b*) depicts A30P with WT seeds, 4(*c*) depicts E46P with WT seeds, and 4(*d*) depicts A53P with WT seeds, respectively;

FIGS. 9(*d*) to 9(*g*) are TEM images depicting morphological changes in E46P protein with or without WT oligomer, after aggregation kinetics; wherein 9(*d*) depicts E46P with $10^{-9}$M WT oligomer; 9(*e*) depicts E46P with $10^{-12}$M WT oligomer; 9(*f*) depicts E46P with $10^{-15}$ M WT oligomer, and 9(*g*) depicts E46 alone, respectively;

FIGS. 13(*e*) to 13(*h*) are CD spectra showing the structural transition of WT after incubating with WT seed spiked serum and in absence of seed spiked serum; wherein 13(*e*) depicts WT alone; 13(*f*) depicts WT with serum; 13(*g*) depicts WT incubated with $10^{-12}$M WT; 13(*h*) depicts WT incubated with serum and $10^{-12}$M WT, respectively;

FIGS. 23(*m*) to 23(*s*) are CD spectra for samples HC1 to HC7 respectively, after completion of each round of PMCA;

FIGS. 24(*m*) to 24(*s*) are TEM micrographs for samples HC1 to HC7 respectively, after completion of $1^{st}$ and $4^{th}$ round of PMCA;

FIG. 25(*c*) is a graph depicting quantification of congo red blot assay illustrating the intensity of congo red dye retention among patient samples and corresponding controls after completion of PMCA assay.

DETAILED DESCRIPTION

Figure 1A:
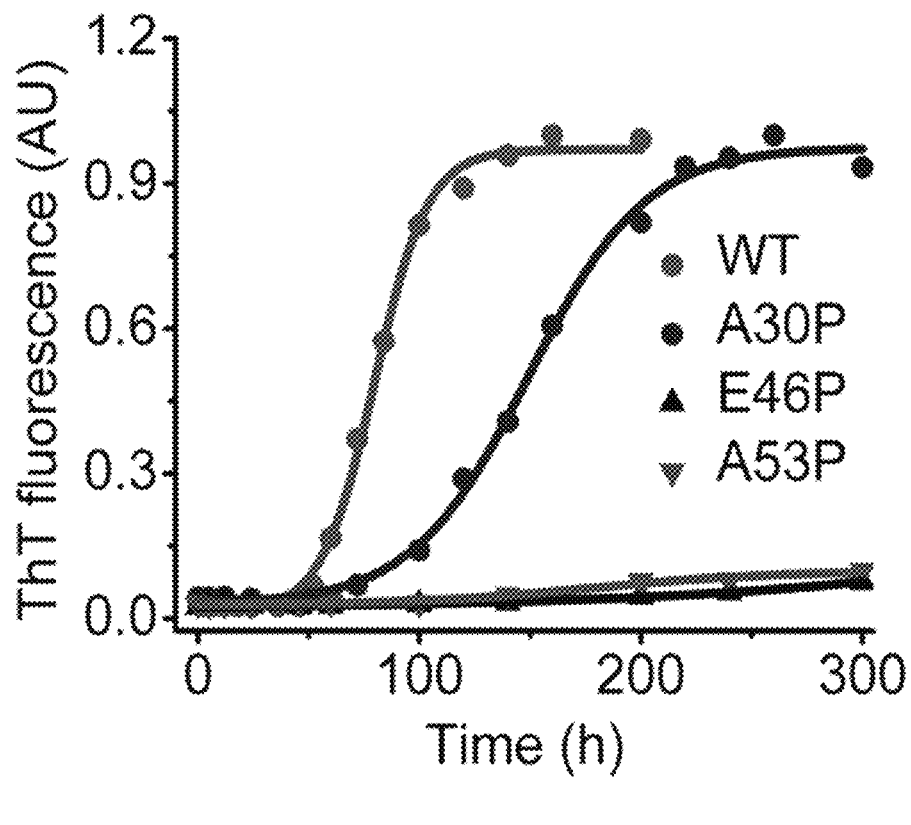
FIG. 1(*a*) is a graph of ThT binding assay results showing increased binding for WT and A30P with time and no ThT fluorescence for E46P and A53P, respectively.
Figure 1B:
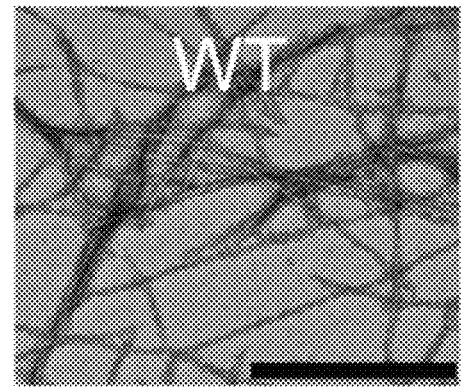
Figure 1C:
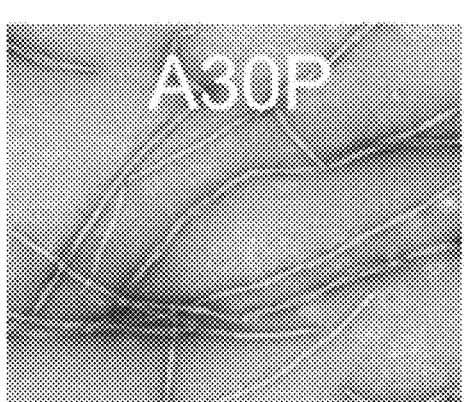
Figure 1D:
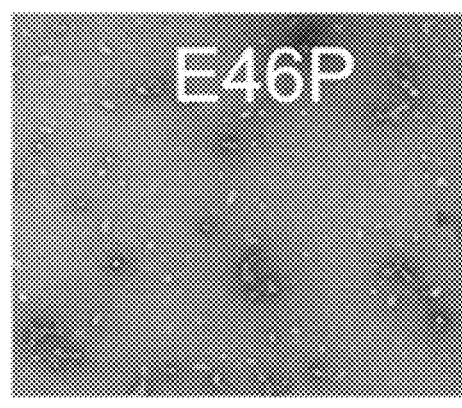
Figure 1E:
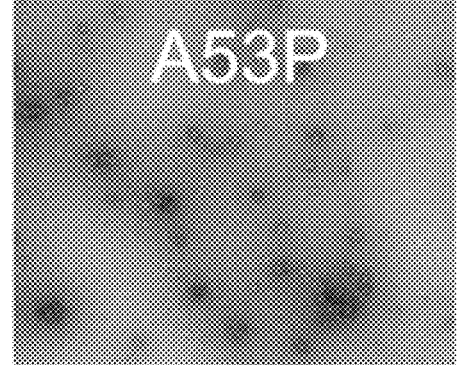

The embodiments herein and the various features and advantageous details thereof are explained more fully with reference to the non-limiting embodiments that are illustrated in the accompanying drawings and detailed in the following description. Descriptions of well-known components and processing techniques are omitted so as not to unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein disclose artificial alpha-synuclein (herein also referred to as α-Syn or α-Synuclein) protein, or peptide thereof. The artificial α-Syn, according to embodiments herein, is a mutant of wild type α-Syn, particularly human α-Syn. The disclosed mutants include amino acid substitution mutation at specific position which modulates the aggregation potential of α-Syn. Unlike wild type α-Syn, and various other forms of synthetic or recombinant α-Syn, which are capable of spontaneous self-aggregation, the disclosed mutants have reduced or no self-aggregating ability. It is observed by the present inventors that the substitution mutation impairs fibril nucleation ability of α-Syn leading to modulation in self-aggregation properties. However, the mutants, according to embodiments herein, are capable of aggregation or formation of amyloid structures in the presence of seed. Therefore, the disclosed mutants may be used as substrates in detection of α-Syn protein, or oligomers, or aggregates, or any seeds thereof in samples. Accordingly, embodiments herein include α-Syn mutants for detection of synucleinopathies. Wild type α-Syn when used as substrate has a tendency to spontaneously self-aggregate over time producing false positive results in detection of α-Syn, which is a limitation that is overcome by the disclosed embodiments. Therefore, the embodiments herein provide a specific and accurate method/substrate for detection of synucleinopathies and/or α-Syn protein, monomers, oligomers, aggregates, etc. Embodiments herein are capable of detecting minute concentrations of α-Syn, for example as little as picomolar and femtomolar concentration. Accordingly, embodiments herein include mutants capable of use in detecting synucleinopathies at an early stage, much before the onset of clinical symptoms of the disease. Embodiments herein disclose a method for detection of synucleinopathies in an individual, using the disclosed mutants. Further embodiments include a kit for detection of synucleinopathies in an individual.

Alpha-Synuclein Mutants

The embodiments herein disclose α-Syn mutants, or species thereof. In an embodiment, the α-Syn mutants comprise a polypeptide derived from wild type α-Syn having substitution mutation of at least one amino acid selected from glutamic acid at $46^{th}$ position and alanine at $53^{th}$ position. The term "mutants" or "mutant", as used herein, refers to mutant(s) of a-synuclein. α-Syn is a neuronal protein which in humans is encoded by the SNCA gene. α-Syn, according to embodiments herein, includes wild type α-Syn, including various isoforms such as SNCA140, SNCA126, SNCA112 and SNCA98. It further includes α-Syn protein in various structural forms including, but not limited to, its monomeric, oligomeric, amyloid structure, fibrillar form and/or aggregate forms; folded, unfolded and/ or misfolded forms of α-Syn. It further includes fragments, polypeptides, etc. of α-Syn protein. It refers to α-Syn protein having modified aggregation potential. In an embodiment, it refers to α-Syn having reduced or no self-aggregating ability. The mutants, according to embodiments herein, refer to artificial α-Syn that are capable of aggregation in the presence of a seed. In an embodiment, the mutant refers to α-Syn having impaired fibril nucleation ability. In an embodiment, the mutant comprises a polypeptide sequence having at least 70% amino acid sequence identity to a sequence set forth in SEQ ID NO: 1. SEQ ID NO.1 provides the amino acid sequence of wild type α-Syn. In an embodiment, the mutant comprises a polypeptide having an amino acid sequence derived from the amino acid sequence set forth in SEQ ID NO: 1. In an embodiment, the mutant comprises polypeptide having an amino acid sequence derived from the amino acid sequence of a homologue of SEQ ID NO: 1. In some embodiments, the mutant comprises a polypeptide having amino acid sequence identity of at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, or at least 99.5%, to that of SEQ ID NO: 1. In an embodiment, the mutant α-Synuclein is derived from a wild type α-Synuclein having amino acid substitution mutation of at least one amino acid selected from glutamic acid at $46^{th}$ position and alanine at $53^{rd}$ position. In an embodiment, the mutant α-Synuclein comprises a polypeptide having an amino acid sequence of SEQ ID NO: 1, wherein said SEQ ID NO: 1 includes substitution mutation of at least one amino acid selected from glutamic acid at $46^{th}$ position and alanine at $53^{rd}$ position. In another embodiment, the mutant comprises a polypeptide having amino acid sequence derived from the amino acid sequence set forth in SEQ ID NO: 1, or homologue thereof, by substitution mutation of glutamic acid at $46^{th}$ position and/or alanine at $53^{rd}$ position. In an embodiment, the mutant is E46P mutant of wild type α-Syn. In another embodiment, the mutant is A53P mutant of wild type α-Syn.

Substitution mutation, in embodiments herein, at $46^{th}$ and/or $53^{rd}$ may include conservative or non-conservative replacement. In an embodiment, the substitution mutation at $46^{th}$ and/or $53^{rd}$ is with proline residues. It has been observed that mutation at these positions modulates the aggregation propensity of α-Syn. While proline residues are used for substitution in various embodiments herein, it is understood that similar synthetic structures or moieties, proline analogs, proline derivatives, etc. for example having at least 70% to 90% structural similarity to proline residue may also be used to achieve the disclosed mutants in light of the disclosures made herein. All such modifications and variation would be apparent to a person skilled in the art in light of the present disclosure and may be practiced without departing from the scope and spirit of the present invention. Examples of proline analogs and derivatives include, but are not limited to, hydroxyproline, alkylproline, bromoproline, dehydroproline, aminoproline, etc. Various example of such analogs and derivatives are described in Anthony B. Mauger et al; *Naturally Occurring Proline Analogues; J. Nat. Prod;* 10.1021/np9603479; and Anthony B. Mauger et al Analogs and homologs of proline and hydroxyproline; *Chem. Rev.* 1966, 66, 1, 47-86; doi.org/10.1021/cr60239a003, disclosure of which are incorporated herein by reference.

The unique structure of proline destabilizes helix and (3-sheet structure of the amino acid sequence, which contribute to the unique nature or properties of the disclosed mutants. In an embodiment, the substitution mutation includes proline substitution of at least one amino acid selected from glutamic acid at $46^{th}$ position and alanine at $53^{rd}$ position. In another embodiment, the substitution mutation includes substitution of at least one amino acid selected from glutamic acid at $46^{th}$ position and alanine at $53^{rd}$ position with a moiety having at least 70 to 90% structural identity with that of proline. In another embodiment, the substitution mutation includes substitution of at least one amino acid selected from glutamic acid at $46^{th}$ position and alanine at $53^{rd}$ position with a derivative of proline. In an embodiment, the substitution mutation is of glutamic acid at $46^{th}$ position. In another embodiment, the substitution mutation is of alanine at $53^{rd}$ position. In another embodiment, the substitution mutation is of glutamic acid at $46^{th}$ position and alanine at $53^{rd}$ position.

In an embodiment, the mutant comprises at least one polypeptide, or fragment thereof, having an amino acid sequence selected from a group consisting of SEQ ID NO: 2, SEQ ID NO: 3, and SEQ ID NO: 4. In some embodiments, the polypeptide strand is one having amino acid sequence identity of at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, or at least 99.5%, to that of SEQ ID NO: 2, SEQ ID NO: 3, or SEQ ID NO: 4. In an embodiment, the amino acid substitution is selected from E46P and A53P. In an embodiment, the amino acid substitution is E46P. In another embodiment, the amino acid substitution is A53P. In yet another embodiment, the amino acid substitution is E46P and A53P. In an embodiment, the mutant comprises a polypeptide having amino acid sequence of SEQ ID NO: 2. In another embodiment, the mutant comprises a polypeptide having amino acid sequence of SEQ ID NO: 3. In an embodiment, the mutant comprises a polypeptide having amino acid sequence of SEQ ID NO: 4. In an embodiment, the mutant comprises a polypeptide, or fragment thereof, having amino acid sequence derived from the sequence set forth in SEQ ID NO: 1, or homologue thereof, by amino acid substitution of E46P. In another embodiment, the mutant comprises an amino acid sequence, or fragment thereof, derived from the sequence set forth in SEQ ID NO: 1, or homologue thereof, by amino acid substitution of A53P. In another embodiment, the mutant comprises a polypeptide, or fragment thereof, amino acid sequence derived from the sequence set forth in SEQ ID NO: 1, or homologue thereof, by amino acid substitutions of A53P and E46P.

The term "species", as used herein, includes, but is not limited to, fragments, homologues, variants, polypeptides, analogues, conjugates, etc. of α-Syn mutants. Accordingly, embodiments herein include fragments, homologues, variants, polypeptides, analogues, conjugates, etc of α-Syn mutants. In an embodiment, species refers to a polypeptide of mutant α-Syn. In another embodiment, species refers to a fragment of mutant α-Syn. In another embodiment, species is a fragment comprising one or more peptide sequences, with or without surface modifications, functional groups, side chains, etc., of mutant α-Syn. In another embodiment, species refers to a homologue or analogue of mutant α-Syn. In another embodiment, species refers to a conjugate of mutant α-Syn, or peptide or fragment thereof. In an embodiment, the polypeptide comprises substitution mutation of at least one amino acid selected from glutamic acid at $46^{th}$ position and alanine at $53^{rd}$ position. In an embodiment, it includes polypeptides having at least 70% amino acid sequence identity to SEQ ID NO: 1, wherein said sequence includes a proline substitution mutation of at least one amino acid selected from glutamic acid at $46^{th}$ position and alanine at $53^{rd}$ position. The conjugates, as disclosed herein, refers to any conjugate comprising at least one amino acid sequence having at least 70% amino acid sequence identity to SEQ ID NO: 1 wherein the sequence includes substitution mutation of at least one amino acid selected from glutamic acid at $46^{th}$ position and alanine at $53^{rd}$ position. The conjugate may further include one or more other moieties such as linkers, aptamers, peptides, polynucleotides, antigen binding agents, antibodies, glycopeptides, carriers, detectable labels (such as fluorescent label, radiolabels, fluorescent nanoparticle, gold label, an enzyme, etc). In an embodiment, the conjugate is an immunoconjugate comprising a polypeptide with an amino acid sequence having at least 70% amino acid sequence identity to SEQ ID NO: 1 wherein the sequence includes substitution mutation of at least one amino acid selected from glutamic acid at $46^{th}$ position and alanine at $53^{rd}$ position, and at least one aptamer or antigen binding moiety. In an embodiment, the immunoconjugate comprises at least one α-Syn mutant and an aptamer or antigen binding moiety. The aptamer or antigen binding moiety may be linked covalently or non-covalently, or through a suitable linker molecule, to the α-Syn mutant, or species thereof. Various linkers are generally known in the art and may be used herein. Linkers include, but are not limited to, a polypeptide, a DNA, a RNA, an aliphatic chain, spacer or an adaptor. In some embodiments, the conjugate includes linkers which may be chosen to achieve immobilization of the disclosed mutants on various polymer substrates such as nitrocellulose, cellulose, paper, etc. It is understood that various such modifications would be apparent to a person skilled in the art in light of the disclosures made herein and are included within the scope of the embodiments herein. Table 1 is a list of amino acid and polypeptide sequences and SEQ ID Nos for wild type α-Synuclein and mutants thereof.

TABLE 1

Sequence listing

| SEQ ID NO. | DESCRIPTION | TYPE | SEQUENCE |
|---|---|---|---|
| 1 | Alpha-synuclein Wild type | Amino acid sequence | MDVFMKGLSKAKEGVVAAAEKTKQ GVAEAAGKTKEGVLYVGSKTKEGV VHGVATVAEKTKEQVTNVGGAVVT GVTAVAQKTVEGAGSIAAATGFVKK DQLGKNEEGAPQEGILEDMPVDPDN EAYEMPSEEGYQDYEPEA |
| 2 | Mutant 1 (E46P) | Amino acid sequence | MDVFMKGLSKAKEGVVAAAEKTKQ GVAEAAGKTKEGVLYVGSKTKPGV VHGVATVAEKTKEQVTNVGGAVVT GVTAVAQKTVEGAGSIAAATGFVKK DQLGKNEEGAPQEGILEDMPVDPDN EAYEMPSEEGYQDYEPEA |
| 3 | Mutant 2 (A53P) | Amino acid sequence | MDVFMKGLSKAKEGVVAAAEKTKQ GVAEAAGKTKEGVLYVGSKTKEGV VHGVPTVAEKTKEQVTNVGGAVVT GVTAVAQKTVEGAGSIAAATGFVKK DQLGKNEEGAPQEGILEDMPVDPDN EAYEMPSEEGYQDYEPEA |
| 4 | Mutant 3 (E46P + A53P) | Amino acid sequence | MDVFMKGLSKAKEGVVAAAEKTKQ GVAEAAGKTKEGVLYVGSKTKPGV VHGVPTVAEKTKEQVTNVGGAVVT GVTAVAQKTVEGAGSIAAATGFVKK DQLGKNEEGAPQEGILEDMPVDPDN EAYEMPSEEGYQDYEPEA |
| 5 | Alpha-synuclein Wild type | Poly-nucleotide sequence | ATGGATGTATTCATGAAAGGACTTT CAAAGGCCAAGGAGGGAGTTGTGG CTGCTGCTGAGAAAACCAAACAGG GTGTGGCAGAAGCAGCAGGAAAGA CAAAAGAGGGTGTTCTCTATGTAGG CTCCAAAACCAAGGAGGGAGTGGT |

TABLE 1-continued

Sequence listing

| SEQ ID NO. | DESCRIPTION | TYPE | SEQUENCE |
|---|---|---|---|
| | | | GCATGGTGTGGCAACAGTGGCTGA<br>GAAGACCAAAGAGCAAGTGACAAA<br>TGTTGGAGGAGCAGTGGTGACGGG<br>TGTGACAGCAGTAGCCCAGAAGAC<br>AGTGGAGGGAGCAGGGAGCATTGC<br>AGCAGCCACTGGCTTTGTCAAAAA<br>GGACCAGTTGGGCAAGAATGAAGA<br>AGGAGCCCCACAGGAAGGAATTCT<br>GGAAGATATGCCTGTGGATCCTGAC<br>AATGAGGCTTATGAAATGCCTTCTG<br>AGGAAGGGTATCAAGACTACGAAC<br>CTGAAGCCTAA |
| 6 | Mutant 1<br>(E46P) | Poly-<br>nucleotide<br>sequence | ATGGATGTATTCATGAAAGGACTTT<br>CAAAGGCCAAGGAGGGAGTTGTGG<br>CTGCTGCTGAGAAAACCAAACAGG<br>GTGTGGCAGAAGCAGCAGGAAAGA<br>CAAAAGAGGGTGTTCTCTATGTAGG<br>CTCCAAAACCAAGCCGGGAGTGGT<br>GCATGGTGTGGCAACAGTGGCTGA<br>GAAGACCAAAGAGCAAGTGACAAA<br>TGTTGGAGGAGCAGTGGTGACGGG<br>TGTGACAGCAGTAGCCCAGAAGAC<br>AGTGGAGGGAGCAGGGAGCATTGC<br>AGCAGCCACTGGCTTTGTCAAAAA<br>GGACCAGTTGGGCAAGAATGAAGA<br>AGGAGCCCCACAGGAAGGAATTCT<br>GGAAGATATGCCTGTGGATCCTGAC<br>AATGAGGCTTATGAAATGCCTTCTG<br>AGGAAGGGTATCAAGACTACGAAC<br>CTGAAGCCTAA |
| 7 | Mutant 2<br>(A53P) | Poly-<br>nucleotide<br>sequence | ATGGATGTATTCATGAAAGGACTTT<br>CAAAGGCCAAGGAGGGAGTTGTGG<br>CTGCTGCTGAGAAAACCAAACAGG<br>GTGTGGCAGAAGCAGCAGGAAAGA<br>CAAAAGAGGGTGTTCTCTATGTAGG<br>CTCCAAAACCAAGGAGGGAGTGGT<br>GCATGGTGTGCCGACAGTGGCTGA<br>GAAGACCAAAGAGCAAGTGACAAA<br>TGTTGGAGGAGCAGTGGTGACGGG<br>TGTGACAGCAGTAGCCCAGAAGAC<br>AGTGGAGGGAGCAGGGAGCATTGC<br>AGCAGCCACTGGCTTTGTCAAAAA<br>GGACCAGTTGGGCAAGAATGAAGA<br>AGGAGCCCCACAGGAAGGAATTCT<br>GGAAGATATGCCTGTGGATCCTGAC<br>AATGAGGCTTATGAAATGCCTTCTG<br>AGGAAGGGTATCAAGACTACGAAC<br>CTGAAGCCTAA |
| 8 | Mutant 3<br>(E46P +<br>A53P) | Poly-<br>nucleotide<br>sequence | ATGGATGTATTCATGAAAGGACTTT<br>CAAAGGCCAAGGAGGGAGTTGTGG<br>CTGCTGCTGAGAAAACCAAACAGG<br>GTGTGGCAGAAGCAGCAGGAAAGA<br>CAAAAGAGGGTGTTCTCTATGTAGG<br>CTCCAAAACCAAGCCGGGAGTGGT<br>GCATGGTGTGCCGACAGTGGCTGA<br>GAAGACCAAAGAGCAAGTGACAAA<br>TGTTGGAGGAGCAGTGGTGACGGG<br>TGTGACAGCAGTAGCCCAGAAGAC<br>AGTGGAGGGAGCAGGGAGCATTGC<br>AGCAGCCACTGGCTTTGTCAAAAA<br>GGACCAGTTGGGCAAGAATGAAGA<br>AGGAGCCCCACAGGAAGGAATTCT<br>GGAAGATATGCCTGTGGATCCTGAC<br>AATGAGGCTTATGAAATGCCTTCTG<br>AGGAAGGGTATCAAGACTACGAAC<br>CTGAAGCCTAA |

Generation of Non-Self-Aggregating Mutants

The mutants, according to embodiments herein, may be synthesized by methods generally known in the art. Various techniques of inducing substitution mutation are known in the field which may be employed to induce substitution of glutamic acid at 46$^{th}$ position and/or alanine at 53$^{rd}$ position. Further, as per generally known technique, the mutants may be produced by inducing mutation to the amino acid strand or gene or polynucleotide strand encoding wild type α-Syn, or homologue thereof. Accordingly, embodiments herein include an artificial polynucleotide strand encoding the disclosed mutants. The polynucleotide strand, according to embodiments herein, includes single or double stranded DNA strand or RNA strand e.g.: mRNA. In an embodiment, the nucleotide strand comprises a sequence encoding the amino acid sequence set forth in SEQ ID NO: 2, or homologue thereof. In an embodiment, the polynucleotide strand comprises a sequence set forth in SEQ ID NO: 6 or its complimentary sequence. In another embodiment, the nucleotide comprises a sequence encoding the amino acid sequence set forth in SEQ ID NO: 3, or homologue thereof. In an embodiment, the polynucleotide comprises a sequence set forth in SEQ ID NO: 7 or its complimentary sequence. In yet another embodiment, the nucleotide comprises a sequence encoding the amino acid sequence set forth in SEQ ID NO: 4, or homologue thereof. In an embodiment, the polynucleotide comprises a sequence set forth in SEQ ID NO: 8 or its complimentary sequence. In some embodiments, the polynucleotide strand is one having sequence identity of at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, or at least 99.5%, to that of SEQ ID NO: 6, SEQ ID NO: 7, or SEQ ID NO: 8.

The nucleotide, according to embodiments herein, may further be introduced into a suitable plasmid to obtain a recombinant plasmid. Accordingly, embodiments herein include a plasmid vector comprising the polynucleotide sequence encoding the mutants. The vector may then be introduced into a host cell to allow expression of the mutants. Accordingly, embodiments herein include a host cell comprising the vector having polynucleotide strands encoding the mutants. In an embodiment, the vector comprises at least one polynucleotide strand having a sequence selected from a group consisting of SEQ ID NO: 6, SEQ ID NO: 7 and SEQ ID NO: 8. In an embodiment, the host cell comprises a polynucleotide encoding SEQ ID NO: 2. In an embodiment, the host cell comprises a polynucleotide set forth in SEQ ID NO: 6. In an embodiment, the host cell comprises a polynucleotide sequence encoding SEQ ID NO: 3. In an embodiment, the host cell comprises a polynucleotide set forth in SEQ ID NO: 7. In an embodiment, the host cell comprises a polynucleotide encoding SEQ ID NO: 4. In an embodiment, the host cell comprises a polynucleotide set forth in SEQ ID NO: 8. Various techniques for selecting and producing recombinant plasmids, host cells, etc. are generally known in the art which may be used in achieving the embodiments herein. In an embodiment, the method of producing the disclosed mutants include inducing mutation into a gene or polynucleotide sequence encoding an amino acid sequence set forth in SEQ ID NO: 1, or homologue thereof, at specific positions corresponding to 46$^{th}$ position and/or 53$^{rd}$ position of the amino acid sequence and introducing the mutated gene or polynucleotide sequence into a plasmid to obtain a recombinant plasmid; and expressing the mutant proteins.

In an embodiment, the method for synthesizing the mutant comprises substituting the amino acid at the 46$^{th}$ position and/or 53$^{rd}$ position, with Proline, or analog thereof, in the amino acid sequence of SEQ ID NO: 1. or an amino acid sequence having at least 70% identity to the sequence of SEQ ID NO: 1. In another embodiment, the method for synthesizing the mutant comprises transforming a host cell with the disclosed recombinant vector to obtain a recombinant strain, culturing the recombinant strain in a suitable culture medium to induce the expression of the mutant α-Syn, and purifying the expressed mutant from the culture medium. The expressed mutant proteins may then be cultured, isolated and purified by methods generally known in the art.

In an embodiment, the mutants are generated by using site-directed mutagenesis method.

Primer Designing: Primers for mutagenesis are designed such that mutation lay in the middle of the oligonucleotide with sufficient flanking residues (12-15 bases) to allow melting temperature (Tm) close to 78 degree C. GC content of all the primers is kept close to 50% for efficient PCR amplification. The following formula is used for the calculation of Tm:

$$Tm = 81.5 + 0.45(\% \; GC) - 675/N-\% \; mismatch$$
$$(Where \; N \; is \; the \; primer \; length)$$

Primer pairs are designed in such a way that they contain the desired mutation and anneal to the same sequence on opposite strands of the plasmid. In an embodiment, the primers are custom synthesized, for example by Sigma USA.

Site-directed mutagenesis: A two step-method wherein PCR and DpnI are used to perform site-directed mutagenesis. This method allows high-efficiency mutagenesis in a fairly short period. Rather than Taq DNA polymerase and Pfu polymerase, KOD Hot Start DNA polymerase (from Novagen®) is used to achieve high fidelity and fast extension.

```
E46P reverse strand primer:
5'GTAGGCTCCAAAACCAAGCCGGGAGTGGTGCATGGTG3'

A53P reverse strand primer:
5'GGAGTGGTGCATGGTGTGCCGACAGTGGCTGAGAAGAC
```

Mutant strand synthesis reaction: Polymerase chain reaction (PCR) is performed by using Applied Biosystems thermal cycler. Table 2 provides the condition for PCR where the total volume is 50 μl.

TABLE 2

| No. | Description | Quantity |
|---|---|---|
| | PCR Conditions | |
| 1 | Template DNA | 50 ng |
| 2 | Mutagenic sense (5') primer | 20 pmol |
| 3 | Mutagenic antisense (3') primer | 20 pmol |
| 4 | KOD Hot Start Buffer (10×) | 5 μl |
| 5 | 25 mM MgSO4 | 3 μl |
| 6 | dNTPs (2 Mm each) | 5 μl |
| 7 | KOD Hot Start DNA polymerase | 1 U |

A negative control (all component of PCR reaction is added except KOD Hot Start Polymerase) is kept along with sample PCR reaction (5% ethylene glycol is used in the case of primers showing the strong propensity of secondary structure). Table 3 provides the thermal cycling parameter.

TABLE 3

| | Thermal cycling parameter | |
|---|---|---|
| No. | Description | Quantity |
| 1 | Thermal cycling parameter | 3 minutes |
| 2 | Denaturation (94° C.) | 2 minutes |
| 3 | Primer annealing (60° C.) | 30 seconds |
| 4 | Reaction extension (70° C.) | 90 seconds |
| 5 | Final extension (70° C.) | 10 minutes |

The mutated plasmid containing staggered nicks is generated by extension of primers annealed to opposite strand of the denatured plasmid by temperature cycling.

DpnI digestion of amplification product: Contamination of original template non-mutated DNA is removed by digestion of original methylated and hemimethylated with DpnI restriction enzyme. DpnI restriction digestion removes the template DNA, leaving intact the newly synthesized double-stranded mutant PCR product.

Transformation of PCR product in *E. coli* XLI: Polymerase chain reaction leads to incorporation of mutated oligonucleotide mismatched primers that generate a mutated circular nicked plasmid containing staggered nicks. To repair the nicks the DpnI digested PCR product is transformed to *E. coli* XL1 competent cells. *E. coli* cells can self-ligate the transformed nicked plasmid by their DNA repair.

Mutant plasmid mini preparation and sequence confirmation: Transformants are randomly selected from LB-ampicillin agar plate and inoculated in 5 ml LB-ampicillin overnight at 37 degrees C., 225 rpm. Plasmid preparation (mini prep) is done by using a Qiagen miniprep kit according to the manufacturer's instructions. Plasmid DNA is sequenced to confirm the desired mutation.

The invention is further described by reference to the following examples by way of illustration only and should not be construed to limit the scope of the embodiments disclosed herein. It will be apparent to those skilled in the art that many modifications, both to materials and methods, may be practiced without departing from the scope of the claimed embodiments.

Example 1

Expression and Purification of Protein

Expression and purification of α-Syn and mutant protein A30P, E46P, and A53P were carried in *E.coli* BL21(DE3) cells according to the standard protocol by Volles et al with some modification. In brief, transformed *E.coli* BL21 (DE3) cells were grown in Luria Broth (by HiMedia Laboratories) at 37 degrees C. with continuous shaking at 200 r.p.m. Cells were induced using 1 mM IPTG when cell optical density at 600 reached 0.8 under identical conditions. The induced cells were pelleted and pellet redissolved in the buffer (50 mM tris, pH 8.0, 10 mM EDTA, and 150 mM NaCl) with protease inhibitor cocktail (Roche applied sciences, USA). The cells were sonicated followed by heating in a boiling water bath at 95 degrees C. for 20 min. After centrifugation (12000 g, 45 min) 10% streptomycin sulfate (136 μl/ml of supernatant) and glacial acetic acid (228 μl/ml of supernatant) were added to the supernatant and incubated for 30 min at 4 degree C. The solution was centrifuged at 12000 g for 45 min and an equal volume of saturated ammonium sulfate was added to the supernatant to precipitate the protein. The precipitated solution was centrifuged at 12000 g for 45 min and the pellet was washed with ammonium sulfate (1:1 V/V saturated ammonium sulfate and water). The washed pellet was resuspended in 100 mM ammonium acetate and precipitated using absolute ethanol. This step was repeated twice. Finally, pelleted protein redissolved in 100 mM ammonium acetate and lyophilized. The lyophilized protein was stored at −20 degree C. for further use.

The embodiments herein include a substrate for detection of α-Syn in a sample. The term "sample" or "biological sample" as used herein includes any material, including synthetic or biological material having biomolecules. It includes samples having or suspected of having α-Syn, including its monomeric, oligomeric, amyloid structure, fibrillar form and/or aggregate forms; wildtype, folded, unfolded and/or misfolded forms of α-Syn; pathological or synthetic seed of α-Syn. It includes samples from mammals having or suspected of having synucleinopathies. It further includes biological samples such as tissue samples; blood sample, whole blood, plasma or serum; bodily fluids; saliva; cerebrospinal fluid (CSF) etc. In an embodiment, the sample includes any sample that is generally used in detection of synucleinopathies. Further, the sample may include samples obtained from any subject including mammals, particularly humans. In an embodiment, the sample is blood serum obtained from a subject. In another embodiment, sample is whole blood sample obtained from a subject.

The sample may further be processed or unprocessed. In an embodiment, the sample is whole blood collected from patients in EDTA free tubes. After collection of the blood, the blood may be allowed to clot by leaving it undisturbed at room temperature for 15 to 30 minutes, and serum separated according to generally known techniques. In an embodiment, the clot is removed by centrifuging samples at 2500 rpm for about 10 min at about 4 degree Celsius to obtain serum which may optionally be stored at −80 degree Celsius. In some embodiments, sample may further be treated with glycine-NaOH buffer, and sodium azide. In an embodiment, the serum sample is treated with glycine-NaOH buffer (preferably pH 7.4), and about 0.01% of sodium azide.

The mutants, according to embodiments herein, may be used as substrate in known amplification techniques; for example, to multiply and/or detect misfolded prions. Examples of such techniques include protein misfolding cyclic amplification (PMCA), real time-quaking induced conversion (RT-QuIC) and HANdai Amyloid Burst Inducer (HANABI). PMCA is an amplification technique to multiply misfolded prions. Refer Claudio Soto, et al, *Cyclic amplification of protein misfolding: application to prion-related disorders and beyond; Trends in Neurosciences* vol 25,390-394,2002, which is incorporated herein by reference.

RT-QuIC is a technique which exploits the ability of $PrP^{Sc}$ to induce $PrP^{C}$ to misfold, to form aggregates of $PrP^{Sc}$ fibrils, in detecting small amounts of $PrP^{Sc}$. Refer: Ryuichiro Atarashi et al; *Ultrasensitive human prion detection in cerebrospinal fluid by real-time quaking induced conversion; Nature medicine*, Vol 17 (2): 175-178, 2011, which is incorporated herein by reference.

HANABI is an automatic and rapid technique for analysis of fibrillation of proteins. The technique mainly involves sonication and incubation cycle with real-time monitoring of a fluorescent signal. Refer: Ayaka Umemoto, et al; *High-throughput analysis of ultrasonication-forced amyloid fibrillation reveals the mechanism underlying the large fluctuation in the lag time; The Journal of Biological Chemistry*, Vol: 289(38): 27290-27299, 2014; which is incorporated herein by reference.

In an embodiment, the mutants are mixed with samples and subjected to one or more incubation and sonication cycles leading to amplification of pathological prion aggregates which may further be detected by generally known screening methods for e.g.: by biochemical assays such as Thioflavin fluorescence assay, western blot, dot blot, immunoassays, immunostaining, enzyme-linked immunosorbent assay (ELISA), etc.

The embodiments herein also include a substrate for detection of synucleoinpathies. The presence of α-Syn aggregates in biological samples is generally indicative of many neurodegenerative diseases. Abnormal α-Syn tends to form aggregates which are understood to be involved in synucleinopathies. Synucleinopathies include, but not limited to, neurodegenerative disorders such as Parkinson's disease, dementia with Lewy bodies, Lewy body variant of Alzheimer disease (LBV), multiple system atrophy, autonomic dysfunction and neurodegeneration. In an embodiment, the substrate for detection comprises the α-Syn mutants, or species thereof. In another embodiment, the substrate comprises α-Syn mutants, or species thereof, and a suitable detectable agent. Various detectable agents are generally known in the field and may be instrumental in the embodiments herein. Generally known detectable agents include enzyme, fluorescent labels/dyes, gold labels, radiolabels, aptamers, etc; which may be tailored based on the screening methods.

Embodiments herein include an invitro aggregation assay for evaluating the presence and/or quantity of α-Syn in a sample. Methods for detection of α-Syn are disclosed herein. Further, embodiments herein include a method for detection of synucleinopathies in an individual. Also disclosed is an invitro aggregation assay kit. In an embodiment, the kit comprises at least one of the disclosed mutants. In another embodiment, the kit comprises at least one receptacle for receiving said sample; at least one of the disclosed mutants as substrate for seed-mediated amplification of α-Syn; and an instruction manual for performing the assay. In another embodiment, the kit comprises at least one receptacle for receiving said sample; at least one of the disclosed mutants as substrate for seed-mediated amplification of α-Syn; and an instruction manual for performing the assay. In an embodiment, the kit is a congo red dot test kit comprising congo red dye. The kit may further comprise other components such as one or more reaction papers, syringes, etc. In an embodiment, the receptacle is a nitrocellulose reaction paper. In an embodiment, the kit comprises at least one receptacle for receiving the sample; at least one of the disclosed mutants as substrate for seed-mediated amplification of α-Syn; suitable amount of Congo red dye; and an instruction manual for performing the assay. The amount of Congo red dye may be suitably varied such that it is sufficient to achieve staining and visual identification of misfolded proteins in sample. Embodiments may include varied volumes, depending on the number of tests intended to be performed per kit. In an embodiment, the kit is a point of care test kit to detect synucleinopathies in an individual, comprising at least one receptacle for receiving the sample; at least one of the disclosed mutants as substrate for seed-mediated amplification of α-Syn; suitable amount of Congo red dye for detection of amplified α-Syn aggregates; and an instruction manual for performing the assay. In an embodiment, concentration of congo red dye is in the range of 4 to 5 mg/mL. In an embodiment, the volume of congo red dye is in the range of 0.5 to 2.5 μL. The mutant, in an embodiment, is a wild type α-Syn having at least one amino acid substitution mutation selected from a group consisting of E46P and A53P. In an embodiment, the mutant is E46P mutant of α-Syn. In another embodiment, the mutant is A53P of α-Syn.

The method of detection, according to embodiments herein includes use of the disclosed mutants. The non-self-aggregating nature of the disclosed mutants enables accurate, efficient and early detection of synucleinopathies. In an embodiment, the method includes obtaining a sample; and mixing at least one mutant with the samples and incubating. Incubation is performed under conditions that allow α-Syn aggregate formation. Incubation step further comprises agitation and centrifugation to obtain a pellet comprising α-Syn aggregates. The sample may further comprise pre-formed α-Syn seed. In an embodiment, the sample is serum sample obtained from an individual. In another embodiment, the sample is a sample spiked with predetermined level of α-Syn seed. In an embodiment, the sample comprises a suitable or pre-determined level of α-Syn seed. Suitable α-Syn seeds include, but are not limited to, α-Syn oligomer, α-Syn monomer, α-Syn fibril, pre-formed synthetic seed, misfolded α-Syn, and pathological prion.

In an embodiment, the method of detection includes obtaining said sample; incubating at least one of the disclosed mutants with said sample to facilitate formation and/or amplification of α-Syn aggregates; detecting the α-Syn aggregates using suitable methods. In an embodiment, the method of detection includes obtaining said sample; incubating at least one of the disclosed mutants with said sample; centrifuging the incubated sample to obtain pellets; and detecting α-Syn aggregates in said pellet using suitable methods. In an embodiment, the method includes obtaining said sample; subjecting to at least one technique selected from a group consisting of protein misfolding cyclic amplification (PMCA), real time-quaking induced conversion (RT-QuIC) assay and HANdai Amyloid Burst Inducer (HANABI) using at least one of the disclosed mutants as substrate; and detecting α-Syn aggregates using suitable methods. In an embodiment, the sample is subjected to PMCA assay to obtain amplified α-Syn aggregates. The sample may be subjected to one or more cycles of amplification. In some embodiment, a plurality of PMCA cycles are performed. In an embodiment, incubation is performed under conditions that allow α-Syn aggregate formation. Incubation may include one or more cycles of incubation and agitation (eg: sonication). The cycles and incubation parameters may be tailored as known to a person skilled in the art. In an embodiment, incubation is performed for about 1 to 140 hr at about 37 degrees C. and agitation is by bath sonication. In an embodiment, the cycles include 4 to 6 hrs, preferably 6 hours, incubation at 32 to 37 degrees C., preferably 37 degrees Celsius, followed by bath sonication of 10 to 15 min, preferably 15, for initial 8 cycles, and another 16 cycles of 2 to 3 hr, preferably 3 hrs, incubation, followed by 10 to 15 min, preferably 15 min, bath sonication at about 37 to 40 degrees C. In an embodiment, incubation is performed for four rounds of 24 cycles each, wherein amplification of pathological aggregates is observed after completion of each round.

Suitable methods of detecting amplified α-Syn aggregates include conventional methods such as Thioflavin fluorescence assay, western blot, dot blot, immunoassays, immunostaining, enzyme-linked immunosorbent assay (ELISA), etc. In some embodiments, the method includes any one suitable detection method selected from the group consisting of Thioflavin fluorescence assay, western blot, dot blot, immunoassays, dye test, immunostaining and enzyme-linked immunosorbent assay (ELISA). In a preferred embodiment, the method includes detecting amplified α-Syn aggregate using congo red dot (CRD) test. The present method, wherein detection is by CRD test, is an improved and convenient method for detection of the amplified misfolded product and high throughput screening. Congo red is an azo dye having affinity towards filamentous protein aggregates and is generally used in diagnostics. It is understood that similar dyes capable of binding to protein aggregates may be used in various embodiments.

In another embodiment, the method includes detecting α-Syn aggregate by Thioflavin (ThT) fluorescence assay. In yet another embodiment, the method includes detecting α-Syn aggregate by Western blotting technique.

In an embodiment, incubation may be performed in the presence of pre-determined concentration of α-Syn seeds. Further, glycine-NaOH buffer, and sodium azide may be used in preparation of sample. Suitable amounts and concentrations of glycine-sodium hydroxide buffer and sodium azide may be used. In an embodiment, the concentration of glycine-sodium hydroxide buffer is about 20 mM of about pH 7.4. In an embodiment, the sodium azide used is 0.01% sodium azide solution. In an embodiment, the sample is prepared in glycine-NaOH buffer (preferably pH 7.4), and about 0.01% of sodium azide. Further, the ratios of the sample and mutant may be suitably adjusted. In an embodiment, the sample to mutant ratio is in the range of 1:0.5 to 1:4.

In an embodiment, the method comprises obtaining said sample; subjecting said sample to one or more rounds of protein misfolding cyclic amplification (PMCA) using at least one of the disclosed mutants as substrate, to obtain amplified α-Syn aggregates; and detecting α-Syn aggregates using congo red dot test. In an embodiment, the sample is subjected to 2 to 4 rounds of PMCA cycles.

In an embodiment, the method comprises obtaining a sample from said individual; mixing said sample with at least one of the disclosed mutants to obtain a reaction mixture; incubating the reaction mixture to obtain amplified pathological α-Syn aggregates; mixing said amplified pathological aggregates and congo red dye, and incubating; placing the mixture on suitable reaction paper; and detecting based on retention of said congo red dye on the paper; and determining presence or absence of Synucleinopathy in said individual.

In an embodiment, the method comprises obtaining said sample; mixing said sample with at least one of the disclosed mutants, glycine-sodium hydroxide buffer, and sodium azide solution to obtain a reaction mixture; subjecting said reaction mixture to cyclic amplification to obtain amplified product or pathological aggregates; mixing said amplified product and congo red dye; incubating; and detecting presence of amplified product in sample using a reaction paper, eg: nitrocellulose paper. The reaction paper is washed with increasing concentrations of ethanol (eg: 50%, 70% and 90%) till the red color of the blank sample disappeared completely. Disappearance of the red color is indicative of absence of misfolded protein, whereas retention of a visibly red color is indicative of the presence of misfolded protein. Color intensities may further be measured by known techniques.

In an embodiment, cyclic amplification comprises subjecting said reaction mixture to first round of incubation and sonication, wherein said incubation is performed for about 4 to 6 hours and bath sonication for about 10 to 15 mins, at about 32 to 37 degrees Celsius; and second round of incubation and sonication, wherein said incubation is performed for about 2 to 3 hours at about 32 to 37 degrees Celsius and bath sonication for about 10 to 15 mins Each of first and second round of incubation and sonication may further be suitably repeated to achieve amplification. In an embodiment, the first round of incubation and sonication is performed for 8 cycles. In an embodiment, the second round of incubation and sonication is performed for 16 cycles. Further, the 8 cycles of first incubation and sonication and 16 cycles of second of incubation and sonication may be repeated one or more times. In an embodiment, the 24 cycles of incubation and sonication is repeated four times or up to four rounds. In an embodiment, It is understood that specific details regarding parameters, material and methods, as described herein, are not to be interpreted as limiting. It is also understood that various modifications and alterations to the same would be apparent to a person skilled in the art, in light of the disclosures herein, without departing from the scope and spirit of the present invention.

In-Vitro Aggregation Study of Wild Type (WT), A30P α-Syn, E46P α-Syn, and A53P α-Syn.

Protein aggregation into amyloid fibril was studied using biophysical techniques such as Thioflavin T (ThT) binding and circular dichroism (CD). To study the effect of proline mutation on aggregation propensity of α-Synat 46$^{th}$ and 53$^{rd}$ positions, A53P and E46P plasmid constructs were made using site-directed mutagenesis using WT plasmid. WT, and both designed mutants were expressed and purified from *E. coli* according to established protocol. All the proteins were studied for aggregation assay after preparing low molecular weight (LMW) protein in 20 mM Gly-NaOH buffer, pH 7.4, 0.01% sodium azide with 300 μM concentration. The protein aggregation was monitored using Thioflavin T (ThT) and circular dichroism (CD) spectroscopy. The ThT binding assay of α-Syn showed a traditional sigmoid binding curve for WT and mutants. FIG. 1(a) is a graph of ThT binding assay results showing increased binding for WT and A30P with time and no ThT fluorescence for E46P and A53P. WT and A30P formed amyloid after the lag time, where significant ThT binding was observed. The lag time was calculated using the established method. The lag time of WT was found to be ~48 hr and ~100 hr for A30P. However, A53P and E46P did not show increased ThT binding up to 300 hr of incubation as compared to WT. The binding data suggest that proline mutation at 53$^{rd}$ and 46$^{th}$ positions halted the aggregation of α-Syn. The secondary structural transitions of protein during aggregation were measured using CD spectroscopy. WT and A30P showed a structural transition to β-sheet structure at 84 h and 180 h respectively. Interestingly both A53P and E46P did not form β-sheet structure and remain in random coil state. The morphology of the end product of aggregation was studied using TEM (transmission electron microscopy). The data suggest that WT and A30P formed amyloid fibrils at the end of aggregation. However, both A53P and E46P did not show any fibril rather showed a small globular oligomeric structure, which could be due to the monomer or low order oligomers. FIGS. 1(b) to 1(e) are TEM images; wherein 1(b) and 1(c) are WT and A30P showing fibrillar morphology, whereas 1(d) and 1(e) are E46P and A53P showing globular and granular morphology, respectively.

Co-Aggregation and Seeding of E46P and A53P with WT α-Syn.

Figure 2A:
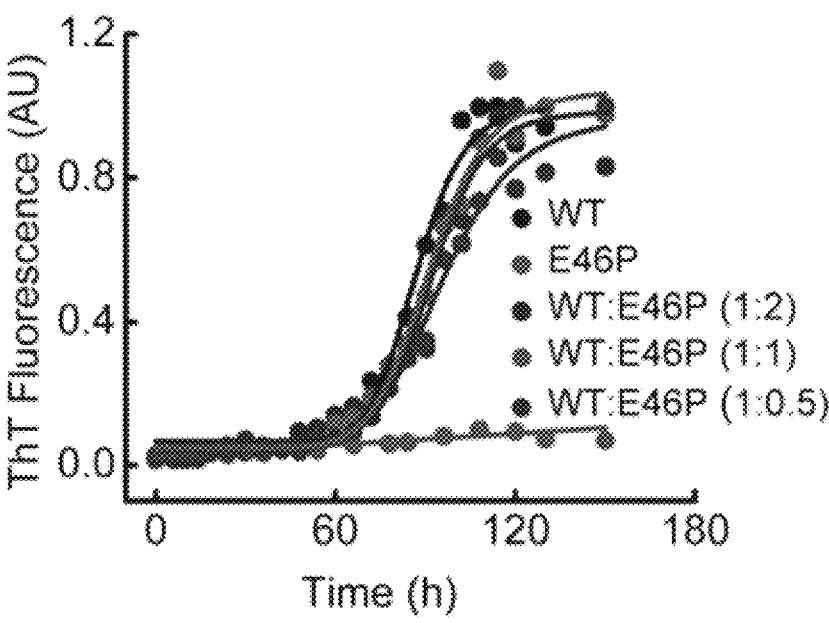
FIGS. 2(*a*) and 2(*b*) are graph depicting ThT fluorescence of mutants showing co-aggregation with varying concentrations of WT; wherein 2(*a*) depicts E46P, and 2(*b*) depicts A53P mutants, respectively.
Figure 2B:
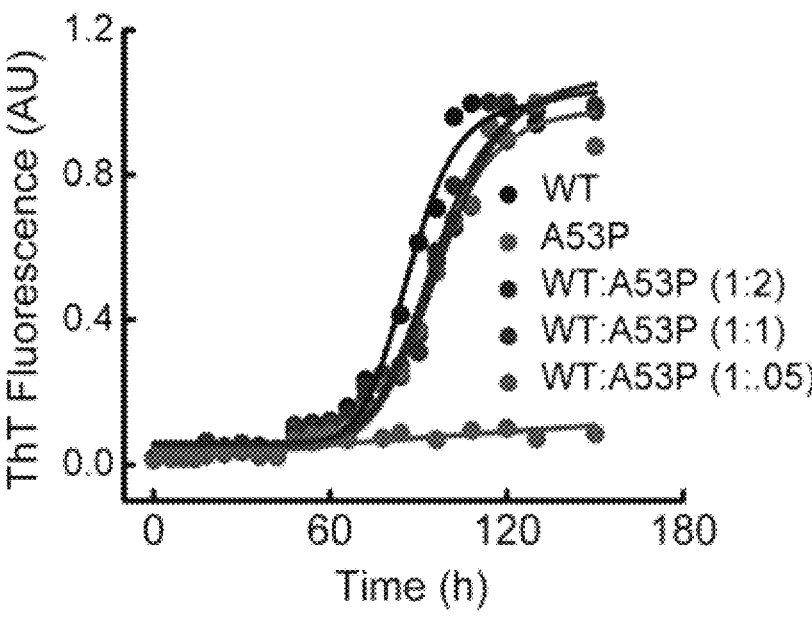
Figure 3A:
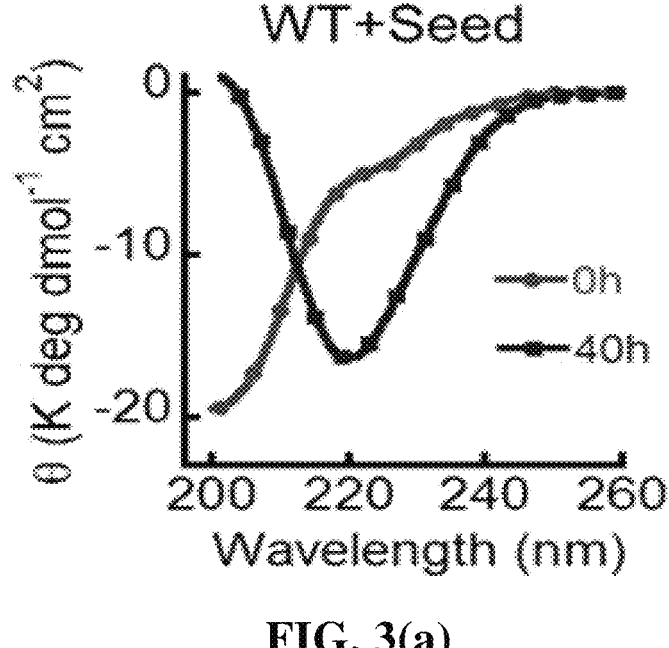
FIGS. 3(*a*) to 3(*d*)are graphs showing influence of seeding on secondary structure of mutants with WT seeds; wherein 3(*a*) depicts WT incubated with WT seeds, 3(*b*) depicts A30P with WT seeds, 3(*c*) depicts E46P with WT seeds, 3(*d*) depicts A53P with WT seeds, while 3(*e*) is a graph depicting ThT binding assay in presence of 1% WT seed.
Figure 3B:
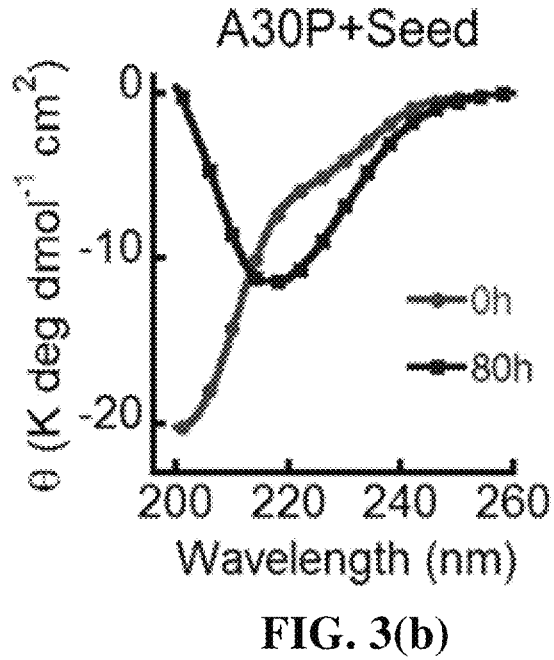
Figure 3C:
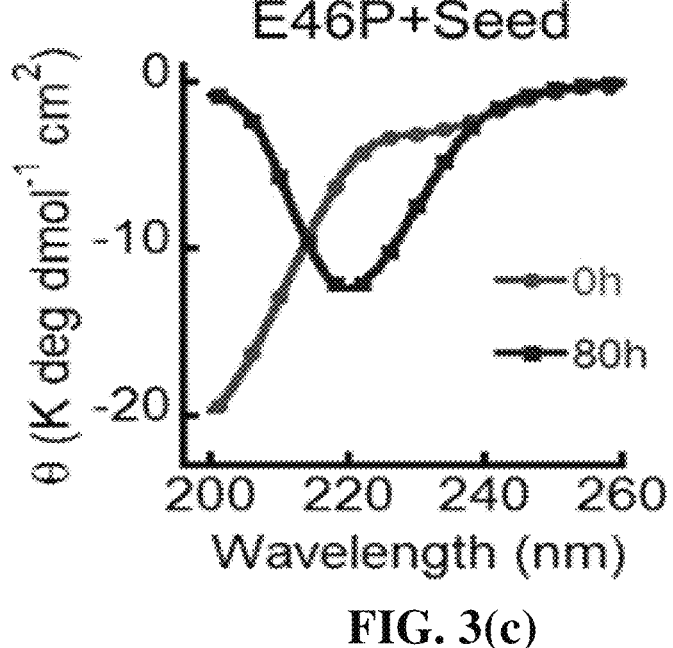
Figure 3D:
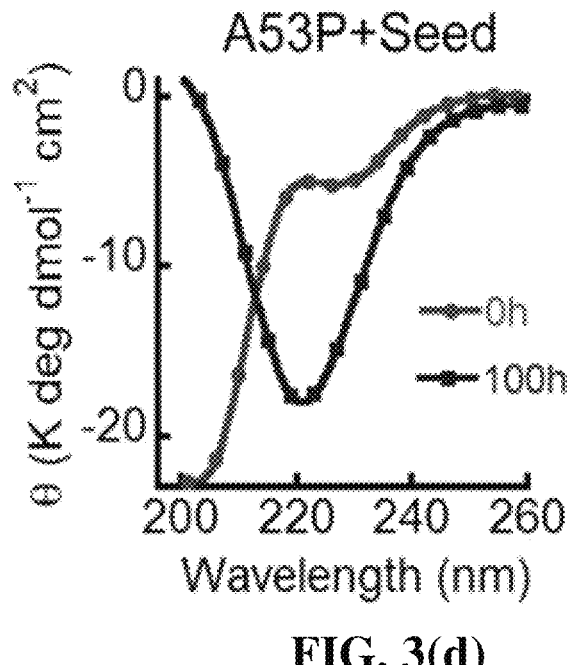
Figure 3E:
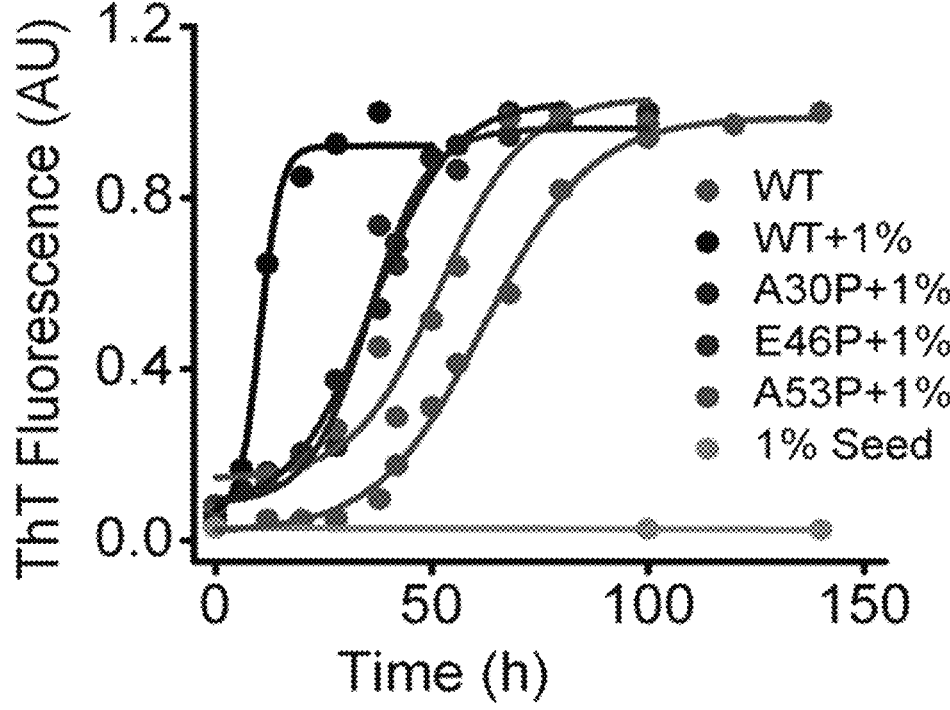

Since E46P and A53P protein did not form amyloid structures, co-aggregation study with WT and proline mutated proteins, with 1:0.5, 1:1, and 1:2 ratios, was performed to check if WT could influence aggregation potential of mutants. Intestinally, both mutants aggregated to amyloid as confirmed by ThT binding. All the ratios of WT and Proline mutants showed similar aggregation kinetics as that of WT alone. In the presence of WT α-Syn, both proline mutants efficiently incorporated into fibril formation. FIGS. 2(a) and 2(b) are graph depicting ThT fluorescence of mutants showing co-aggregation with varying concentrations of WT; wherein 2(a) depicts E46P, and 2(b) depicts A53P mutants, respectively. It is speculated that the primary nucleation of aggregation is done by WT protein after which mutated protein engages in elongation of fibrils and resulting in the mixed fibrils (WT+mutant fibrils) along with WT fibrils. To test this, 1% sonicated WT seeds were added to monomers of both proline mutants, and aggregation kinetics was done using ThT assay. FIGS. 3(a) to 3(d) are graphs showing influence of seeding on secondary structure of mutants with WT seeds; wherein 3(a) depicts WT incubated with WT seeds, 3(b) depicts A30P with WT seeds, 3(c) depicts E46P with WT seeds, 3(d) depicts A53P with WT seeds, while 3(e) is a graph depicting ThT binding assay in presence of 1% WT seed. FIGS. 4(a) to 4(d) are TEM images showing morphology of aggregates at end of seeding; wherein 4(a) depicts WT incubated with WT seeds, 4(b) depicts A30P with WT seeds, 4(c) depicts E46P with WT seeds, and 4(d) depicts A53P with WT seeds, respectively.

Figure 5:
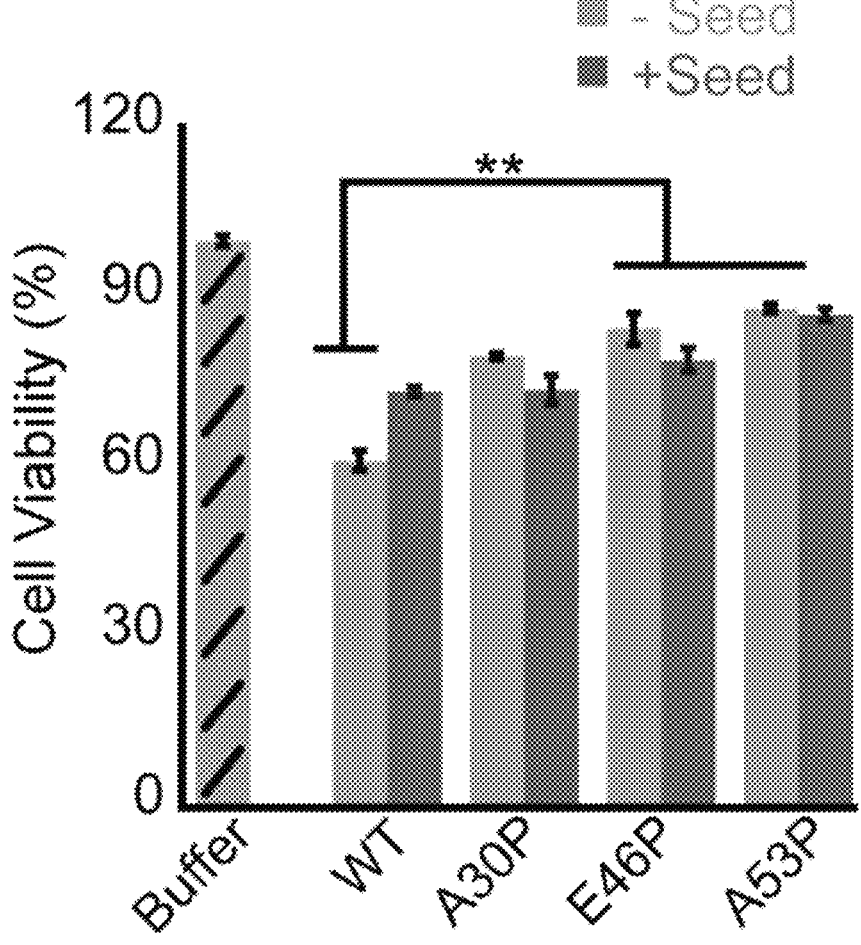
FIG. 5 is a graph depicting the results of MTT based cell toxicity assay for WT, A30P, E46P, A53P with and without seed.

The result showed all the mixture converted to β-sheet structure and formed amyloid fibril. Further, the toxicity of these fibrils was checked using an MTT assay. The toxicity data suggest that both of the non-self-aggregating mutants have less toxicity as compared to WT fibrils. FIG. 5 is a graph depicting the results of MTT based cell toxicity assay for WT, A30P, E46P, A53P with and without seed.

Determination of Minimum Concentration of WT Fibril to Seed E46P Aggregation.

Figure 6A:
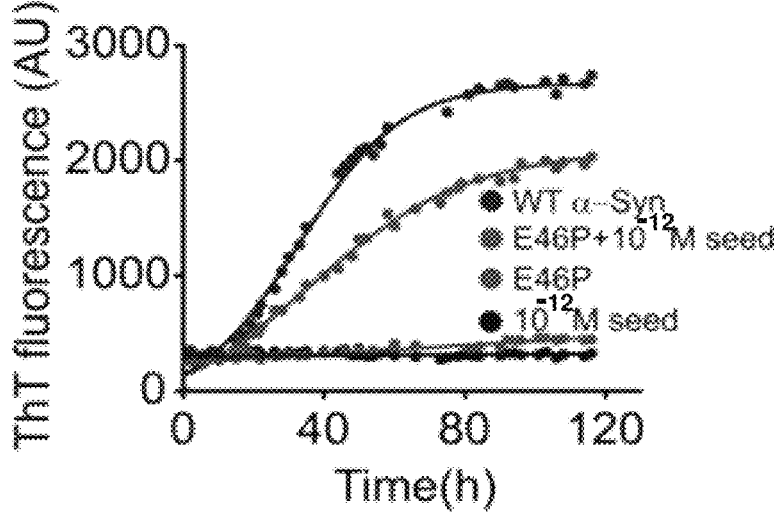
FIGS. 6(*a*) and 6(*b*) are graphs depicting the aggregation of E46P by ThT fluorescence assay; wherein 6(*a*) depicts E46P with picomolar, and 6(*b*) depicts E46P with femtomolar, WT seed respectively.
Figure 6B:
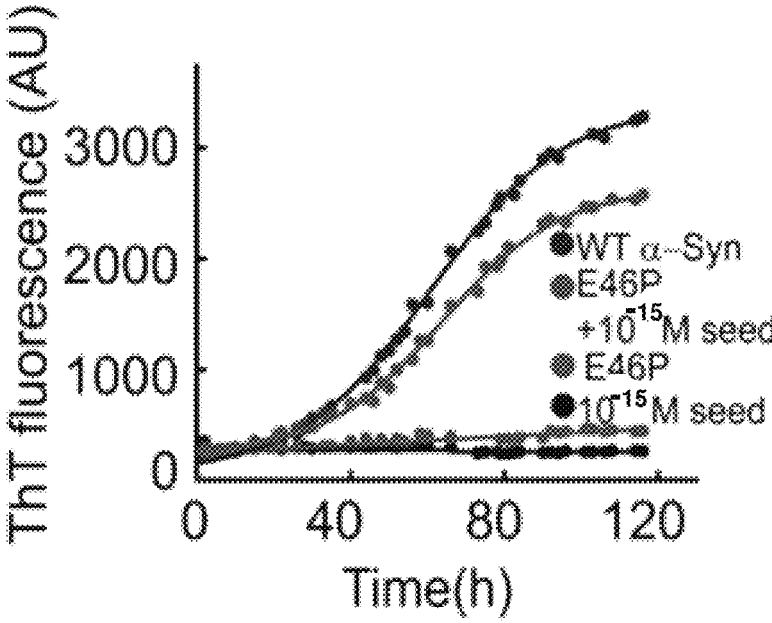
Figures 7A, 7B, 7C:
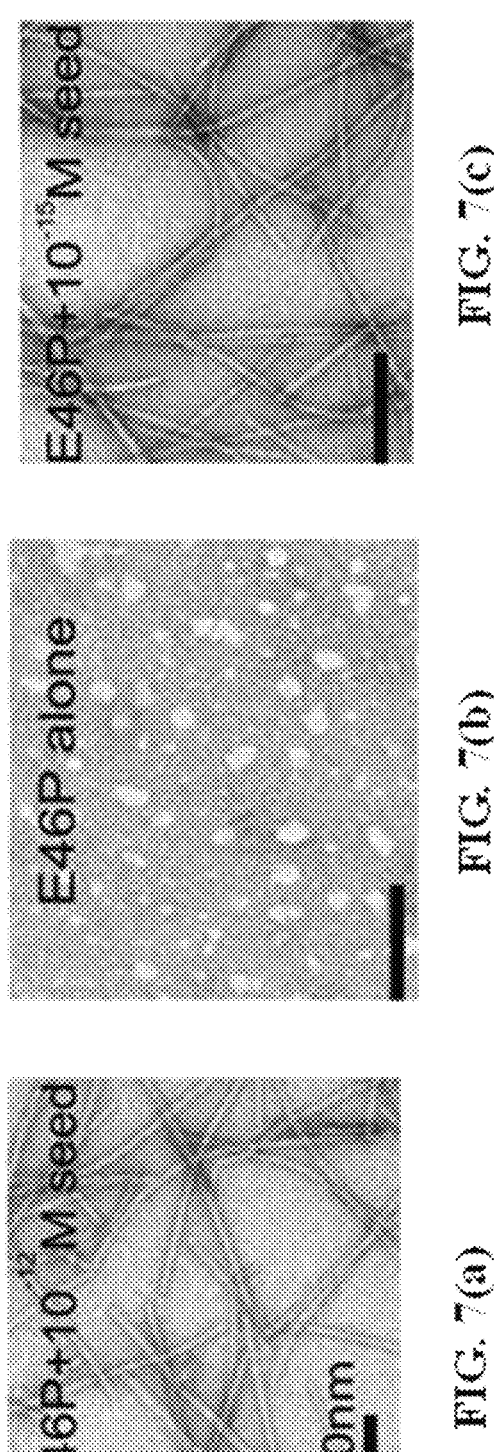
FIGS. 7(*a*) to 7(*c*) are TEM images showing morphological changes in E46P protein; wherein 7(*a*) depicts E46P with picomolar seed; 7(*b*) depicts E46P without seed; 7(*c*) depicts E46P with femtomolar seed concentration respectively.

Since the E46P and A53P mutant protein does not aggregate alone and aggregates in presence of seeds of WT protein at higher concentration (1% V/V). The ability of these mutant proteins to get aggregates at a lower concentration of seeds that would mimic the concentration of seed present in the biological fluid of synucleinopathies patients, was checked. To test this, sonicated fibril seeds at picomolar and femtomolar concentration were added to the monomers of both proline mutants and WT α-Syn. The proline mutant and WT α-Syn protein alone were kept as a control. Seed prepared invitro from purified human α-Syn fibrils were used. The seeds were generated by sonicating the wild type fibrils to produce small fibril fragmented seeds. Fibrils were sonicated at 20% amplitude with 3 sec on and 1 sec off pulse for 3 min. The generated seeds were used for further studies. Picomolar ($10^{-12}$ M) and femtomolar ($10^{-15}$ M) seeds were incubated with E46P and A53P monomer. The aggregation kinetics were studied using ThT fluorescence assay and structural transition observed using circular dichroism spectroscopy. The results showed an increase in ThT fluorescence of E46P mutant protein even in presence of low concentration picomolar ($10^{-12}$ M) and femtomolar ($10^{-15}$ M) of seed concentration. FIGS. 6(a) and 6(b) are graphs depicting the aggregation of E46P by ThT fluorescence assay; wherein 6(a) depicts E46P with picomolar and 6(b) depicts E46P with femtomolar WT seed, respectively. FIGS. 7(a) to 7(c) are TEM images showing morphological changes in E46P protein; wherein 7(a) depicts E46P with picomolar seed; 7(b) depicts E46P without seed; 7(c) depicts E46P with femtomolar seed concentration, respectively. All the mixture of E46P protein in presence of seed converted into the β-sheet structure and form amyloid fibrils. However, E46P alone did not show an increase in ThT binding up to 120 hrs of incubation (FIGS. 6(a) and 6(b)). E46P alone did not show structural transition and remained in a random coil state and did not show any amyloid fibril morphology at the end of aggregation (FIG. 7(b)).

Seeding of E46P Mutant with WT α-Syn Oligomer

Figure 8:
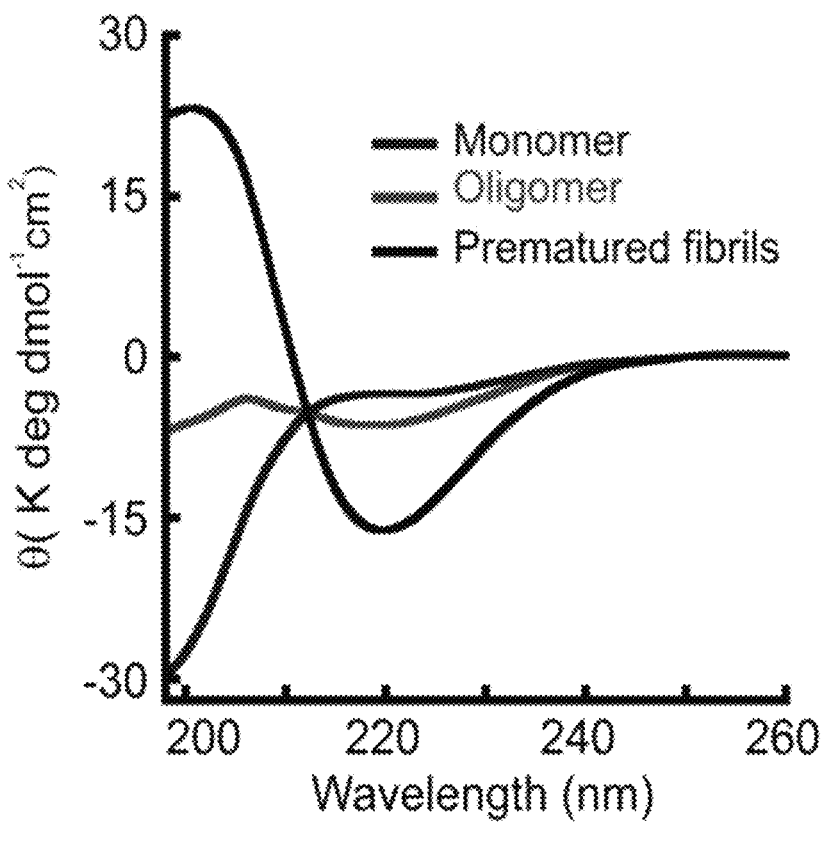
FIG. 8 is a graph depicting CD spectra showing secondary structure of WT α-Syn monomer, oligomer, and fibril.
Figure 9C:
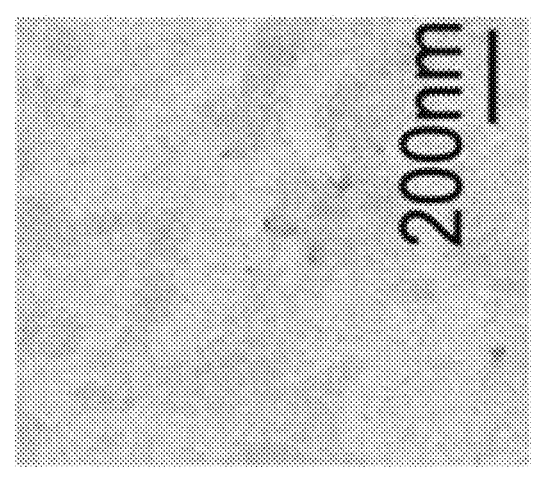
FIGS. 9(*a*) to 9(*c*) are TEM images depicting different morphological forms of WT protein; wherein 9(*a*) depicts premature fibrils of WT; 9(*b*) depicts WT oligomer, and 9(*c*) depicts WT monomer, respectively.
Figure 9C:
Figure 9B:
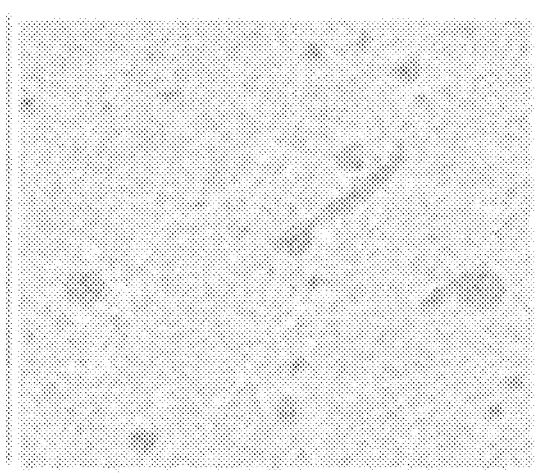
Figure 9A:
Figures 9D, 9E, 9F, 9G:
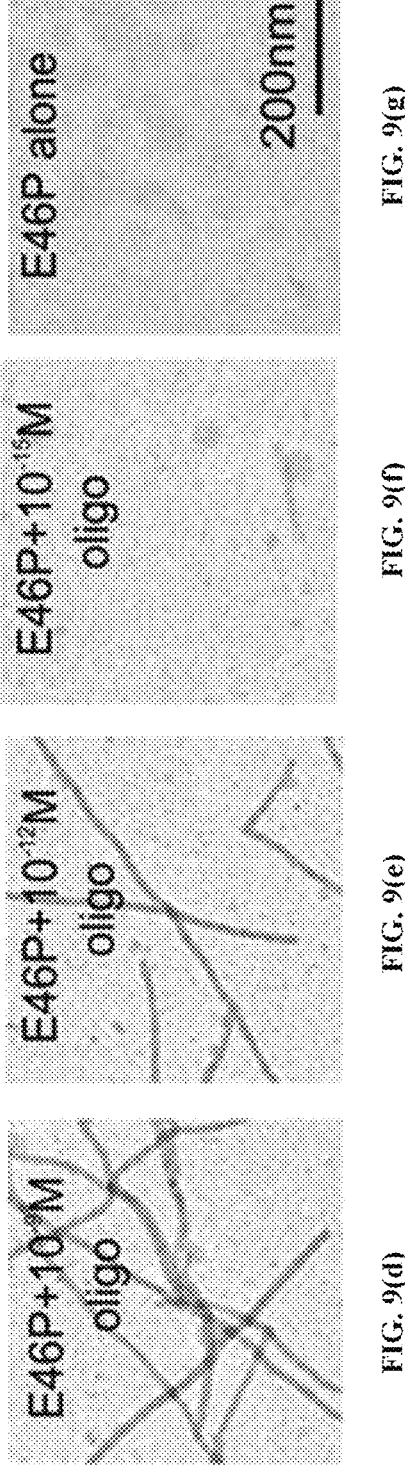
Figure 10:
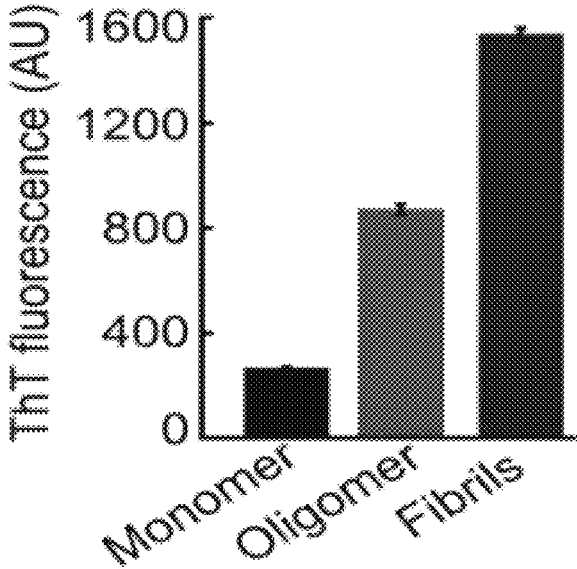
FIG. 10 is a graph depicting ThT fluorescence assay results of WT monomer, oligomer, and fibril.
Figure 11:
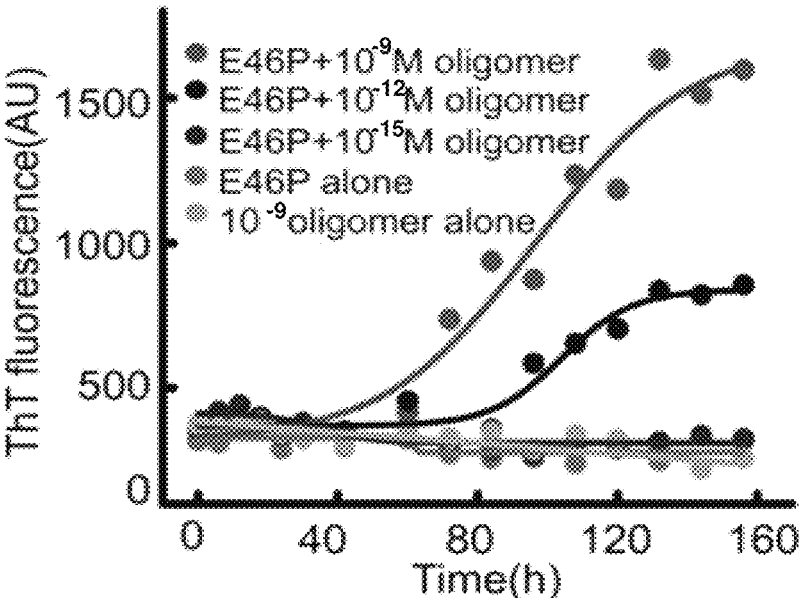
FIG. 11 is a graph depicting ThT fluorescence assay results showing aggregation of E46P in presence of different concentrations of WT oligomer.

The oligomerization of α-Syn precedes fibrillar aggregates. There are substantial studies that suggest that the mechanism of α-Syn aggregation includes conversion of soluble α-Syn monomer to soluble misfolded oligomers, to an aggregated insoluble form. It is the key event in the pathogenesis of PD and other synucleinopathies. The studies suggest that the oligomeric population of α-Syn is increased in blood as compared to monomer in PD patients. The mutants were tested to detect the oligomeric aggregates in biological fluids. Thus, further we studied the seeding of E46P mutant with WT α-Syn oligomer. Here, the influence of oligomers on aggregation of E46P mutant at lower concentrations was investigated, so that it will be helpful for early diagnosis of PD and other parkinsonian disorders. For this, invitro oligomers of recombinant α-Syn were synthesized using a method by Ghosh et al. The α-Syn species produced during aggregation kinetics over the time were monitored using circular dichroism, ThT fluorescence assay, and transmission electron microscope respectively. After 48 hr of incubation, the sample mixture was centrifuged to separate premature fibrils (PMF) as a pellet and the supernatant containing oligomers and monomers. The supernatant was passed through a 100 kDa cut-off membrane to separate oligomers (retentate) and monomer (flowthrough). All three fractionate monomers, oligomers, and premature fibrils were analyzed individually. The pelleted fraction predominantly showed a β-sheet conformation in the CD spectrum while retentate showed alpha-helical structure whereas monomeric fraction showed random coiled structure. FIG. 8 is a graph depicting CD spectra showing secondary structure of WT α-Syn monomer, oligomer, and fibril. The graph particularly shows secondary structure of WT monomer, oligomer, and fibril measured using CD. All three different fractions were further characterized by transmission electron microscopy for their morphology. The pelleted fraction showed fibrillar morphology whereas retentate showed oligomeric lower-order assemblies and thin protofilaments-like structure. The amorphous structure was observed for a monomeric fraction (flow-through). FIGS. 9(a) to 9(c) are TEM images depicting different morphological forms of WT protein; wherein 9(a) depicts premature fibrils of WT; 9(b) depicts WT oligomer, and 9(c) depicts WT monomer. FIGS. 9(d) to 9(g) are TEM images depicting morphological changes in E46P protein with or without WT oligomer after aggregation kinetics; wherein 9(d) depicts E46P with $10^{-9}$ M WT oligomer; 9(e) depicts E46P with $10^{-12}$ M WT oligomer; 9(f) depicts E46P with $10^{-15}$ M WT oligomer, and 9(g) depicts E46 alone, respectively. Further, the ThT binding assay showed the highest ThT fluorescence for preformed fibrils compared to oligomer and least binding for a monomeric fraction. FIG. 10 is a graph depicting ThT fluorescence assay results of WT monomer, oligomer, and fibril. To test the oligomer efficiency to seed aggregation of E46P mutant protein, oligomeric seeds at a concentration of nanomolar ($10^{-9}$ M), picomolar ($10^{-12}$ M), and femtomolar ($10^{-15}$ M) range were added to 200 μM E46P protein. 200 μM E46P protein alone was used as a control. Further, the kinetics of E46P α-Syn aggregation was monitored using ThT fluorescence assay. The data suggests that as little as picomolar oligomers seed can induce E46P aggregation. Slower aggregation kinetics was observed in presence of picomolar seeds compare to nanomolar. There was no significant ThT binding in the presence of femtomolar seed and E46P protein alone up to 160 h of incubation. This could be due to a very low concentration of seed may not induce the aggregation of E46P or it may induce the aggregation after a longer incubation period. FIG. 11 is a graph depicting ThT fluorescence assay results showing aggregation of E46P in presence of different concentrations of WT oligomer. Further, the morphological changes in E46P protein induced by oligomers were studied using TEM. The data suggests that E46P protein formed amyloid fibrils at the end of aggregation in the presence of nanomolar ($10^{-9}$ M) and picomolar ($10^{-12}$ M) seeds. We monitored the secondary structure transition of the protein in presence of oligomeric seed using CD spectroscopy. The CD data indicate conversion of random coil structure to highly ordered β-sheet structure in presence of nanomolar and picomolar oligomeric seed at the end of aggregation study. This data suggests that α-Syn oligomer seed induces the aggregation of E46P oligomeric seeds in PD and other Parkinsonian patients.

Figures 12A, 12B:
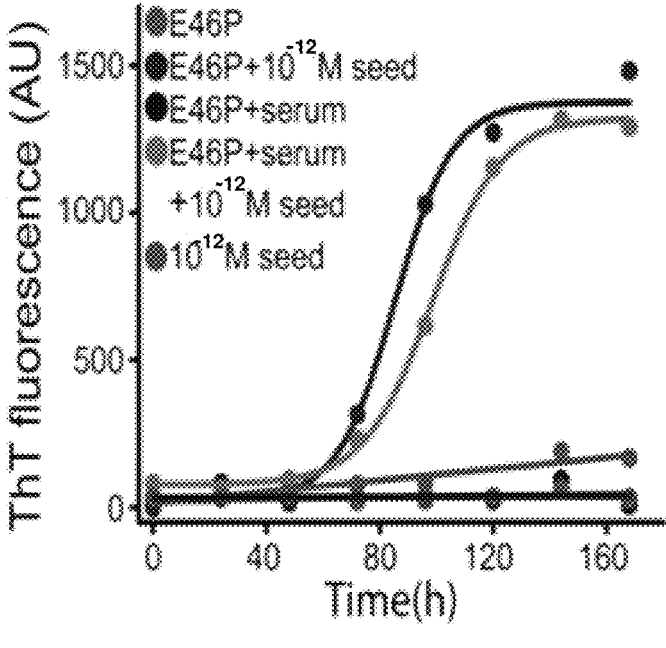
FIGS. 12(*a*) and 12(*b*) are graphs showing ThT fluorescence of simulated serum studies using E46P protein as a substrate in the presence of picomolar WT seed spiked in human blood serum; wherein 12(*a*) shows E46P protein, and 12(*b*) show WT protein, in seed spiked serum, respectively.
Figure 13A:
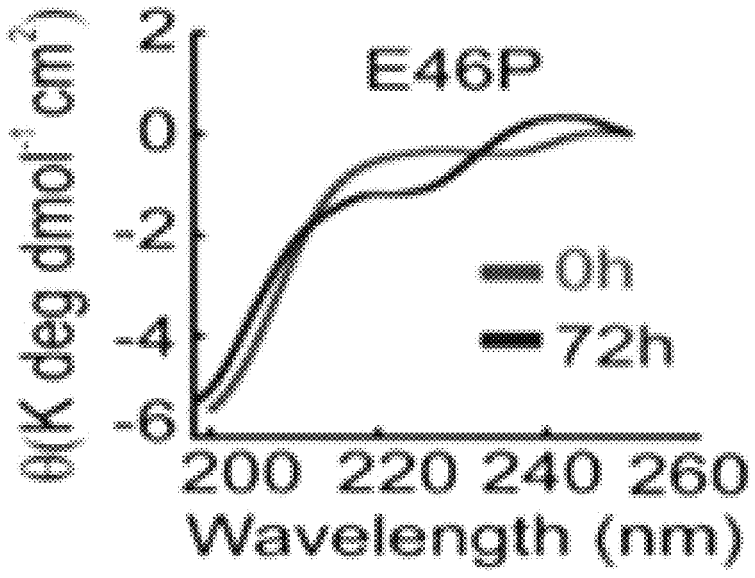
FIGS. 13(*a*) to 13(*d*) are CD spectra showing the structural transition of E46P protein after incubating with WT seed spiked serum and in absence of seed spiked serum; wherein 13(*a*) depicts E46P alone; 13(*b*) depicts E46P with serum; 13(*c*) depicts E46P with $10^{-12}$M WT; 13(*d*) depicts E46P with serum and $10^{-12}$M WT, respectively.
Figure 13B:
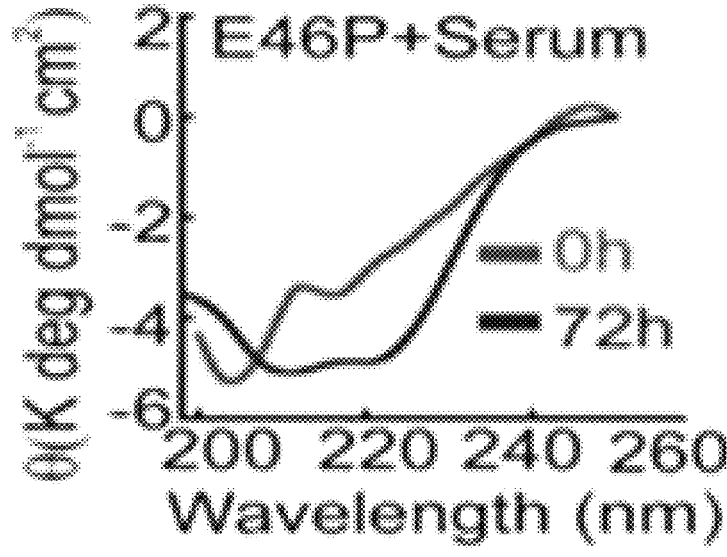
Figure 13C:
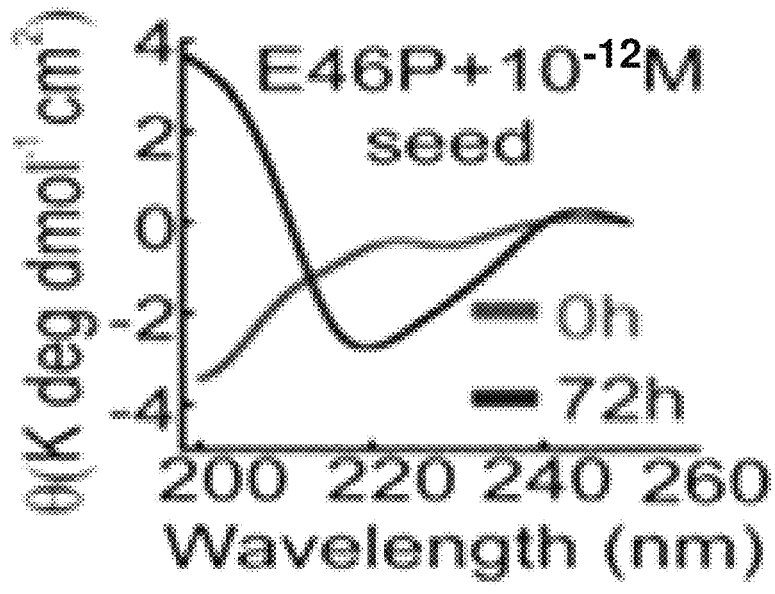
Figure 13D:
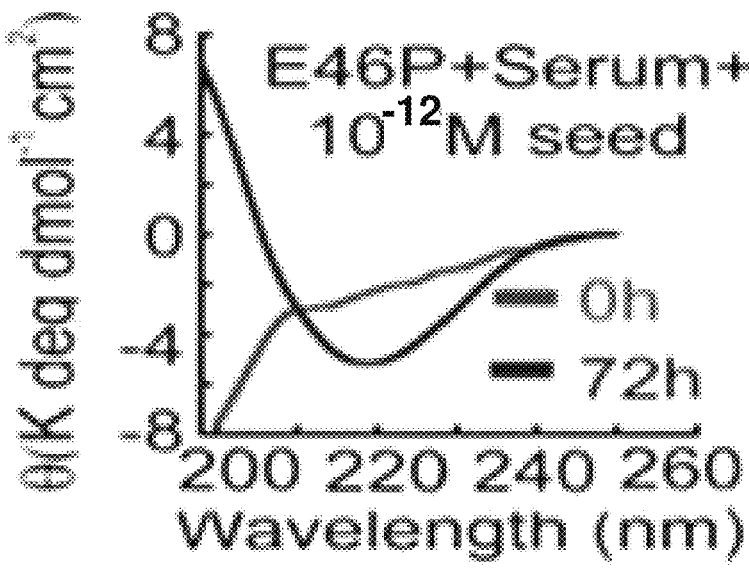
Figure 13E:
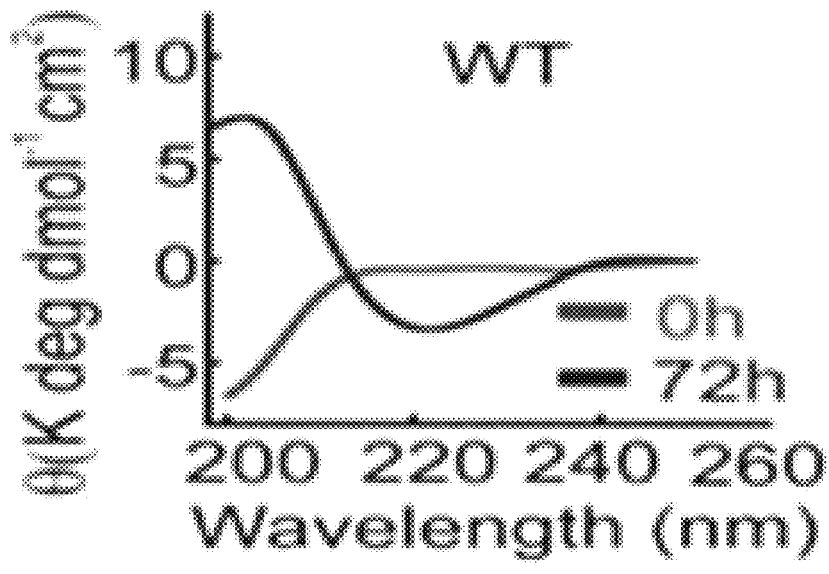
Figure 13F:
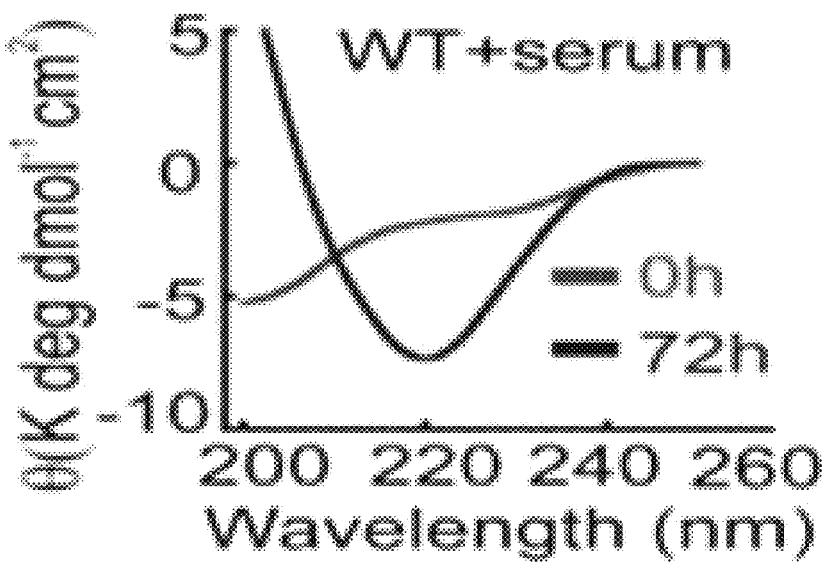
Figure 13G:
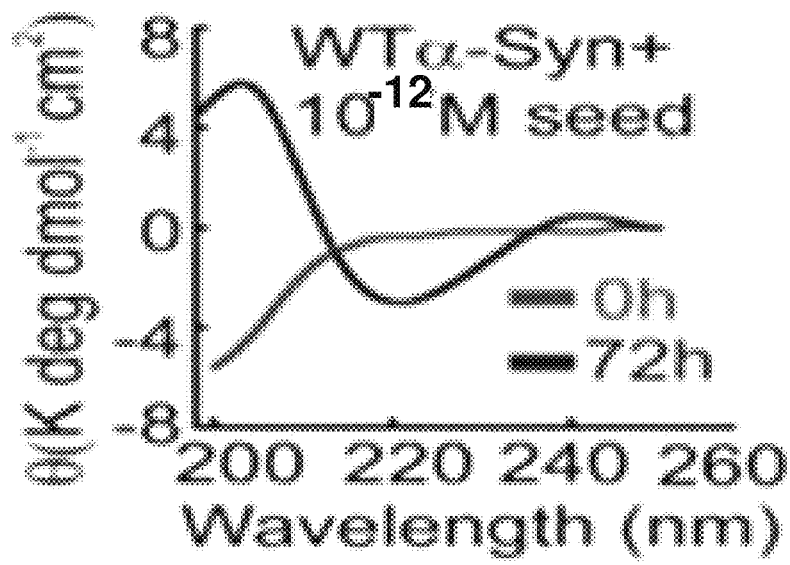
Figure 13H:
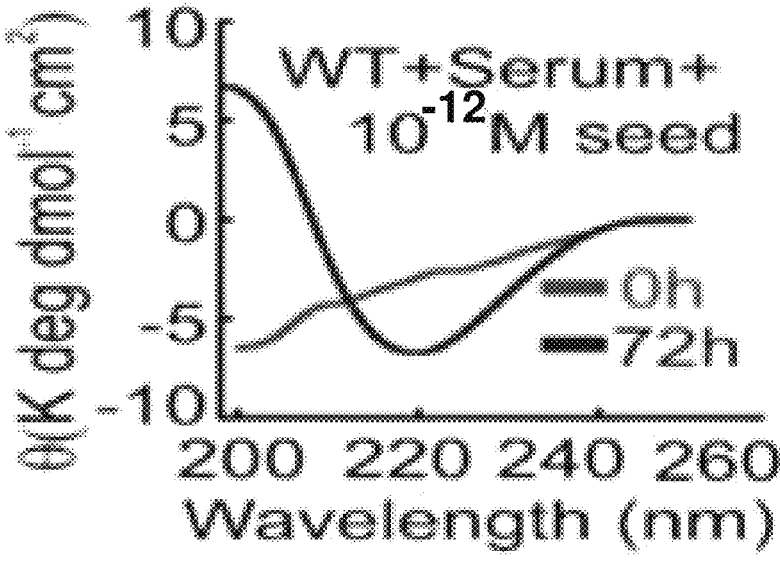

E46P as a Substrate for Simulated Serum Studies for Parkinson's Disease and Other Synucleinopathies To test whether seeding activity of healthy human blood serum spiked with α-Syn seeds is dependent on the presence of α-Syn seed and to mimic the PD and synucleinopathies patient's sample condition, a simulated serum study using healthy human blood was performed. To implement the experimental condition for the simulated serum study, synthetic seeds prepared invitro from WT α-Syn were used to induce the aggregation of E46P. The method is explained in Example 13. The seed-free WT α-Syn and E46P protein of 200 μM concentration was incubated in presence of picomolar seed with continuous rotation at 50 r.p.m in 37 degree C. as a control sample. The test samples were prepared in the presence of blood serum with or without (picomolar) synthetic seed. Amplification of misfolded protein was observed by measuring ThT fluorescence and structural transition of protein monitored using circular dichroism spectroscopy. Under this condition, it was observed that there was a spontaneous aggregation of WT α-Syn but not for E46P mutant alone as it has the property to aggregate only in the presence of seed. Under these conditions, no spontaneous aggregation was observed for E46P along with the serum. To check the effect of the serum spiked with seed, the WT and E46P mutant protein was incubated with serum simulated for PD and other synucleinopathies. Surprisingly, it was observed that there was an increase in ThT fluorescence in presence of serum spiked with WT α-Syn seeds for WT α-Syn, as well as E46P protein. It suggests that the mutant protein substrate was able to amplify the misfolded synthetic seeds present in the blood serum sample. FIGS. 12(*a*) and 12(*b*) are graphs showing ThT fluorescence of simulated serum studies using E46P protein as a substrate in the presence of picomolar WT seed spiked in human blood serum; wherein 12(*a*) shows E46P protein, and 12(*b*) show WT protein, in seed spiked serum, respectively. Further, the structural transition and formation of β-sheet were monitored using Circular dichroism spectroscopy. The CD spectroscopy of E46P alone and E46P in presence of human blood serum did not show any structural transition and remained in a random coil state. Interestingly, data revealed the secondary structure transition of the E46P protein (with or without serum) from random coil to (3-sheet conformation only in presence of seed. While all the mixture of WT α-Syn showed β-sheet conformation at the end of the aggregation reaction because of the spontaneous aggregation property of WT α-Syn. FIGS. 13(*a*) to 13(*d*) are CD spectra showing the structural transition of E46P protein after incubating with WT seed spiked serum and in absence of seed spiked serum; wherein 13(*a*) depicts E46P alone; 13(*b*) depicts E46P with serum; 13(*c*) depicts E46P with $10^{-12}$M WT; and 13(*d*) depicts E46P with serum and $10^{-12}$M WT. FIGS. 13(*e*) to 13(*h*) are CD spectra showing the structural transition of WT after incubating with WT seed spiked serum and in absence of seed spiked serum; wherein 13(*e*) depicts WT alone; 13(*f*) depicts WT with serum; 13(*g*) depicts WT incubated with $10^{-12}$ M WT; and 13(*h*) depicts WT incubated with serum and $10^{-12}$M WT.

Figure 14A:
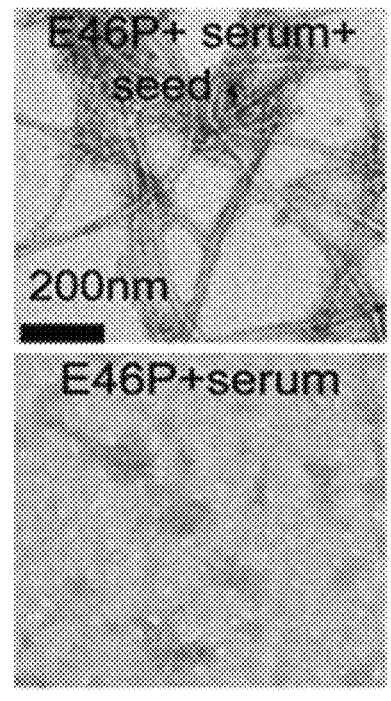
FIGS. 14(*a*) to 14(*d*) are TEM images; wherein 14(*a*) depicts E46P with and without WT seed in serum; 14(*b*) depicts E46P with and without WT seed; 14(*c*) depicts WT incubated with and without WT seed in serum and 14(*d*) depicts WT incubated with and without WT seed, respectively.
Figure 14A:
Figure 14B:
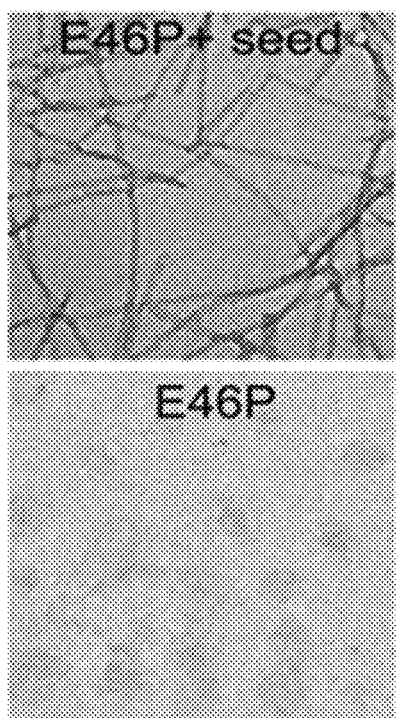

The morphology of the samples was studied by using TEM. FIGS. 14(*a*) to 14(*d*) are TEM images; wherein 14(*a*) depicts E46P with and without WT seed in serum; 14(*b*) depicts E46P with and without WT seed; 14(*c*) depicts WT incubated with and without WT seed in serum and 14(*d*) depicts WT incubated with and without WT seed, respectively. The data suggest that the E46P alone did not show any amyloid fibril structure in absence of seed. The amorphous aggregates were observed in the E46P that incubated along with the serum sample, however, lacked the typical amyloid morphology. The E46P in presence of seeds showed amyloid fibrils as mentioned earlier, also E46P protein along with serum in presence of seed showed typical amyloid fibrillar morphology. WT α-Syn samples showed amyloid fibrillar morphology in all the conditions as expected.

PMCA with Healthy Serum Sample Spiked with Different Concentrations of Seed.

Figure 15:
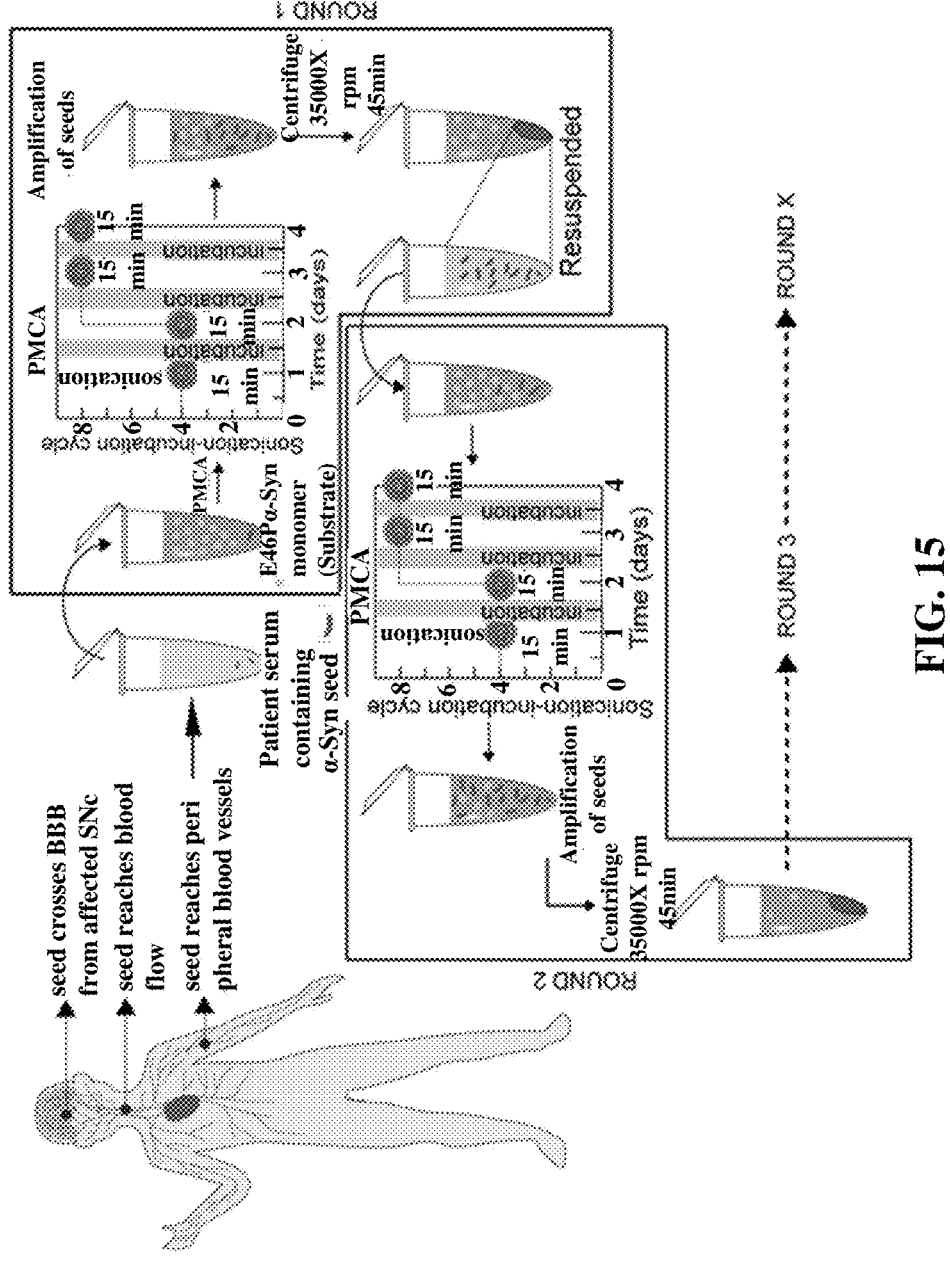
FIG. 15 is a schematic representation depicting the PMCA assay for the detection of misfolded α-Syn in simulated and patient blood samples.
Figure 16:
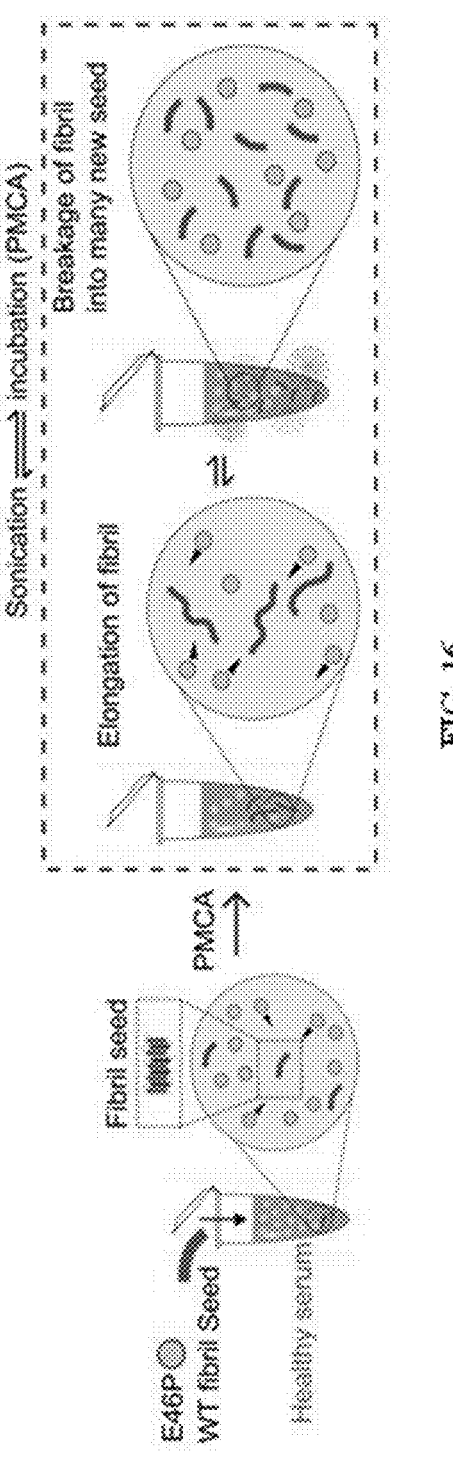
FIG. 16 is a schematic representation illustrating PMCA assay with simulated PD blood, wherein healthy serum samples were spiked with different concentrations of WT seed and E46P monomer was added to the solutions.
Figure 17:
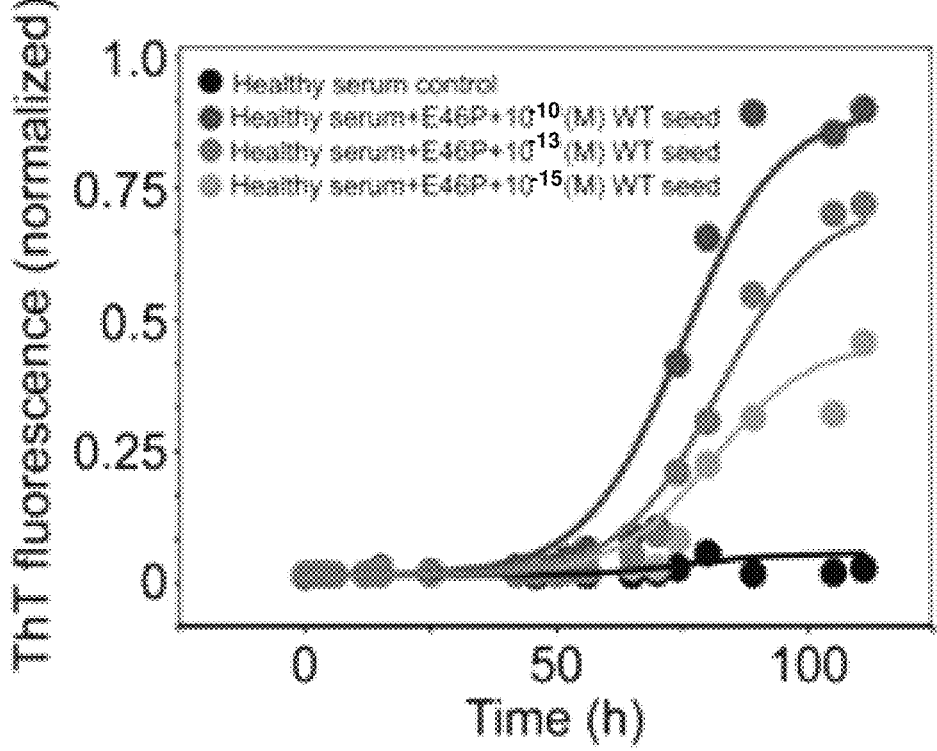
FIG. 17 is a graph depicting ThT fluorescence of simulated PMCA at different concentrations of seed.
Figures 18A, 18B, 18C:
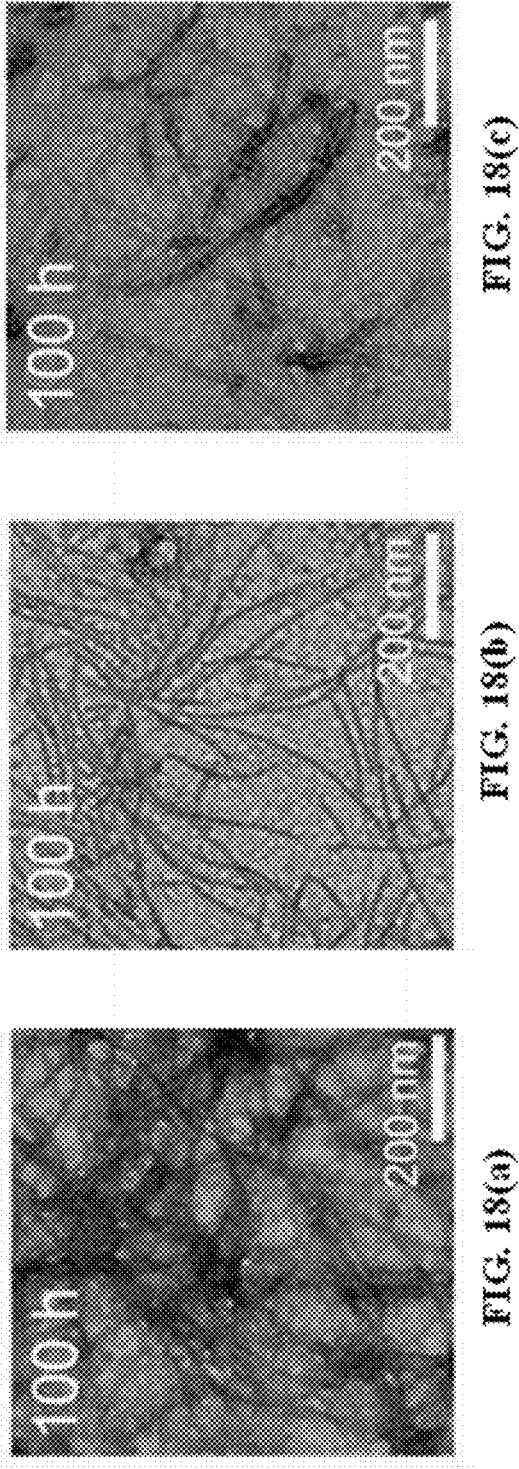
FIGS. 18(*a*) to 18(*c*) are TEM images of simulated PMCA at different concentrations of seed; wherein 18(*a*) depicts E46P incubated with $10^{-10}$M WT seed and healthy serum; 18(*b*) depicts E46P incubated with $10^{-13}$M WT seed and healthy serum, and 18(*c*) depicts E46P incubated with $10^{-15}$M WT seed and healthy serum, respectively.
Figure 19B:
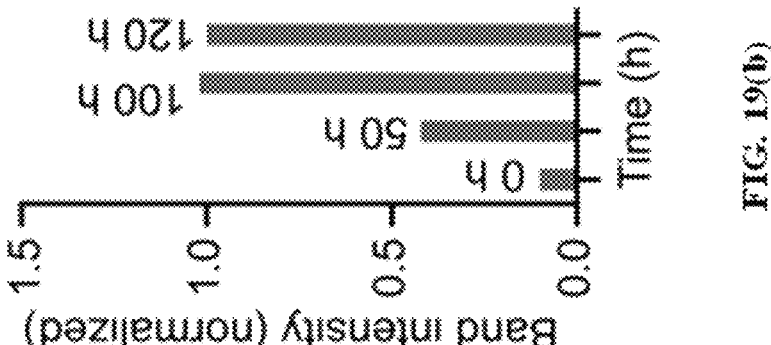
FIGS. 19(*a*) and 19(*b*) are western blot analysis results of amplified E46P α-Syn protein with $10^{-10}$ seed concentration; wherein 19(*a*) depicts western blot image showing band intensity of E46P α-Syn protein at different time-points; and 19(*b*) is a graph depicting increase in band intensity of E46P α-Syn protein with time, respectively.
Figure 19A:
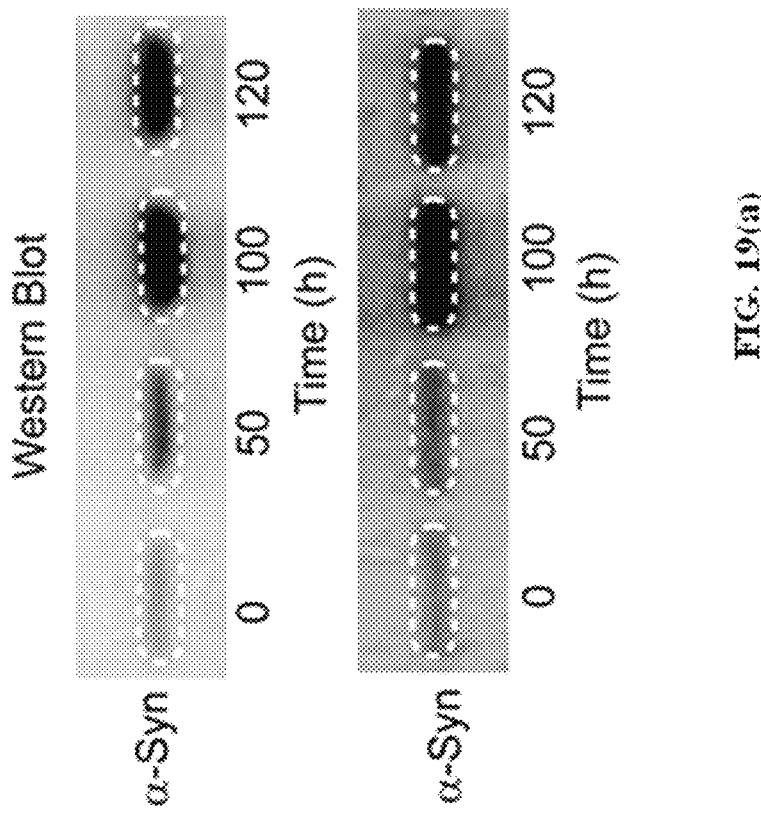

FIG. 15 is a schematic representation depicting the PMCA assay for the detection of misfolded α-Syn in simulated and patient blood samples. Wherein the aliquots of the substrate were prepared in 20 mM glycine NaOH buffer, pH 7.4, 0.01% sodium azide and mixed with serum sample in a final volume of 100 μl and loaded into a 0.5 ml Eppendorf tube. The reaction mixture was then subjected to PMCA assay. Manually it was programmed for 6 hr incubation at 37 degree C., followed by bath sonication for 15 min for initial 8 cycles and another 16 cycles 3 hr incubation, followed by 15 min bath sonication at 40 degree C. Multiple rounds of 24-cycles each were performed and the amplification of pathological aggregates after completion of the round was observed. To perform the simulated serum study using PMCA assay the healthy serum samples were spiked with different concentrations of WT seed. E46P monomer was added, as substrate, to the solutions. FIG. 16 is a schematic representation illustrating PMCA assay with simulated PD blood, wherein healthy serum samples were spiked with different concentrations of WT seed and E46P monomer was added to the solutions. The PMCA assay for blood samples results in elongation of the fibrils only if seeds are present in the reaction mixture because of the nature of the E46P protein. The amplification of misfolded protein was observed by measuring ThT fluorescence. The seed ($10^{-10}$, $10^{-13}$ and $10^{-15}$M) spiked serum samples showed increased ThT binding as the number of PMCA cycles increases. There was no ThT binding observed for the healthy serum control sample. FIG. 17 is a graph depicting ThT fluorescence of simulated PMCA at different concentrations of seed. To observe the morphology of amplified product transmission electron microscopy was performed. The samples were negatively stained with uranyl formate and subsequently imaged at magnifications ranging from 24000 to 60000× with the help of TEM (CM200). FIGS. 18(*a*) to 18(*c*) are TEM images of simulated PMCA at different concentrations of seed; wherein 18(*a*) depicts E46P incubated with $10^{-10}$M WT seed and healthy serum; 18(*b*) depicts E46P incubated with $10^{-13}$M WT seed and healthy serum, and 18(*c*) depicts E46P incubated with $10^{-15}$M WT seed and healthy serum, respectively. From the images it can be seen that PMCA results in amyloid formation even in presence of very low seed concentration ($10^{-10}$, $10^{-13}$ and $10^{-15}$M) in the simulated serum sample. Further at different time-points, the solutions were ultracentrifuged to pellet down the amplified misfolded product and used for Western blot assay to confirm the presence of amplified misfolded α-Syn. FIGS. 19(*a*) and 19(*b*) are western blot analysis results of amplified E46P α-Syn protein with $10^{-10}$ seed concentration; wherein 19(*a*) depicts western blot image showing band intensity of E46P α-Syn protein at different time-points; and 19(*b*) is a graph depicting increase in band intensity of E46P α-Syn protein with time, respectively. Results show that in the pellet fraction, more and more α-Syn is getting accumulated. It proves that E46P α-Syn indeed aggregates to form amyloid during PMCA. The western blot is done with $10^{-10}$ (M) seeds only at different time-points.

Figure 20A:
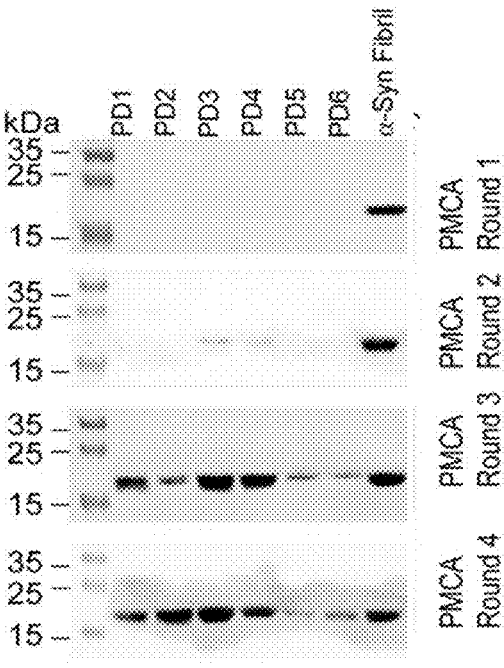
FIGS. 20(*a*) to 20(*c*) are western blot images for PD and HC samples (PD1-PD12; HC1-HC7) after the completion of each round of PMCA assay; wherein 20(*a*)depicts samples PD1 to PD6; 20(*b*) depicts samples PD7 to PD12, and 20(*c*) depicts samples HC1 to HC7, band intensity respectively (numbers on the left side indicate the position of the molecular weight marker)
Figure 20B:
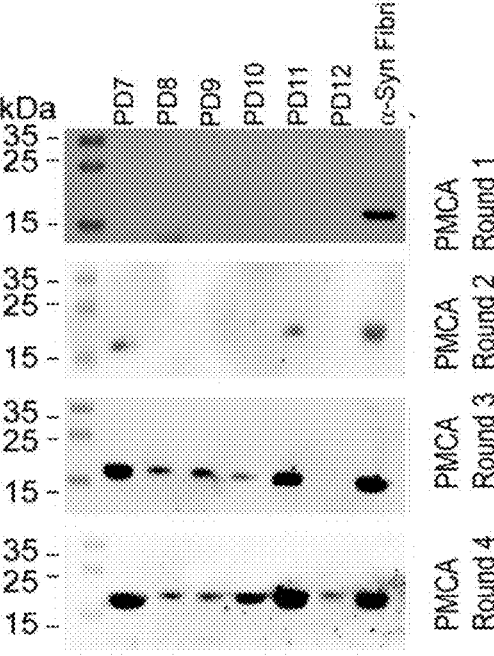
Figure 20C:
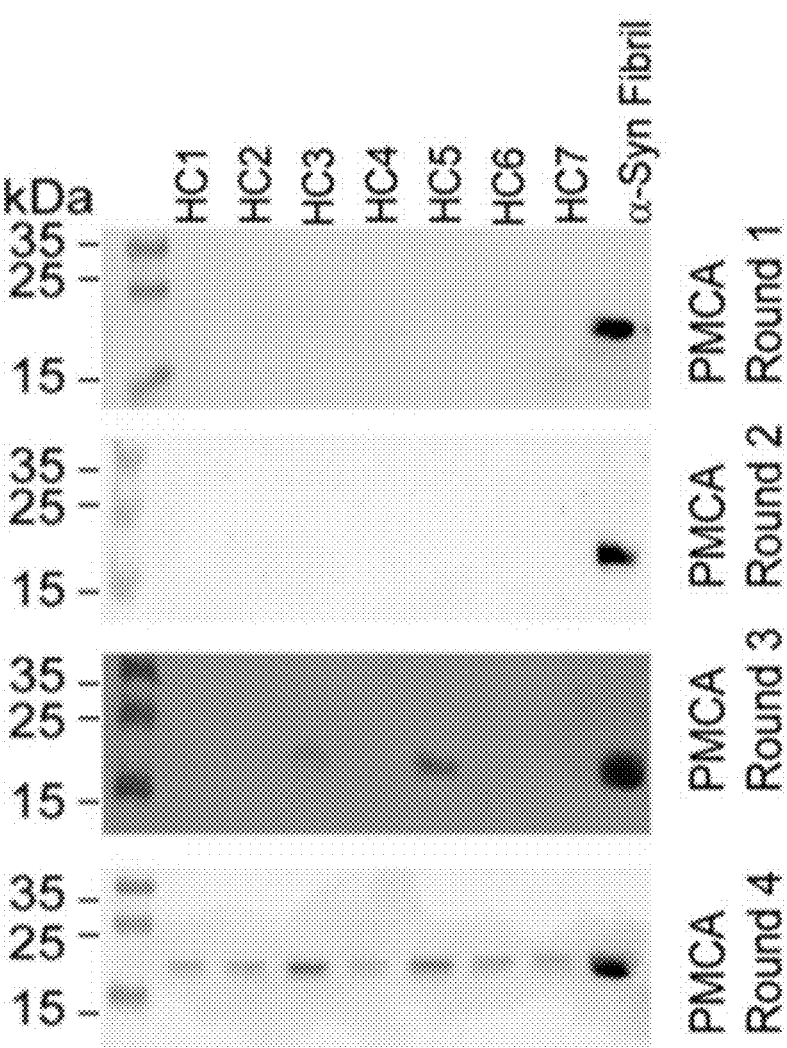
Figures 21A, 21B, 21C:
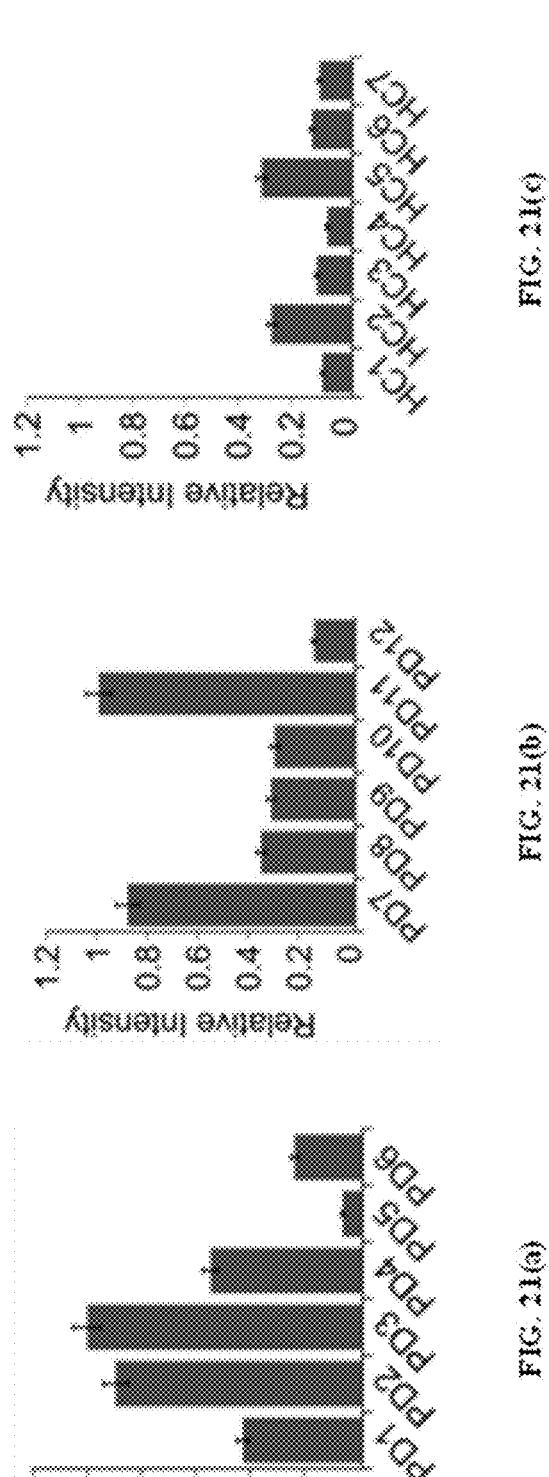
FIGS. 21(*a*) to 21(*c*) are graphs depicting the densitometric data generated from western blot of samples obtained at the end of $4^{th}$ round of PMCA reaction; wherein 21(*a*) depicts samples PD1 to PD6; 21(*b*) depicts samples PD7 to PD12, and 21(*c*) depicts samples HC1 to HC7, relative intensity respectively.
Figure 22A:
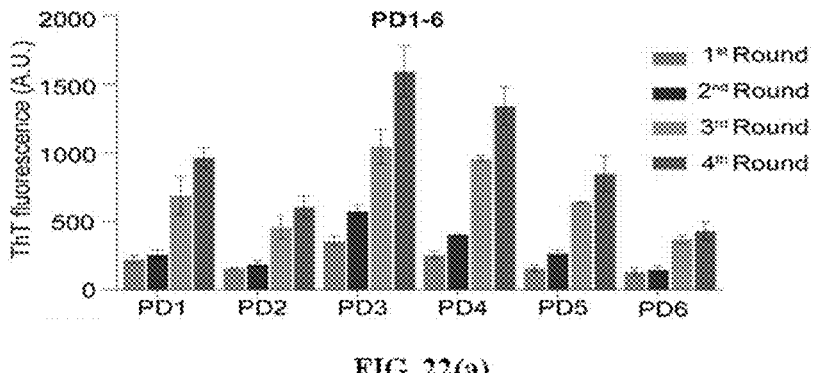
FIGS. 22(*a*) to 22(*c*) are graphs of ThT fluorescence assay for PD and HC samples after completion of each round of PMCA; wherein 22(*a*) depicts samples PD1 to PD6; 22(*b*) depicts samples PD7 to PD12, and 22(*c*) depicts samples HC1 to HC7, ThT fluorescence respectively.
Figure 22B:
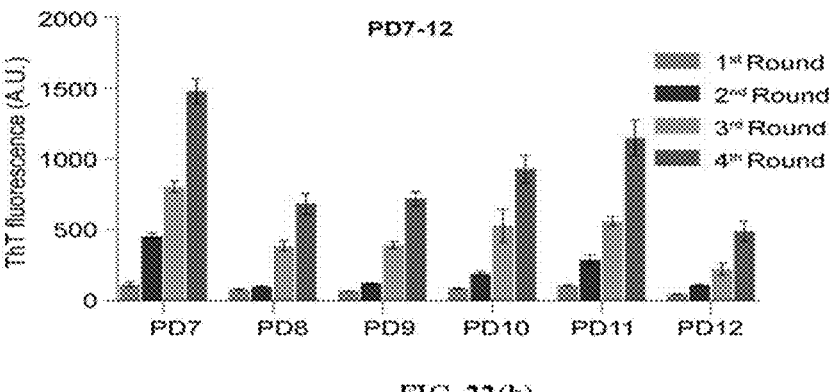
Figure 22C:
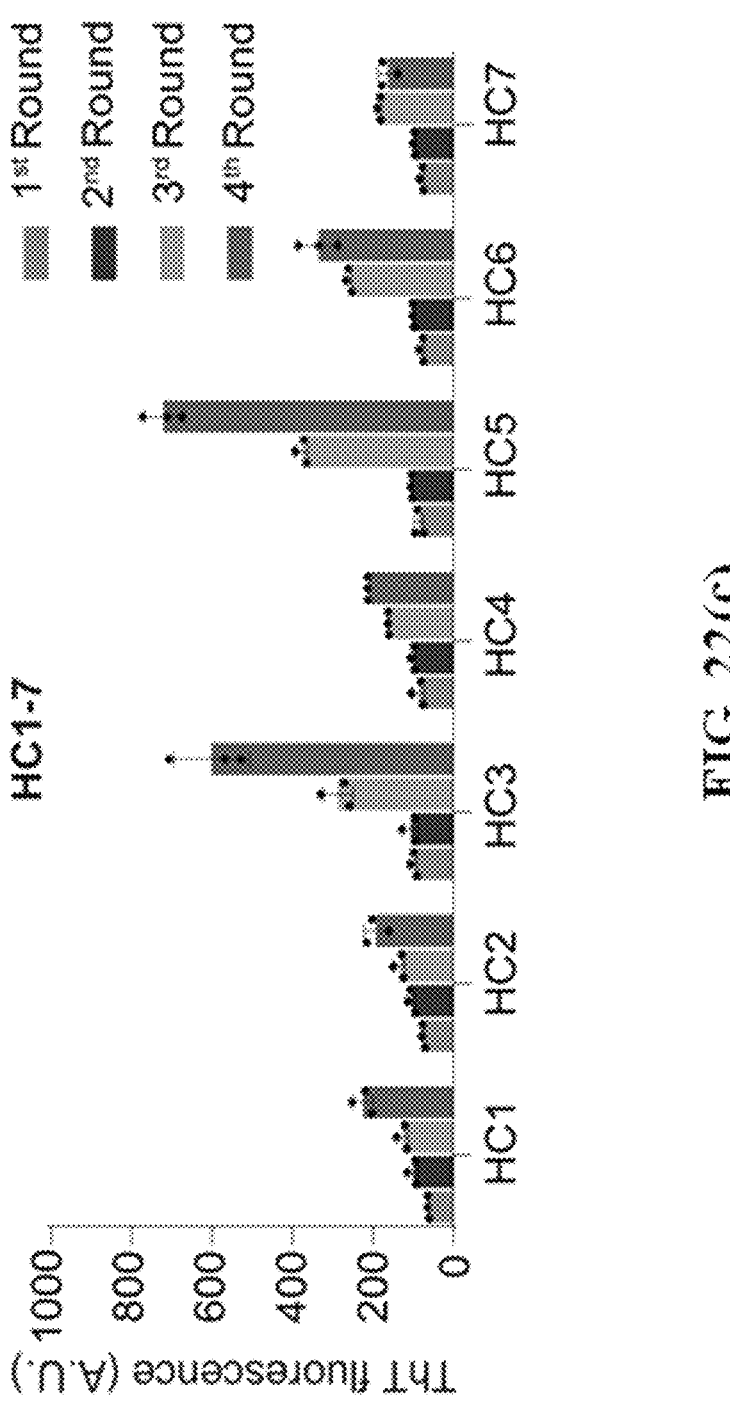
Figure 23A:
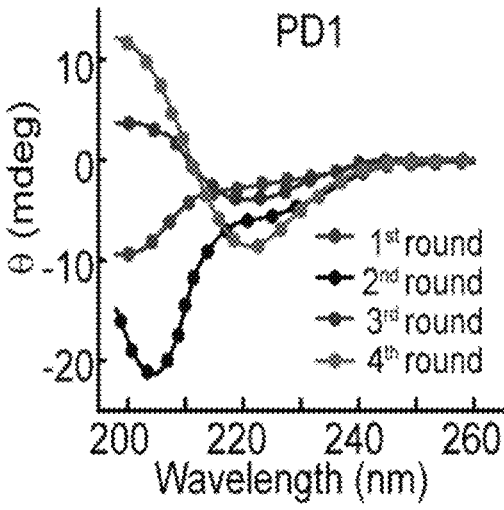
FIGS. 23(*a*) to 23(*l*) are CD spectra for samples PD1 to PD12 respectively, after completion of each round of PMCA.
Figure 23B:
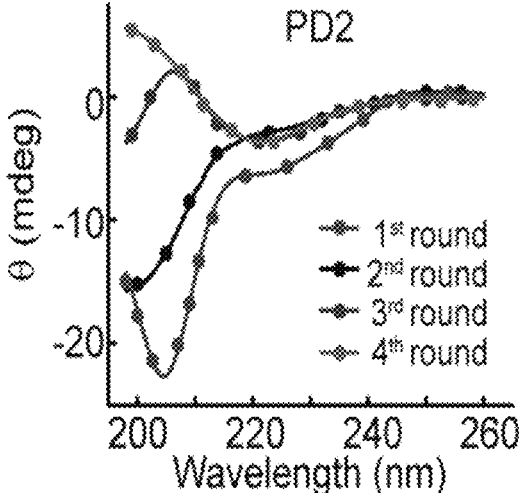
Figure 23C:
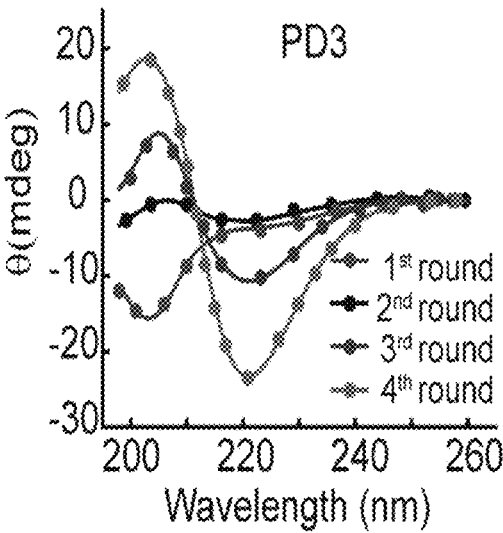
Figure 23D:
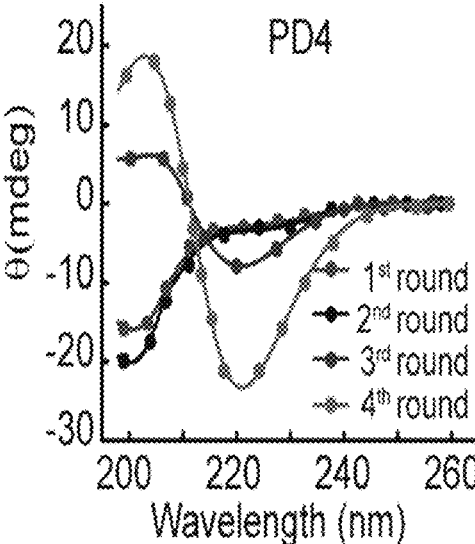
Figure 23E:
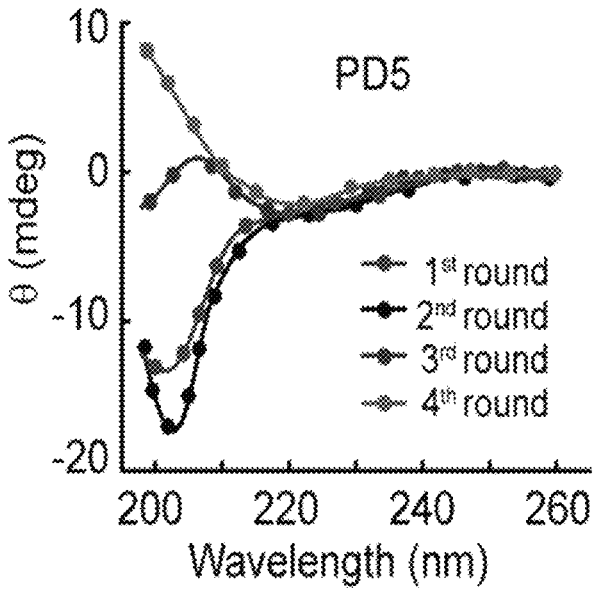
Figure 23F:
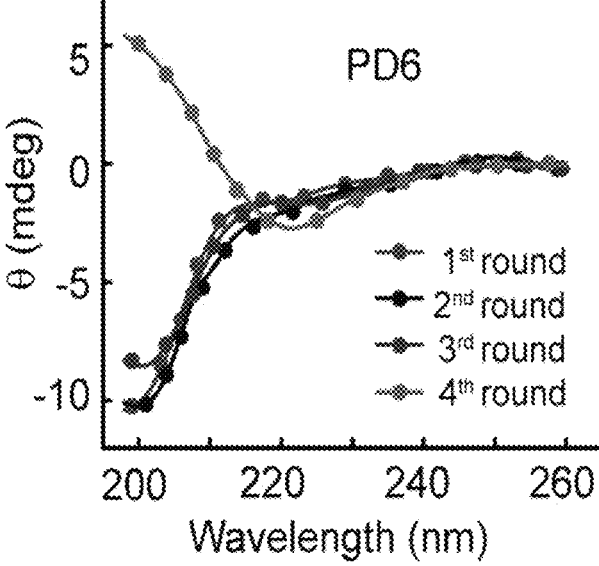
Figure 23G:
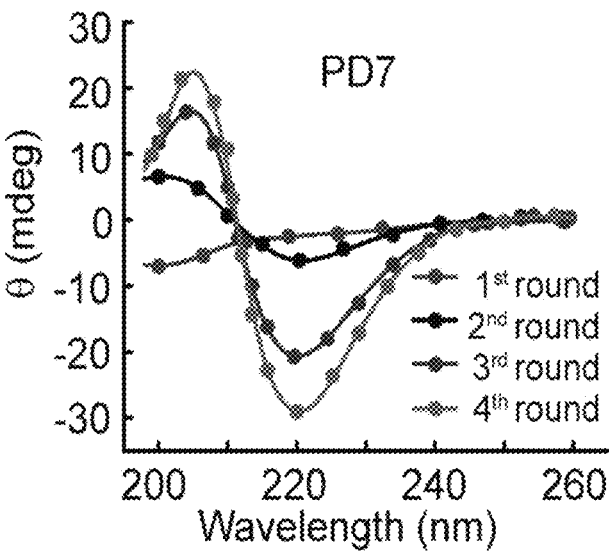
Figure 23H:
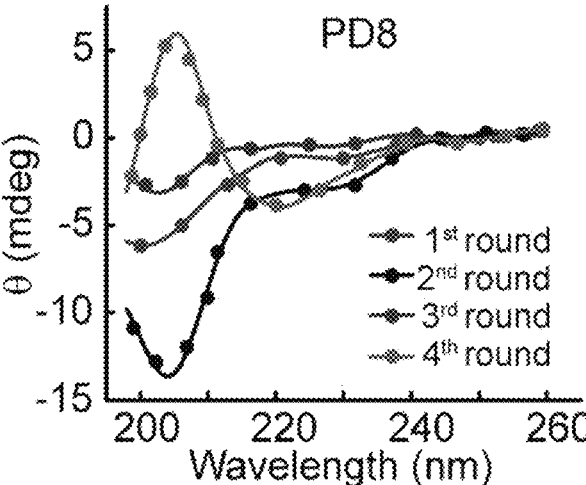
Figure 23I:
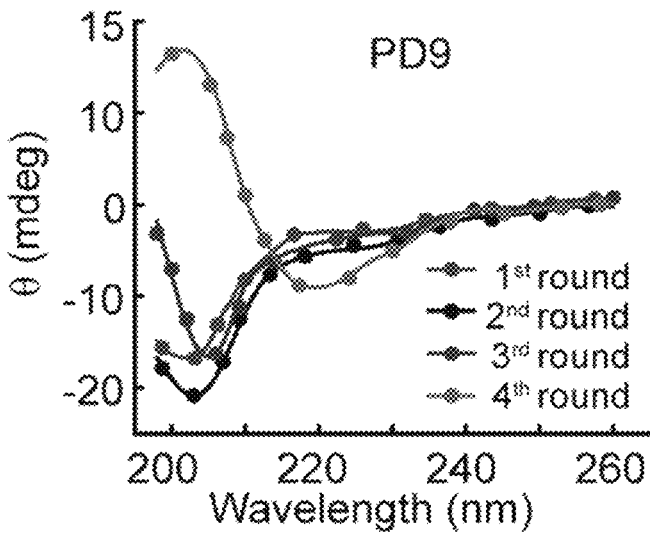
Figure 23J:
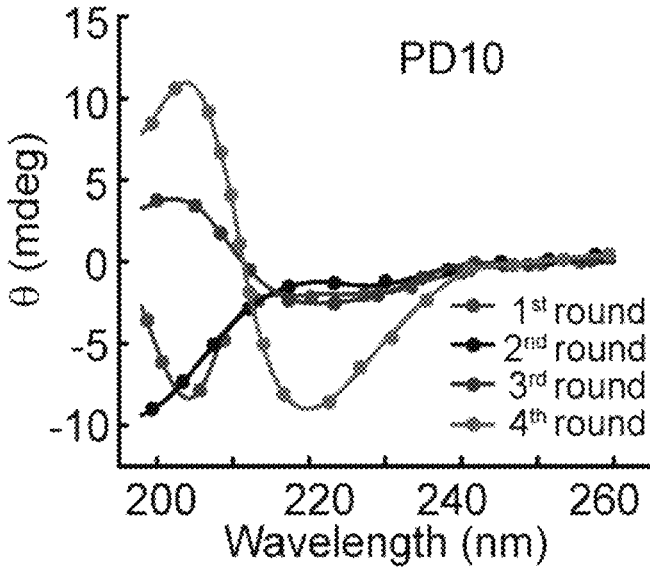
Figure 23K:
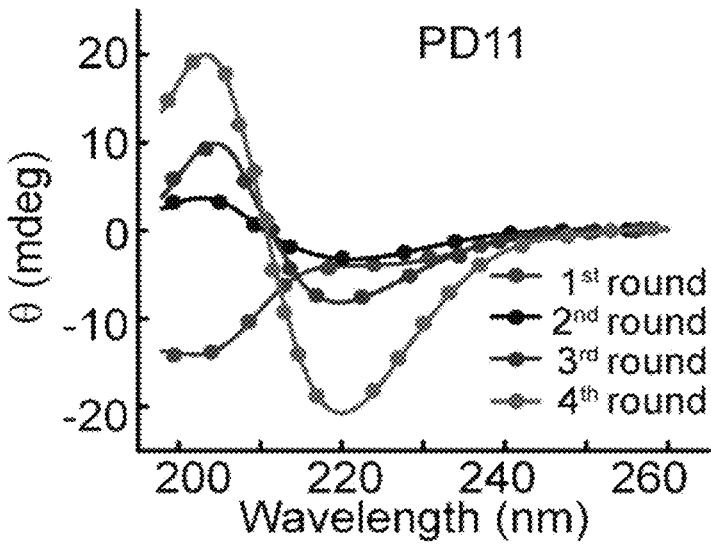
Figure 23L:
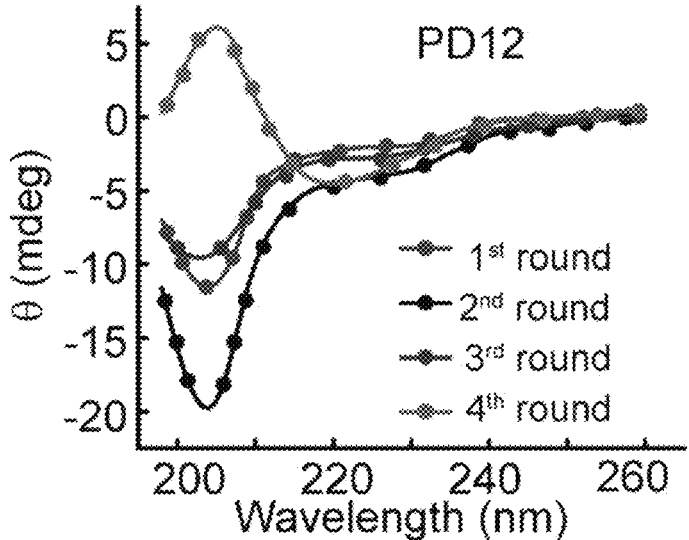
Figure 23M:
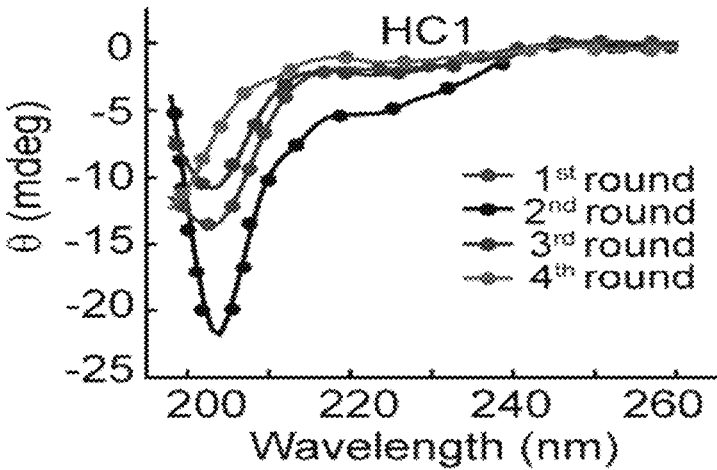
Figure 23N:
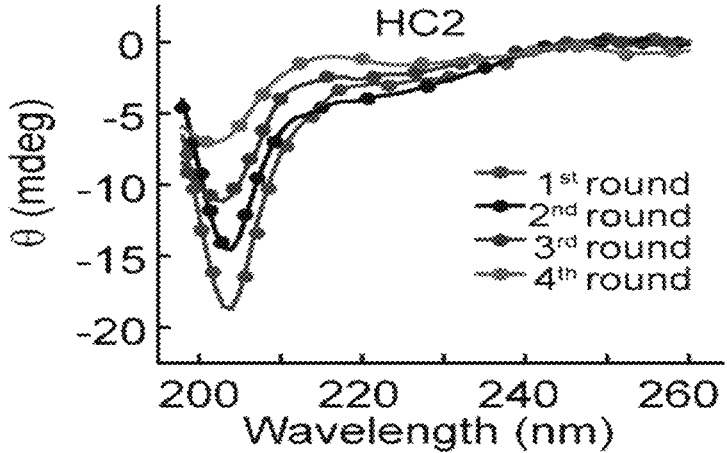
Figure 23O:
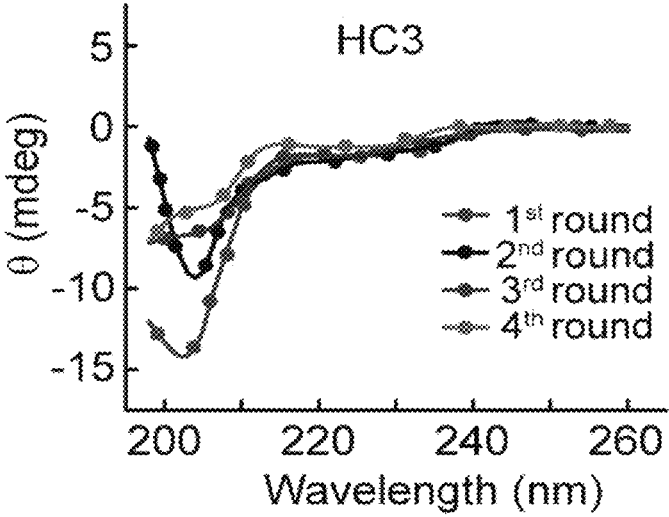
Figure 23P:
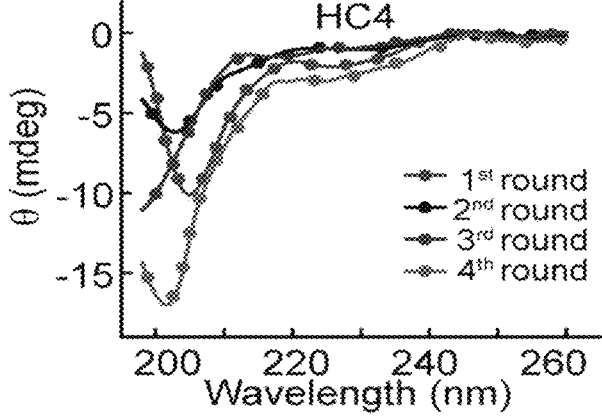
Figure 23Q:
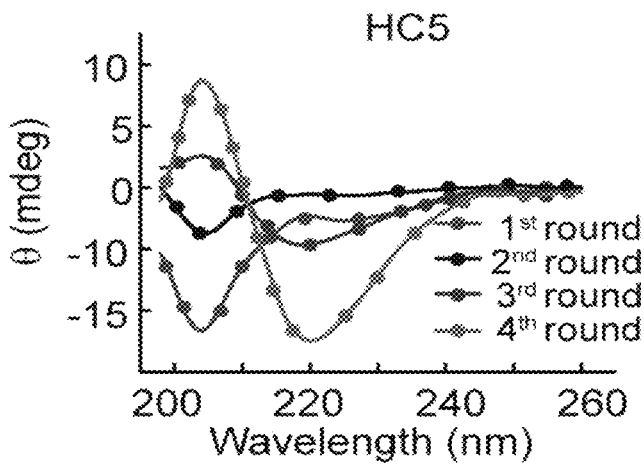
Figure 23R:
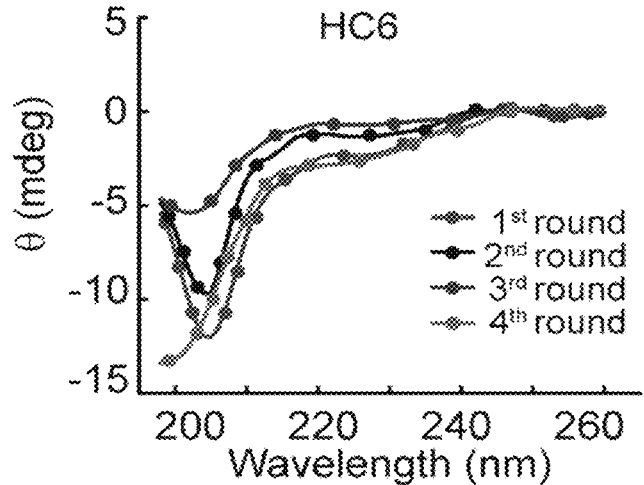
Figure 23S:
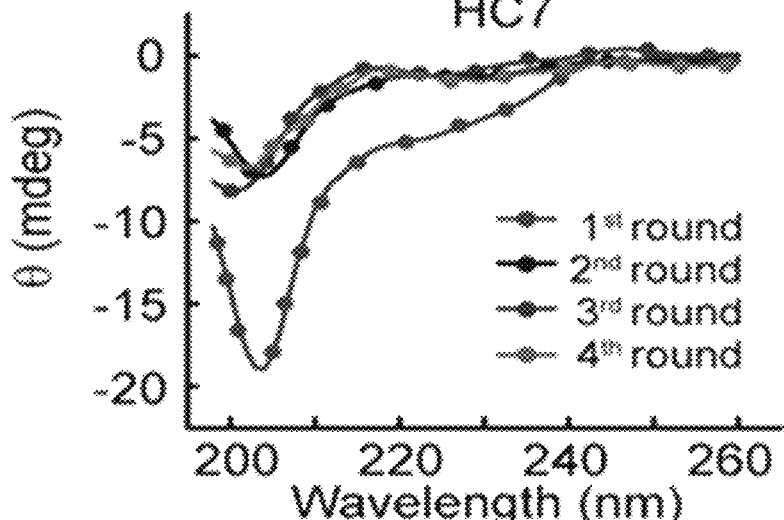

E46P as a Substrate for Diagnosis of Parkinson's Disease by Detection of Misfolded α-Syn Species in the Blood Samples To detect presence of misfolded α-Syn in PD patient's blood samples, serial rounds of the PMCA assay were performed. Blood samples from 12 clinically diagnosed Parkinson's disease (PD) patients and 7 healthy controls (HC) were analyzed. Example 15 and 16 provide the sample preparation and method for the analysis. The serum samples of both PD patients and healthy controls were incubated with an excess amount of monomeric E46P substrate protein. PMCA cycles were carried out for all the samples and pellets were obtained by carrying out ultracentrifugation at high speed (35000 rpm) for 45 min. The pelleted higher-order misfolded samples, after each round of PCMA were further diluted in the same buffer and used for subsequent characterization by SDS-PAGE, western blot assay, ThT fluorescence assay, CD spectroscopy and TEM imaging. FIGS. 20(*a*) to 20(*c*) are western blot images for PD and HC samples (PD1 to PD12; HC1 to HC7) after the completion of each round of PMCA assay; wherein 20(*a*) depicts samples PD1 to PD6; 20(*b*) depicts samples PD7 to PD12, and 20(*c*) depicts samples HC1 to HC7, band intensity respectively (numbers on the left side indicate the position of the molecular weight marker). FIGS. 21(*a*) to 21(*c*) are graphs depicting the densitometric data generated from western blot of samples obtained at the end of $4^{th}$ round of PMCA reaction; wherein 21(*a*) depicts samples PD1 to PD6; 21(*b*) depicts samples PD7 to PD12, and 21(*c*) depicts samples HC1 to HC7, relative intensity respectively. FIGS. 22(*a*) to 22(*c*) are graphs of ThT fluorescence assay for PD and HC samples after completion of each round of PMCA; wherein 22(*a*) depicts samples PD1 to PD6; 22(*b*) depicts samples PD7 to PD12, and 22(*c*) depicts samples HC1 to HC7, ThT fluorescence respectively. FIG. 23(*a*), 23(*b*), 23(*c*), 23(*d*), 23(*e*), 23(*f*), 23(*g*), 23(*h*), 23(*i*), 23(*j*), 23(*k*) and 23(*l*) are CD spectra for samples PD1, PD2, PD3, PD4, PD5, PD6, PD7, PD8, PD9, PD10, PD11 and PD12 respectively, after completion of each round of PMCA. FIGS. 23(*m*), 23(*n*), 23(*o*), 23(*p*), 23(*q*), 23(*r*) and 23(*s*) are CD spectra for samples HC1, HC2, HC3, HC4, HC5, HC6 and HC7 respectively, after completion of each round of PMCA. PD patient samples showed structural transition of E46P protein from random coil to β-sheet structure in presence of seed.

Whereas in absence of seed, E46P remained unstructured (random coil) incase of HC samples (except HC5).

Figures 24A, 24B, 24C, 24D, 24E, 24F:
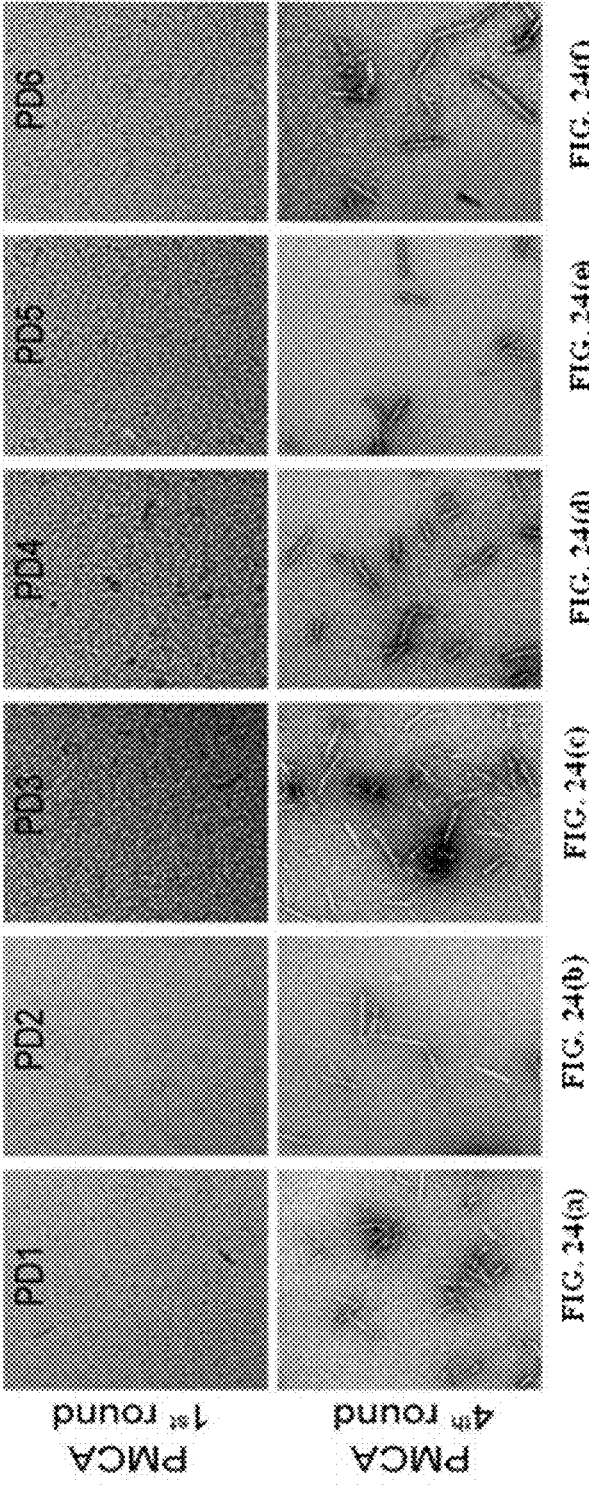
FIGS. 24(*a*) to 24(*l*) are TEM micrographs for samples PD1 to PD12 respectively, after completion of $1^{st}$ and $4^{th}$ round of PMCA.
Figures 24G, 24H, 24I, 24J, 24K, 24L:
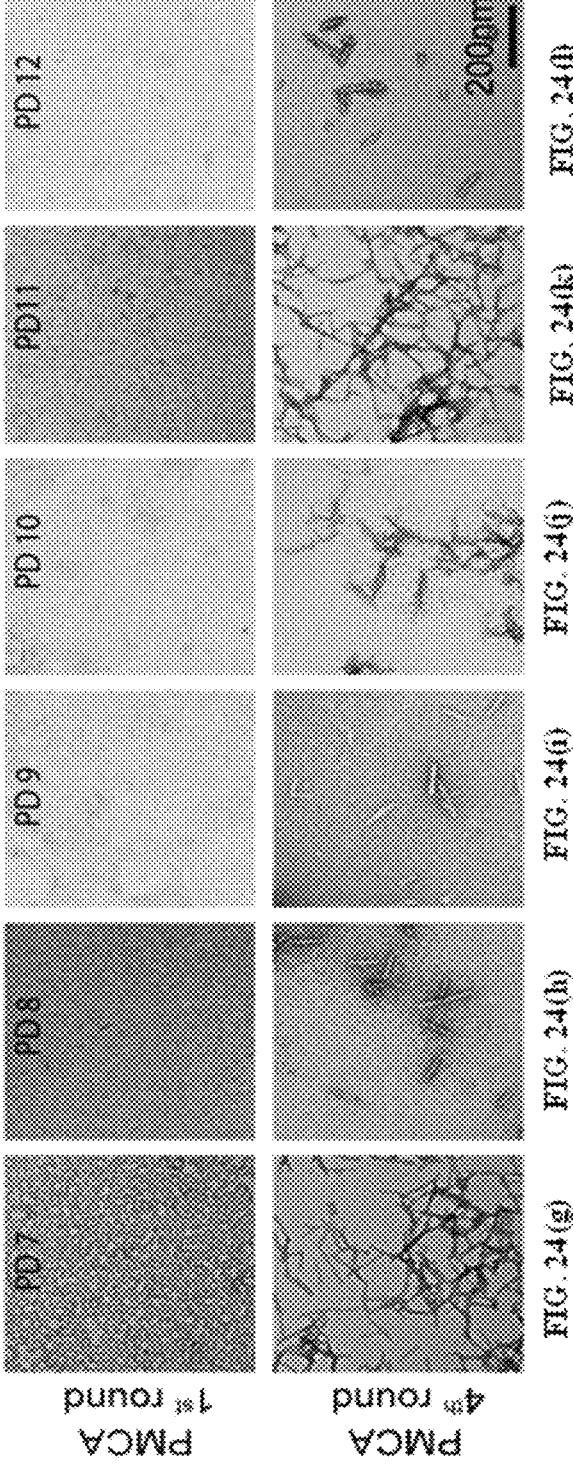
Figures 24M, 24N, 24O, 24P, 24Q, 24R, 24S:
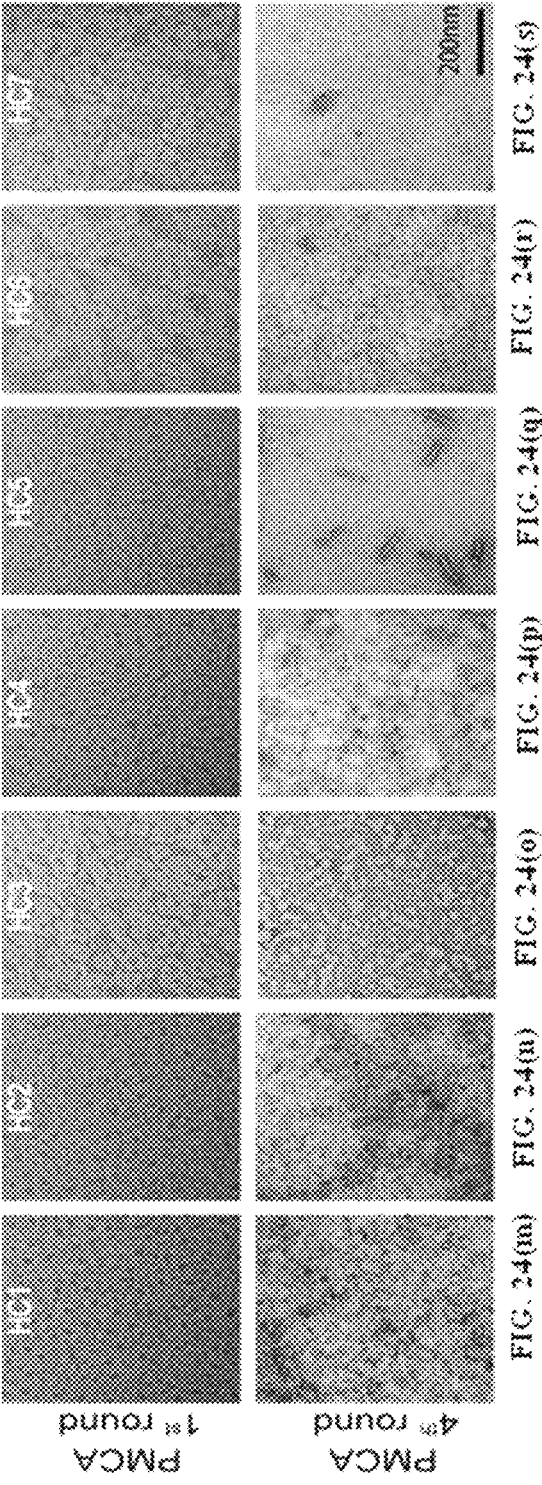

FIG. 24(*a*), 24(*b*), 24(*c*), 24(*d*), 24(*e*), 24(*f*), 24(*g*), 24(*h*), 24(*i*), 24(*j*), 24(*k*) and 24(*l*) are TEM micrographs for samples PD1, PD2, PD3, PD4, PD5, PD6, PD7, PD8, PD9, PD10, PD11 and PD12 respectively, after completion of $1^{st}$ and $4^{th}$ round of PMCA. FIGS. 24(*m*), 24(*n*), 24(*o*), 24(*p*), 24(*q*), 24(*r*) and 24(*s*) are TEM micrographs for samples HC1, HC2, HC3, HC4, HC5, HC6 and HC7 respectively, after completion of $1^{st}$ and $4^{th}$ round of PMCA. From the western blot and ThT fluorescence assay results, no significant difference was seen between HC and PD samples after the first round of PMCA. Also, amyloid morphology was not observed in TEM imaging after the first round of PMCA. A similar trend was observed after the second round with the exception of a few subjects which showed higher amplification signals. A significant difference between the HC and PD samples was observed after completion of the third round of PMCA assay (FIG. 20), which was supported by the ThT fluorescence data (FIG. 22), Circular dichroism spectroscopy (FIG. 23), and TEM imaging (FIG. 24). All the twelve PD blood samples were observed to show positive amplified signals at the end of the fourth round of PMCA whereas one of the controls (HC5) also gave positive amplified signal. The densitometry analysis of the western blot assay was performed after the fourth round of PMCA (FIG. 21). From the data it can be seen that all the PD samples showed higher amplified signals compared to healthy controls (except HC5).

To validate the nature of amplified misfolded samples and for high throughput screening, Congo Red Dot (CRD) test was performed. Example 16 describes the method carried out to perform the Congo red dot test. The assay was optimized for high throughput screening of amplified amyloid products.

Figure 25A:
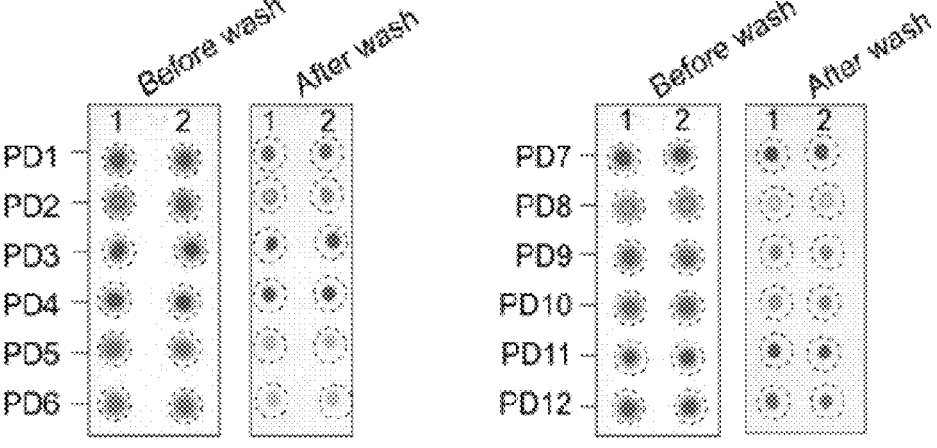
FIGS. 25(*a*) and 25(*b*) depicts representative images of congo red dot (CRD) test of PD and HC blood samples and controls, after completion of PMCA assay; wherein 25(*a*) depicts samples PD1 to PD12, and 25(*b*) depicts samples HC1 to HC7 and controls, respectively.
Figure 25B:
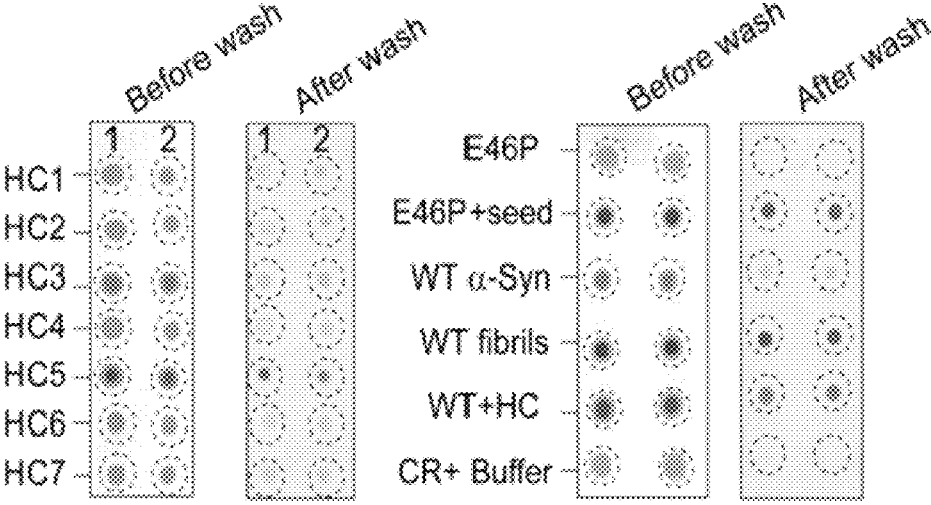
Figure 25C:
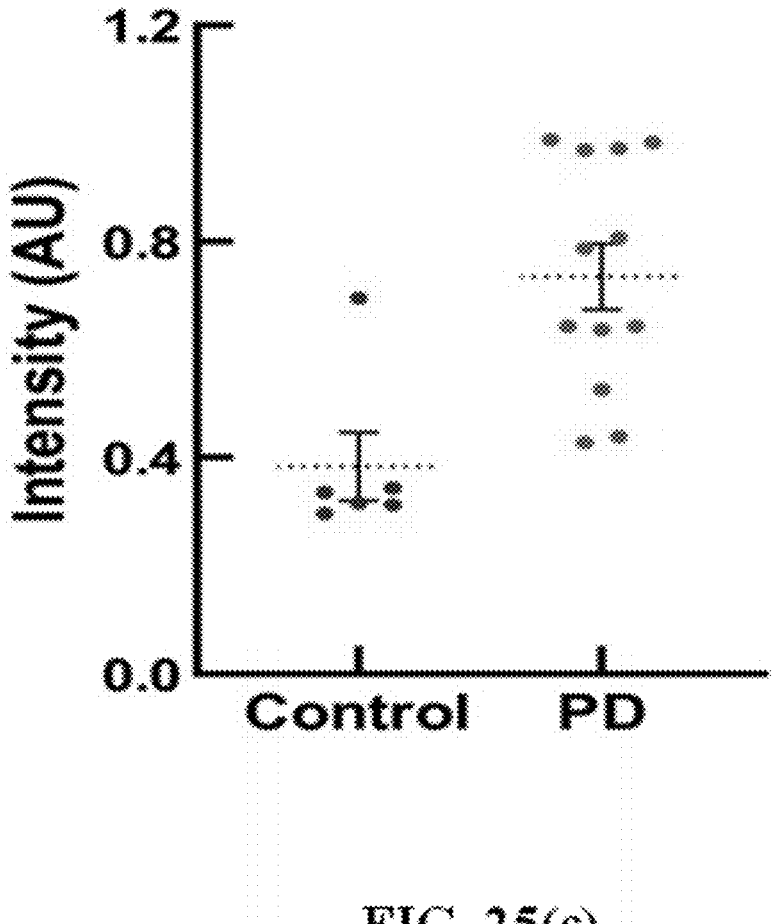

All the 12 PD and 7 HC samples were screened at the end of the PMCA reaction for Congo red dye retention assay. E46P +WT seed, WT α-Syn fibrils, WT α-Syn+healthy control serum sample were kept as positive controls for the assay; whereas E46P monomer alone, WT α-Syn monomer alone, and glycine NaOH buffer were kept as negative control. FIGS. 25(*a*) and 25(*b*) depicts representative images of congo red dot (CRD) test of PD and HC blood samples and controls, after completion of PMCA assay; wherein 25(*a*) depicts samples PD1 to PD12; 25(*b*) depicts samples HC1 to HC7 and controls, respectively. FIG. 25(*c*) is a graph depicting quantification of congo red blot assay illustrating the intensity of congo red dye retention among patient samples and corresponding controls after completion of PMCA assay. The amplified PMCA samples were mixed with congo red dye and spotted in duplicate on nitrocellulose membrane. The membrane was photographed before and after washing with ethanol. The congo red dye retention spots as can be seen in the FIG. 25, corresponds to presence of amyloid protein. All PD samples showed higher intensity of Congo red dye, even after washing with increasing concentrations of ethanol (50%, 70%, and 90%); while none of the control showed Congo red binding (except HC5 even after four rounds of PMCA assay). The increased intensity observed for patient samples indicates higher congo red retention compared to controls due to the presence of amplified amyloid fibrils. Overall, a sensitivity of 100% and specificity of 87.5% was achieved in identifying patients affected by PD using the aforementioned test. Based on the overall findings, it may be suggested that, detection of misfolded α-Syn by α-Syn PMCA in the blood of PD affected patients may offer a good, less-invasive and sensitive biochemical assay for the diagnosis of the disease.

The invention is further described by reference to the following examples by way of illustration only and should not be construed to limit the scope of the embodiments disclosed herein. It will be apparent to those skilled in the art that many modifications, both to materials and methods, may be practiced without departing from the scope of the claimed embodiments.

Example 2

Preparation of Low Molecular Weight (LMW) Protein for Protein Aggregation Assay Lyophilized protein was dissolved in 20 mM Glycine-NaOH buffer (pH 7.4, 0.01% sodium azide). Protein was dissolved by adding few drops of 2M NaOH and pH was adjusted to 7.4 using 2N HCl using micro pH meter (Mettler-Toledo, Switzerland, Model S20, Seven easy). The solution was then dialyzed overnight through 10 kDa MWCO (molecular weight cut off) mini dialysis units (Millipore®) against the same buffer to remove protein fragments and salts. The dialyzed protein solution was passed through a YM-100 filter (100 kDa MWCO, Millipore®) to remove higher aggregates. The resulting protein solution was used for experiments.

Example 3

Amyloid Fibril Formation for Understanding the Morphology of Protein Aggregates The concentration of LMW was measured using UV absorbance at 280 nm using a UV spectrophotometer. Considering the molar absorptivity (c) 5960 for α-Syn and its mutant. The final protein concentration was adjusted to 300 μM. The 500 μl protein was aliquoted in 1.5 ml Eppendorf tube in Glycine NaOH buffer pH7.4 (20 mM, 0.01% Sodium azide). The Eppendorf tubes were placed in the Echo-Therm™ model RT11 rotating mixture (Torrey Pines Scientific, USA) at 50 r.p.m at 37 degree C. inside an incubator. ThT fluorescence and CD was measured at a regular time interval to monitor the aggregation kinetics of α-Syn and its mutants. Amyloid fibrils formation was confirmed by TEM and AFM.

Example 4

Thioflavin T (ThT) Binding Assay for Understanding Protein Aggregation Kinetics For ThT binding assay protein sample diluted to 7.5 μM in 20 mM glycine NaOH, pH 7.4, 0.01% sodium azide. 1 mM ThT was prepared in Tris-HCL buffer (pH 8, 0.01% sodium azide). 4 μl of 1 mM ThT was added to the protein sample. ThT fluorescence was performed in Hellma® cuvette (10 mm pathlength, 500 μl) and spectra were recorded using Jasco FP-8500 spectrofluorometer with excitation at 450 nm and emission in the range from 460-500 nm. Slit width for both excitation and emission were kept to 5 nm. The ThT fluorescence obtained at 480 nm was plotted for all protein samples against incubation time.

Example 5

Circular Dichroism (CD) Spectroscopy for Monitoring Secondary Structural Changes in the Protein Secondary structural change in protein (WT α-Syn and its mutants) during aggregation study was monitored using circular dichroism spectroscopy. 7.5 μM of protein solution was placed into 0.1 cm path length quartz cell (Hellma®, Forest Hills, NY) and a spectrum was recorded over the wavelength range of 198 to 260 nm at 25 degree C. For each sample, three scans were taken, and an average of the scans was taken. Raw data processed by subtracting buffer and smoothing according to the manufacturer's instruction.

Example 6

Transmission Electron Microscopy for Visualizing Morphology of Protein Aggregates The 50 μM protein sample was prepared in 20 mM glycine NaOH pH7.4, 0.01% sodium azide, and 10 μl sample was spotted on glow discharged, carbon-coated formvar grid (Electron microscopy sciences, fort Washington, PA) and incubated for 10 min. The grid was then washed with autoclaved Milli Q water. This was followed by staining with 1% (w/v) uranyl formate for 10 min The sample was air-dried for 10 min imaging was done using electron microscopy (JEM2100F) at 200 kV. The images were acquired at 10,000×-20000× magnification using TEM (JEM2100F) at 200 kV. Gatan digital map were used for image recording.

Example 7

MTT Assay

To determine toxicity of the protein aggregates to cell, SH-SYSY cells were grown in Dulbecco's Modified Eagle Medium (DMEM) (Himedia, India) supplemented with 10% FBS (Invitrogen™, USA), 100 units/ml penicillin and 100 μg/mL streptomycin in a 5% CO2 in incubator at 37 degree C. Cells were seeded at 10,000 cells/well. After 24 hour of incubation, media change was given along with 25 μM protein. Cells were allowed to grow for 24 h in $CO^2$ incubator. 10 μl of MTT (5 mg/ml in PBS) was added to all wells and incubated for 4 hours. After 4 hours, 100 μl of a solution containing 50% dimethylformamide and 20% SDS (pH 4.8) was added and incubated overnight at 37 degree C. Absorbance at 560 nm was measured by SpectraMax® M2 microplate reader (Molecular Devices, USA).

Example 8

In-Vitro α-Syn Seed Preparation

The final protein concentration (LMW) was adjusted to 300 μM in 20 mM Gly NaOH buffer (pH7.4, 0.01% sodium azide). The protein solution in microcentrifuge tubes was kept for rotation at 50 r.p.m in EchoThermo model, R11 rotating mixture (Torrey Pines Scientific™, USA) in 37 degree C. incubator. The conversion of unstructured protein into highly ordered β-sheet fibrils (amyloid formation) was monitored using CD and ThT fluorescence. The seeds were generated by sonicating the wild type fibrils to produce small fibril fragmented seeds. Fibrils were sonicated at 20% amplitude with 3 sec on and 1 sec off pulse for 3 min. The generated seeds are used for further studies.

Example 9

Method for Isolation of In-Vitro α-Syn Oligomer

To isolate α-Syn oligomer seeds from the reaction mixture, the final concentration of LMW αSyn protein was adjusted to 300 μM in 20 mM Gly NaOH buffer (pH7.4, 0.01% sodium azide). The protein solution was incubated with rotation at 50 r.p.m in 37 degree C. incubator. Periodically oligomer formation was monitored using ThT fluorescence and circular dichroism spectra analysis for structural transition. After 48 hr of incubation the reaction mixture was centrifuged at 14000 g for 15 min at 4 degree C. to separate premature pelletable fibrils. The supernatant was passed through an activated 100 kDa cut-off membrane filter. Retentate and flow-through were collected and concentration was measured for all three different separated samples. The retentate (Oligomer) was used for further study. Nanomolar ($10^{-9}$M), picomolar ($10^{-12}$M) and femtomolar ($10^{-15}$M) concentrations of oligomeric seeds were used for the aggregation study.

Example 10

Co-Aggregation and Seeding of E46P and A53P with WTα-Syn

Samples of seed-free α-Syn (WT, E46P, and A53P) were adjusted to 150 μM in glycine NaOH buffer pH 7.4, 0.01% sodium azide and placed at 37 degree C. in black costar 96 well clear bottom plate in the presence of 10 μM concentration of ThT at a final volume 200 μl as a control. For coaggregation study, WT and proline mutate proteins with 1:0.5, 1:1, and 1:2 ratios prepared in glycine NaOH buffer pH 7.4, 0.01% sodium azide. Whereas the test samples were prepared by addition of seed (WT α syn) at a concentration of 1% v/v, picomolar ($10^{-12}$ M), and Femtomolar ($10^{-15}$ M) to 150 μM of 200 μl monomer sample, for seeding experiment. Samples were placed at 37 degree C. in black costar 96 well clear bottom plate in the presence of 10 μM concentration of ThT at a final volume 200 μl as a control. The increase in ThT fluorescence was monitored at excitation of 450 nm and emission of 480 nm using SpectraMax® M2e microplate reader.

Example 11

E46P α-Syn Aggregation in Presence of Oligomer Seed

Samples of seed-free WT α-Syn mutant at a concentration of 200 μM in 20 mM glycine NaOH, pH 7.4, 0.01% sodium azide buffer was placed in a 1.5 ml Eppendorf tube and incubated alone and in the presence of nano, pico, and femtomolar synthetic oligomeric seed and subjected to agitation ~50 rpm. ThT fluorescence was measured at every time point with excitation at 450 nm and emission 460-500 nm using a Jasco fluorescence instrument (JASCO FP 8500) with 5 nm slit width and medium sensitivity. The ThT fluorescence at 480 nm was plotted and data fitted to a sigmoidal curve.

Example 12

Collection of 'Healthy' Blood Samples and Isolation of Serum

The healthy blood sample was collected from voluntary participants at IIT Bombay/KEM hospital. 10 ml of the blood sample was drawn from healthy volunteers by professional doctors. The blood sample was immediately returned to IIT-Bombay where the follow-up procedures (isolation of blood components such as serum) were performed. The blood sample was kept at room temperature (25 degree C.) for 45 min for precipitating RBCs and centrifuged at 1500 g for 15 minutes. The serum was carefully isolated from the top of the solution and was immediately put to PMCA experiments. The RBC and WBC fraction of blood was treated with concentrated NaOH and sent for incineration. The allowance to use blood samples for experiments was sanctioned by IIT Bombay ethical clearance committee mutually.

Example 13

Blood Simulated WT and E46P α-Syn Aggregation Assay

Samples of seed-free WT and E46P at a concentration of 200 μM in 20 mM glycine NaOH (pH 7.4, 0.01% sodium azide) buffer were placed in a 1.5 ml microfuge tube. For each test, we added 40 μl human blood serum from the control participant. The seed spiked serum and serum alone was centrifuged at 35000 r.p.m to remove the aggregation interfering components of the blood before reaction setup. The pellet was redissolved in glycine NaOH (pH 7.4, 0.01% sodium azide) buffer. Positive control samples consisted of WT and E46P α-Syn spiked with preformed α-Syn seeds. Samples were subjected to continuous agitation at 50 r.p.m in 37 degree C. incubator. The increase in ThT fluorescence was monitored at excitation of 450 nm and emission in the range from 460-500 nm. ThT fluorescence was performed in Hellma cuvette (10 mm pathlength, 500 μl) and spectra were recorded using JascoFP-8500 spectrofluorometer. Slit width for both excitation and emission were kept to 5 nm. The ThT fluorescence obtained at 480 nm was plotted for all protein samples against incubation time.

Example 14

PMCA with Healthy Serum Sample Spiked with Different Concentrations of Seed 25 mg of E46P α-Syn was dissolved in 20 mM Glycine NaOH (pH 7.4). Low molecular weight (LMW) E46P-α-Syn was prepared according to the standard protocol. The PD simulated serum samples were prepared by addition of various concentrations ($10^{-10}$, $10^{-13}$, and $10^{-15}$ M seed) of WT α-Syn fibril seeds to a healthy serum sample. Serum alone was used as a control for our experiments. 200 μM of LMW E46P α-Syn was added to the simulated blood sample to prepare the PMCA reaction mixture. Manually we programmed it for 6 hr incubation at 37 degree C. followed by bath sonication for 15 min for initial 8 cycles and another 16 cycles 3 hr incubation followed by 15 min bath sonication at 40 degree C. We have performed multiple rounds of 24-cycles each and observed the amplification of pathological aggregates after completion of the round. Incubation accelerates the polymerization process of α-Syn and elongates the misfolded form whereas the sonication breaks the elongated fibrils into new seeds that can act upon the remaining pool of monomer. The sonication—incubation cycle for PMCA was run for multiple rounds. At different time-points, 5 μl of each PMCA sample was diluted to 150 μl using Glycine NaOH buffer (pH 7.4). 2 μl of ThT was added to the solution and ThT fluorescence was measured at 480 nm to check for protein aggregation. After 100 h of PMCA, the solutions were ultracentrifuged at 35000 r.p.m at 4 degree C. for 45 min. The pellets were washed with 1× Glycine NaOH buffer, pH 7.4, and again ultracentrifuged. The obtained pellets were subsequently dissolved in 100 μl autoclaved MQ water. 10 μl of the final solution was loaded on the TEM grids. The samples were negatively stained with uranyl formate and subsequently imaged at magnifications ranging from 24000 to 60000× with the help of TEM. To further check that the fibril fraction indeed contained α-Syn, we performed western blot analysis of the pellets at different time-points (0, 50, 100, and 120 h) using the standard protocol. Briefly, the samples were resolved in 15% SDS-PAGE and proteins from the gel transferred to a nitrocellulose membrane by wet transfer. After transfer, the membrane blocked with skim milk powder for 2 hr at room temperature at slow rocking followed by washing with Tris buffer saline (50 mM Tris, 150 mM NaCl). The primary antibody against a-synuclein (LB509, 1:1600 dilution) was added to the membrane and incubated at 4 degree C. overnight. The primary antibody then removed by two washes with TBST (0.01% tween) followed by incubation of the membrane with anti-mouse horseradish peroxidase (HRP) conjugated secondary antibody for 2 hr at room temperature. The unbound secondary antibody was washed with TBST (0.01% tween). The membrane was exposed to the chemi-luminescent substrate and the signal was captured on X-ray films. The intensity of the bands was computed using ImageJ (Fiji).

Example 15

Diagnosis of PD Patients and Study Design

To investigate the misfolded α-Syn in the blood of patients with PD, blood samples from 12 clinically diagnosed PD patients and 7 healthy controls were analyzed. The samples were collected at the King Edward Memorial Hospital, Mumbai, India. The blood collection and the overall study was approved by both the KEM ethical committee and IIT Bombay institutional ethical committee. The participants provided written informed consent. Samples were obtained according to internationally standardized criteria including UK Brain bank guidelines. The Hoen and Yahr scale was used to grade the progression of PD. Stage 1 in the scale corresponds to the patient with unilateral involvement only and stage 5 corresponds to patients with wheelchair-bound or bedridden unless aided. Blood samples were collected in the morning using an EDTA free vacutainer. The samples were transported within an hour to the laboratory without the blood and serum mixing.

After collection of the blood, the blood was allowed to clot by leaving it undisturbed at room temperature for 15 to 30 minutes. The clot was removed from the samples by carrying out centrifugation at 2500 rpm for 10 min at 4 degree C. The resulting supernatant i.e. serum, was immediately transferred to clean autoclaved 0.5 ml microcentri-fuge tubes and stored at −80 degrees C. for further use.

For carrying out cyclic amplification the aliquots of α-Syn protein (WT and E46P) 200 μM (prepared in 20 mM glycine NaOH buffer, pH 7.4, 0.01% sodium azide) were mixed with serum sample of healthy individuals and PD patients. The samples were loaded into a 0.5 ml Eppendorf tube and the cycle was programmed for 6 hr incubation at 37 degree C.; followed by bath sonication for 15 min for initial 8 cycles; and another 16 cycles 3 hr incubation; followed by 15 min bath sonication at 37 degree C. Four rounds of 24 cycles each were carried out and characterization of amplified pathological aggregates was performed after completion of each round. After the PMCA assay, the samples were ultra-centrifuged at 35000 rpm for 45 min and redissolved in 100 μl 20 mM glycine NaOH buffer pH7.4, 0.01% sodium azide. The samples were fractioned by SDS-PAGE under reducing conditions followed by electroblotting onto nitrocellulose membrane. The samples were then probed with LB509 antibody diluted 1:1600 with 2.5% BSA (Bovine serum albumin) in TBST (Tris-buffered saline 0.01% Tween 20). Western blot analysis was used to characterize and recognized the presence of pathological aggregates. The immunoreactive bands were characterized by chemiluminescence assay by exposing the membrane to a chemiluminescent substrate. Images were processed using ImageJ for quantitative analysis.

Thioflavin T (ThT) binding assay was carried out after completion of each PMCA round. ThT fluorescence was acquired by diluting 5 μl of redissolved pellet sample to 200 μl in 20 mM glycine NaOH buffer, pH 7.4, 0.01% sodium azide. 1 mM ThT was prepared in Tris HCL buffer (pH 8, 0.01% sodium azide). 2 μl of 1 mM ThT was added to the samples. The spectra were recorded as mentioned in Example 4.

To investigate the secondary structure transition CD spectroscopy was performed. The spectra were acquired after completion of each PMCA round by diluting 5 μl of redis-solved pellet samples in 200 μl in 20 mM glycine NaOH buffer, pH 7.4, 0.01% sodium azide. The sample analysis was performed as described in Example 5.

Example 16

Congo Red Dot (CRD) Test for High Throughput Screening of PD and HC Samples

To evaluate the amplified amyloid samples on nitrocellulose membrane for high throughput screening, congo red dot test was performed. 10 μl of final end product of PMCA assay was mixed with 1 μl of stock aqueous solution of CR (5 mg/mL, Sigma). A blank sample was prepared by adding 1 μl of CR stock solution to 10 μl glycine NaOH buffer (pH 7.4, 0.01% sodium azide). After 30 min incubation at room temperature, 5 μl of sample mixture was spotted on nitro-cellulose membrane (in duplicates). The membrane was then rinsed with double distilled water and then photographed using ImageQuant™ LASSOO to acquire a picture (before wash). Further, the membrane was washed with increasing concentrations of ethanol (50%, 70% and 90%) till the red color of the blank sample disappeared completely. The red colour of the samples which did contain amplified misfolded protein disappeared, whereas the samples containing mis-folded proteins retained the dye and remained visibly red. Following this picture was taken (After wash). The Congo red intensity was further measured using Image J software.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described.

---

We claim:

1. An invitro method for detection of Synucleinopathy in an individual, said method comprising:
    obtaining a sample from said individual;
    mixing said sample with a mutant to obtain a reaction mixture;
    incubating the reaction mixture to facilitate amplification of pathological α-Syn aggregates;
    detecting the presence of amplified pathological aggregates; and
    determining presence of the aggregates for detecting Synucleinopathy,
    wherein the mutant is an artificial mutant alpha-Synuclein (α-Syn) protein, comprising a polypeptide having at least one amino acid sequence selected from the group consisting of SEQ ID NO: 2, SEQ ID NO: 3, and SEQ ID NO: 4, said mutant having decreased or no ability to self-aggregate.

2. The method as claimed in claim 1, wherein said detecting step comprises mixing said amplified pathological aggregates and Congo red dye, and incubating; placing the mixture on suitable reaction paper; and detecting based on retention of said Congo red dye on the paper.

3. The method as claimed in claim 1, wherein said Synucleinopathy is at least one condition selected from the group consisting of Parkinson's disease, Dementia with Lewy bodies, Lewy body variant of Alzheimer disease, Multiple system atrophy, and Autonomic dysfunction.

4. The method as claimed in claim 1, wherein the step of incubating further includes sonicating the reaction mixture.

5. The method as claimed in claim 1, wherein the pathological α-Syn aggregates are present in the body fluids of said individuals.

6. The method as claimed in claim 1, wherein the sample is a biological sample consisting of body fluids such as blood, blood components, plasma, serum, saliva, and cerebrospinal fluid, obtained from a said individual.

7. The method as claimed in claim 1, wherein the incubation step is performed by subjecting the mixture to seed amplification assays.

8. The method as claimed in claim 1, wherein said detecting of pathological α-Syn aggregate includes at least one method selected from a group consisting of Thioflavin T fluorescence assay, western blotting method, immunoassays, immunostaining, Congo red dot assay, and enzyme-linked immunosorbent assay (ELISA).

* * * * *